US006660763B2

(12) United States Patent
Tang et al.

(10) Patent No.: US 6,660,763 B2
(45) Date of Patent: *Dec. 9, 2003

(54) BIS-INDOLYLQUINONE COMPOUNDS

(75) Inventors: Peng Cho Tang, Moraga, CA (US);
Gerald McMahon, San Francisco, CA (US); G. Davis Harris, Jr., San Francisco, CA (US); Ken Lipson, San Mateo, CA (US)

(73) Assignee: Sugen, Inc., South San Franscisco, CA (US)

(*) Notice: Subject to any disclaimer, the term of this patent is extended or adjusted under 35 U.S.C. 154(b) by 0 days.

This patent is subject to a terminal disclaimer.

(21) Appl. No.: 09/564,777

(22) Filed: May 4, 2000

(65) Prior Publication Data
US 2002/0156116 A1 Oct. 24, 2002

Related U.S. Application Data

(62) Division of application No. 09/405,244, filed on Sep. 24, 1999, now Pat. No. 6,376,529, which is a continuation of application No. 09/072,861, filed on May 5, 1998, now Pat. No. 6,110,957, which is a division of application No. 08/964,791, filed on Nov. 5, 1997, now Pat. No. 5,786,488.
(60) Provisional application No. 60/030,604, filed on Nov. 13, 1996, and provisional application No. 60/042,989, filed on Apr. 14, 1997.

(51) Int. Cl.$^7$ ...................... A61K 31/404; C07D 403/08

(52) U.S. Cl. ........................................ 514/414; 548/455

(58) Field of Search ........................... 548/455; 514/414

(56) References Cited

U.S. PATENT DOCUMENTS

| 3,917,820 | A | 11/1975 | Brewer et al. | 424/122 |
|---|---|---|---|---|
| 5,780,496 | A | 7/1998 | Tang et al. | 514/414 |
| 5,786,488 | A | 7/1998 | Tang et al. | 548/455 |
| 6,051,597 | A | 4/2000 | Zhang et al. | 514/414 |
| 6,110,957 | A | 8/2000 | Tang et al. | |
| 6,239,161 | B1 * | 5/2001 | Tang et al. | 514/414 |
| 6,376,529 | B1 | 4/2002 | Tang et al. | |

FOREIGN PATENT DOCUMENTS

| EP | 0 095 239 | 11/1983 |
|---|---|---|
| JP | 61-91167 | 5/1986 |
| JP | 63-60966 | 3/1988 |
| WO | WO 96/30762 | 10/1996 |
| WO | 96/40115 | 12/1996 |
| WO | 98/20874 | 5/1998 |
| WO | WO 99/51225 | 10/1999 |

OTHER PUBLICATIONS

Arai et al., Chem. Pharm. Bull. (Apr. 1981), 29(4), pp. 961–969.*
Arai et al., Chem. Pharm. Bull. (Apr. 1981), 29(4), pp. 991–999.*
Arai et al., CA 95:115187, 1981.*

Alvi et al., "Asterriquinones Produced by *Aspergillus candidus* Inhibit Binding of the Grb–2 Adapter to Phosphorylated EGF Receptor Tyrosine Kinase," *Journal of Antibiotics* 52: 215–223 (1999).
Fredenhagen et al., "Semicochliodinol A and B: Inhibitors of HIV–1 Protease and EGF–R Protein Tyrosine Kinase Related to Asterriquinones Produced by the Fungus *Chrysosporium merdarium*," *Journal of Antibiotics* 50: 395–401 (1997).
Harris, Jr., et al., "A One–Pot, Two–Step Synthesis of Tetrahydro Asterriquinone E," *Organic Letters* 1: 431–433 (1999). American Chemical Society.
Kaji et al., "Studies on the Cytotoxicity of Asterriquinone Derivatives," *Journal of Antibiotics* 51: 235–238 (1998).
Kaji, et al., "Preparation and structure–activity Relationships of Novel Asterriquinone Derivatives," *Chem. Pharm. Bull.* 46: 1325–1329 (1998). Pharmaceutical Society of Japan. (Chemical Abstracts 129:275778).
Liu, et al., "Discovery of a Potent, Highly Selective, and Orally Efficacious Small–Molecule Activator of the Insulin Receptor," *J. Med. Chem.* 43: 3487–3494 (2000). American Chemical Society.
Ookie, et al., "Structures of a New Type of Indoloditerpene, Petromindole, and a New Asterriquinone Derivative, PM–53, from the Ascostromata of *Petromyces muricatus*," *Chem. Pharm. Bull.* 45: 1694–1696 (1997).
Wood, Jr., et al. "The Basal SAR of a Novel Insulin Receptor Activator," *Bioorganic & Medicinal Chemistry Letters* 10:: 1189–1192 (2000). Pergamon.
Arai et al., 1981, "Metabolic Products of *Aspergillus terreus* IV. Metabolites of the Strain IFO 8835. (2) The Isolation and Chemical Structure of Indolyl Benzoquinone Pigments", Chem. Pharm. Bull. 29: 961–969.
Arai et al., 1981, "Metabolic Products of *Aspergillus terreus* V. Demethylation of Asterriquinones", Chem. Pharm. Bull. 29: 991–999.
Arai et al., 1981, "Metabolic Products of *Aspergillus terreus* IV. Metabolites of the Strain IFO 8835. (2) The Isolation and Chemical Structures of Colorless Metabolites", Chem. Pharm. Bull. 29: 1005–1012.

(List continued on next page.)

*Primary Examiner*—Laura L. Stockton
(74) *Attorney, Agent, or Firm*—Beth A. Burrous; Foley & Lardner

(57) ABSTRACT

The present invention relates to a class of indolylquinone compounds that inhibit GRB-2 adaptor protein function, pharmaceutical compositions comprising these compounds, and methods for ameliorating the symptoms of cell proliferative disorders associated with GRB-2 adaptor protein function using these compounds. The present invention further relates to methods for treating insulin-related disorders, such as diabetes, insulin resistance, insulin deficiency and insulin allergy, and for ameliorating the symptoms of insulin-related disorders, using certain indolylquinone compounds and pharmaceutical compositions thereof. The present invention also relates to novel synthetic methods for the preparation of mono- and bis-indolylquinone compounds.

4 Claims, 1 Drawing Sheet

OTHER PUBLICATIONS

Arai et al., 1990, "Metabolic Products of *Aspergillus terreus* X. Biosynthesis of Asterriquinones", Chem. Pharm. Bull. 38: 2929–2932.

Brewer et al., 1961, "The Production of Cochliodinol and a Related Metabolite by Chaetomium Species", Can. J. Microbiol. 14: 861–866.

Bu'Lock and Harley–Mason, 1951, "Melanin and Its Precursors. Part II, Model Experiments on the Reactions Between Quinones and Indoles, and Consideration of a Possible Structure for the Melanin Polymer", J. Chem. Soc. London, No. 152, pp. 703–712.

Buday and Downward, 1993, "Epidermal Growth Factor Regulates the Exchange Rate of Guanine Nucleotides on p21 ras in Fibroblasts", Mol. Cell. Biol. 13: 1903–1910.

Buday and Downward, 1993," Epidermal Growth Factor Regulates p21 ras through the Formation of a Complex of Receptor, Grb2 Adaptor Protein, and Sos Nucleotide Exchange Factor", Cell 73: 611–620.

Cantley et al., 1991, "Oncogenes and Signal Transduction", Cell 64: 281–302.

Chardin et al., 1993, "Human Sos1: a Guanine Nucleotide Exchange Factor for Ras that Binds to Grb2", Science 260: 1338–1343.

Colona et al., CA 59:542c, No. 1, Jul. 8, 1963.

Colonna, M and Monti, A., *Gazzetta Chimica Italiana* (1982) 92: 1401–1421.

Corradini, M.G. et al., *Gazezetta Chimica Italiana* (1989) 119: 153–156.

Dymecki et al., 1990, "Specific Expression of a Tyrosine Kinase Gene, blk, in B Lymphoid Cell", Science 247: 332–336.

Egan et al., 1993, "Association of Sos Ras Exchange Protein with Grb2 is Implicated in Tyrosine Kinase Signal Transduction and Transformation", Nature 363:45–51.

Fischer et al., 1991, "Protein Tyrosine Phosphatases: A Diverse Family of Introcellular and Transmembrane Ezymes", Science 253:401–406.

Gale et al., 1993, "Grb2 Mediates the EGF–Dependent Activation of Guanine Nucleotide Exchange on ras", Nature 363:88–92.

Gibbs et al., 1990, "Modulation of Guanine Nucleotides Bound to ras in NIH3T3 Cells by Oncogenes, Growth Factors, and the GTPase Activating Protein (GAP)", J. Biol. Chem. 265:2037–2042.

Gishizky and Witte, 1992, "Initiation of Deregulated Growth of Multipotent Progenitor Cells by bcr–abl in vitro", Science 256:836–839.

Grazia et al., 1989, CA 111:232–499.

Hanks et al.; 1988, "The Protein Kinase Family:Conserved Features and Deduced Phylogeny of the Catalytic Comains", Science 241:42–52.

Hao et al., 1989, "Isolation and Sequence Analysis of a Novel Human Tyrosine Kinase Gene", Mol. Cell. Biol. 9:1587–1593.

Hardie, 1990, "Roles of Protein Kinases and Phosphatases in Signal Transduction", Symp. Soc. Exp. Biol. 44:241–255.

Horcher et al., 1986, "Biologically Active Products from Mold Fungi. 35. Total Synthesis of Cochliodinol", Liebigs Ann. Chem. 10:1765–1771 (in German with translation).

Hunter, 1991, "Cooperation Between Oncogenes", Cell 64:249–270.

Jerram et al., 1975, "The Chemistry of Cochliodinol, a Metabolite of Chaetomium Spp.", Can. J. Chem. 53:727–737.

Kaji et al., 1995, "Partial Deacetylation of Asterriquinone Diacetate by Aqueous Sodium Bicarbonate in Pyridine", Chem. Pharm. Bull. 43:1818–1820.

Kaji et al., 1994, "Four New Metabolites of *Aspergillus terreus*", Chem. Pharm. Bull. 42:1682–1684.

Kaziro et al., 1991, "Structure and Function of Signal–Transducing GTP–Binding Proteins", Ann. Rev. Biochem. 60:349–400.

Kipreos et al., 1990, "Differential Phosphorylation of c–abl in Cell Cycle Determined by cdc2 Kinase and Phosphatase Activity", Science 248:217–220.

Koch et al., 1991, "SH2 and SH3 Domains: Elements that Control Interactions of Cytoplasmic Signaling Proteins", Science 252:668–674.

Kruh et al., 1986, "A Novel Human Gene Closely Related to the abl Proto–Oncogene", Science 234:1545–1548.

Levitzki and Gazit, 1995, "Tyrosine Kinase Inhibition:An Approach to Drug Development", Science 267:1782–1788.

Li et al., 1994, "A New Function for Phosphotyrosine Phosphatase:Linking GRB2–Sos to a Receptor Tyrosine Kinase", Mol. Cell. Bio. 14:509–517.

Li et al., 1992, "Nerve Growth Factor Stimulation of the Ras–Guanine Nucleotide Exchange Factor and GAP Activities", Science 256:1456–1459.

Li et al., 1993, "Guanine–Nucleotide–Releasing Factor hSos 1 Binds Grb2 and Links Receptor Tyrosine Kinases to Ras Signaling", Nature 363:85–88.

Lowenstein et al., 1992, "The SH2 and SH3 Domain–Containing Protein GRB2 Links Receptor Tyrosine Kinases to ras Signaling", Cell 70:431–442.

Lowy and Willumsen, 1993, "Function and Regulation of RAS", Ann. Rev. Biochem. 62:851–891.

Lugo and Witte, 1989, "The BCR–ABL Oncogene Transforms Rat–1 Cells and Cooperates with v–myc", Mol. Cell. Biol. 9: 1263–1270.

Maness, 1992, "Nonreceptor Protein Tyrosine Kinases Associated with Neuronal Development", Dev. Neurosci. 14:257–270.

Marth et al., 1985, "A Lymphocyte–Specific Protein–Tyrosine Kinase Gene is Rearranged and Overexpressed in the Murine T Cell Lymphoma LSTRA", Cell 43:393–404.

Martinez et al., 1987, "Neuronal pp60csrc Contains a Six–Amino Acid Insertion Relative to Its Non–Neuronal Counterpart", Science 237:441–415.

Matuoka et al., 1993, "Ash/Grb–2, a SH2/SH3–Containing Protein, Couples to Signaling for Mitogenesis and Cytoskeletal Reorganization by EGF and PDGF", EMBO J. 12:3467–3473.

Mayer et al., 1988, "A Novel Viral Oncogene with Structural Similarity to Phospholipase C", Nature 332:272–275.

Mayer and Baltimore, 1993, "Signaling through SH2 and SH3 Domains", Trends in Cell Biol. 3:8–13.

McLaughlin et al., 1987, "In vitro Transformation of Immature Hematopoietic Cells by the P210 *BCR/ABL* Oncogene Product of the Philadelphia Chromosome", Proc. Natl. Acad. Sci. USA 84:6558–6562.

Medema et al., 1993, "Ras Activation by Insulin and Epidermal Growth Factor through Enhanced Exchange of Guanine Nucleotides on p21ras", Mol. Cell. Biol. 13:155–162.

Meiler and Taylor, 1970, "The Effect of Cochlidinol, a Metabolite of *Chaetomium cochliodes*, on the Respiration of Microspores of *Fusarium oxysporum*", Can. J. Microbiol. 17:83–86.

Mocek et al., 1995, "Isolation and Structure Elucidation of Five New Asteriquinones from Aspergillus, Humicola and Botryotricum Species", J. Antibiotics 49: 854–859.

Moehlau et al., 1911, Beilstein Reference 1–21–00–00420 of Chem. Ber. 44, p. 3614.

Möhla, R. and Redlich, A., *Berichte der Deutschen Chemischen Gesellchaft* (1912) 3605–3618.

Morgan et al., 1989, "Mitosis–Specific Phosphorylation of p60c–src by p34cdc2–Associated Protein Kinase", Cell 57:775–786.

Muller et al., 1991, "BCR First Exon Sequences Specifically Activate the BCR/ABL Tyrosine Kinase Oncogene of Philadelphia Chromosome–Positive Human Leukemias", Mol. Cell. Biol. 11:1785–1792.

Nurse, 1990, "Universal Control Mechanism Regulating Onset of M–Phase", Nature 344:503–508.

O'Leary and Hanson, 1982, "Hinnulquinone, a Bis–Indoly–2,5–Dihydroxybenzoquinone Pigment from *Nodulisporum hinnuleum*", Tetrahedron Lett. 23:1855–1856.

Olivier et al.,1993, "A Drosophila SH2–SH3 Adaptor Protein Implicated in Coupling the Sevenless Tyrosine Kinase to an Activator of Ras Guanine Nucleotide Exchange, Sos", Cell 73:179–191.

Ono et al., 1991, "Inhibition of HIV Reverse Transcriptase Activity by Asterriquinone and Its Analogs", Biochem. Biophys. Res. Comm. 174:56–62.

Pawson and Schlessinger, 1993, "SH2 and SH3 Domains", Current Biology, 3:434–442.

Pawson and Gish, 1992, "SH2 and SH3 Domains:from Structure to Function", Cell 71:359–362.

Pendergrast et al., 1993, "BCR–ABL–Induced Oncogenesis is Mediated by Direct Interaction with the SH2 Domain of the GRB–2 Adaptor Protein", Cell 75:175–185.

Posada and Cooper, 1992, "Molecular Signal Integration. Interplay between Serine, Threonine, and Tyrosine Phophorylation", Mol. Biol. Cell 3:583–592.

Roebroek et al., 1985 "The Structure of the Human c–fes/fps Proto–Oncogene", EMBO J. 4:2897–2903.

Rozakis–Adcock et al., 1993, "The SH2 and SH3 Domains of Mammalian Grb2 Couple the EGF Receptor to the Ras Activator mSos1", Nature 363:83–85.

Sadowski et al., 1986, "A Noncatalytic Domain Conserved among Cytoplasmic Protein–Tyrosine Kinases Modifies the Kinase Function and Transforming Activity of Fujinami Sarcoma Virus p130gas/fps", Mol. Cell. Biol. 6:4396–4408.

Satoh et al., 1990, "Platelet–Derived Growth Factor Stimulates Formation of Active p21ras–GTP Complex in Swiss Mouse 3T3", Proc. Nat. Acad. Sci. USA 87: 5993–5997.

Sawyers et al., 1992, "Propogation of Human Myeloid Leukemias in the SCID Mouse", Blood 79:2089–2098.

Schlaepfer et al., 1994, "Integrin–Mediated Signal Transduction Linked to Ras Pathway by Grb2 Binding to Focal Adhesion Kinase", Nature 372:786–791.

Schlessinger, 1993, "How Receptor Tyrosine Kinases Activate Ras", TIBS 18:273–275.

Schlessinger and Ullrich, 1992, "Growth Factor Signaling by Receptor Tyrosine Kinases", Neuron 9:383–391.

Scott and Soderling, 1992, "Serine/Threonine Protein Kinases", Curr. Opin. Neurobiol. 2:289–295.

Sekita, 1983, "Isocochliodinol and Neocochliodinol, Bis(3–Indolyl)–Benzoquinones from Chaetomium Spp.", Chem. Pharm. Bull. 31:2998–3001.

Shimizu et al., 1982, "Antitumor Activity of Asterriquinones from Aspergillus Fungi. IV. An Attempt to Modify the Structure of Asterriquinones to Increase the Activity", Chem. Pharm. Bull. 30:1896–1899 (Chem. Abstr. 97:103877y).

Shimizu and Koshimura, 1990, "Interaction of Asterriquinone with Deoxyribonucleic Acid in vitro", Chem. Pharm. Bull. 38:2617–2619.

Shimizu et al., 1982, "Antitumor Effect and Structure–Activity Relationship of Asterriquinone Analogs", Gann. 73:642–648 (Chem. Abstr. 97:174470w), Shtivelman et al., 1986, "Alternative Splicing of RNA's Transcribed from the Human abl Gene and from the bcr–abl Fused Gene", Cell 47:277–284.

Simon et al., 1991, "Diversity of G Proteins in Signal Transduction", Science 252:802–808.

Simon et al., 1993, "An SH3–SH2–SH3 Protein is Required for p21Ras1 Activation and Binds to Sevenless and Sos Protein in vitro", Cell 73:169–177.

Skehan et al., 1990, "New Colorimetric Cytotoxicity Assay for Anticancer–Drug Screening", J. Natl. Cancer Inst. 82:1107–1112.

Smith et al., 1986, "Requirement for the c–ras Proteins during Viral Oncogene Transformation", Nature 320:540–543.

Stahl et al., 1988, "Sequence Similarity of Phospholipase C with the Non–Catalytic Region of src", Nature 332:269–272.

Sukegawa, et al., 1997, "Characterization of cDNA Clones for the Human c–yes Gene", Mol. Cell. Biol. 7:41–47.

Ullrich and Schlessinger, 1990, "Signal Transduction by Receptors with Tyrosine Kinase Activity", Cell 61:203–212.

van der Geer and Hunter, 1993, "Mutation of Tyr697, a GRB2–Binding Site, and Tyr721, a PI 3–Kinase Binding Site, Abrogates Signal Transduction by the Murine CSF–1 Receptor Expressed in Rat–2 Fibroblasts", EMBO J. 12:5161–5171.

Veillette and Davidson, 1992, "Src–Related Protein Tyrosine Kinases and T–Cell Receptor Signaling", TIG 8:61–66.

Weaver et al., 1991, "CD8+T–Cell Clones Deficient in the Expression of the CD45 Protein Tyrosine Phosphatase Have Impaired Responses to T–Cell Receptor Stimuli", Mol. Cell. Biol. 11:4415–4422.

Yamamoto et al., 1976, "Studies on the Metabolic Products of *Aspergillus terreus*. I. Metabolites of the Strain IFO 6123", Chem. Pharm. Bull. 24:1853–1859.

Yamamoto et al., 1976, "Antitumor Activity of Asterriquinone, a Metabolic Product from *Aspergillus terreus*", Gann 67:623–624.

Yamamoto et al. ,1988, "Preparation of Indolybenzoquinines as Anti–Cancer Agents", Chem Abstr. 109:642 col. 2, abstract No.:210891m.

Yamanashi et al., 1987, "The yes–Related Cellular Gene lyn Encodes a Possible Tyrosine Kinase Similar to p56lck", Mol. Cell. Biol. 7:237–243.

Young and Babbitt, 1982, "2–(2–Methyl–3–Indolyl)–1, 4–Benzoquinone, a Reversible Redox Substrate at the Carbon–Paste Electrode in Acidic Aqueous–Ethanolic Media", J. Org. Chem. 47:1571–1572.

Alvi et al., 1999, "Asterriquinones Produced by *asperigillus candidus* Inhibit Binding of the Grb2 Adaptor to Phosphorylated EGF Receptor Tyrosine Kinase," J. Antibiotics, 52:215–223.

Caro et al., 1987, "Insulin Receptor Kinase in Human Skeletal Muscle from Obese Subjects with and Without Non–Insulin Dependent Diabetes," J. Clin. Invest., 79:1330–1337.

Ebina et al., 1985, "Expression of a Functional Human Insulin Receptor from a Cloned cDNA in Chinese Hamster Ovary Cells," Proc. Natl. Acad. Sci. USA, 82:8014–8018.

Ebina et al., 1985, "The Human Insulin Receptor cDNA:The Structural Basis for Hormone–Activated Transmembrane Signaling," Cell, 40:747–758.

Goodyear et al., 1995, "Insulin Receptor Phosphorylation, Insulin Receptor Substrate–1 Phosphorylation, and Phosphatidylinositol 3–Kinase Activity Are Decreased in Intact Skeletal Muscle Strips from Obese Subjects," J. Clin. Invest., 95:2195–2204.

Hubbard 1997, "Crystal Structure of the Active Insulin Receptor Tyrosine Kinase in Complex with Peptide Substrate and ATP Analog," EMBO J., 16:5572–5581.

Hubbard et al., 1994, "Crystal Structure of the Tyrosine Kinase Domain of the Human Insulin Receptor," Nature, 372:746–754.

Maignan et al., 1995, "Crystal Structure of the Mammalian Grb2 Adaptor," Science, 265:291–293.

Rosen 1989, "Structure and Function of Insulin Receptors," Diabetes, 38: 1508–1511.

Seely and Olefsky, 1994, "Potential Cellular and Genetic Mechanisms for Insulin Resistance in the Common Disorders of Diabetes and Obesity," Insulin Resistance, Moller, ed., Wiley & Sons, pp 187–252.

Ullrich et al., 1985, "Human Insulin Receptor and its Relationship to the Tyrosine Kinase Family of Oncogenes," Nature, 313:756–761.

White and Kahn, 1994, "Mechanisms of Insulin Action," Insulin Resistance, Moller, ed., Wiley & Sons, pp 9–47.

Zhang et al., 1999, "Discovery of a Small Molecule Insulin Mimetic With Antidiabetic Activity in Mice," Science, 284:974–977.

* cited by examiner

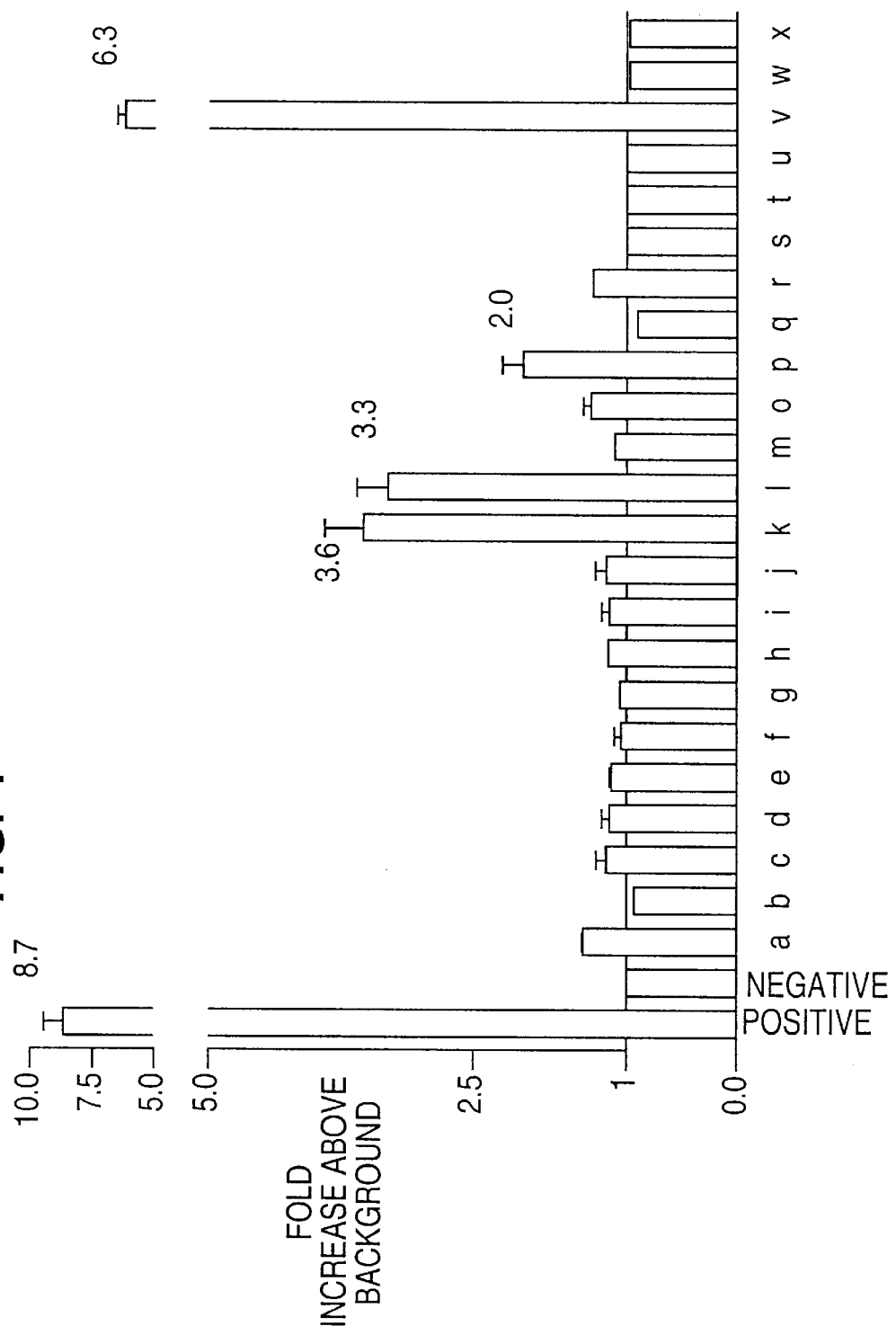

BIS-INDOLYLQUINONE COMPOUNDS

This application is a divisional of application Ser. No. 09/405,244, filed on Sep. 24, 1999, now U.S. Pat. No. 6,376,529; which is a continuation of application Ser. No. 09/072,861, filed May 5, 1998, now U.S. Pat. No. 6,110,957, which is a divisional of application Ser. No. 08/964,791, filed Nov. 11, 1997, now U.S. Pat. No. 5,786,488. The present application also claims priority to U.S. provisional application serial No. 60/030,604, filed Nov. 13, 1996, and U.S. provisional application Ser. No. 60/042,989, filed Apr. 14, 1997. The present application also claims priority to U.S. patent application Ser. No. 09/090,737, filed Jun. 4, 1998, now allowed, which is continuation of application Ser. No. 08/658,337, filed Jun. 5, 1996, now U.S. Pat. No. 5,780,496, which is a continuation-in-part of U.S. Ser. No. 08/476,136, filed Jun. 7, 1995, abandoned. The disclosures of the above-mentioned applications and patents are each hereby incorporated by reference in their entireties.

1. FIELD OF THE INVENTION

The present invention relates to methods and compositions for the inhibition of cell signal transduction associated with cell proliferative disorders. In particular, the invention relates to particular indolylquinone compounds that inhibit protein tyrosine kinase/adaptor protein interactions, and methods for utilizing such compounds. The present invention also relates to methods for treating insulin-related disorders using certain indolylquinone compounds. In particular, the invention is directed to methods for activating the insulin receptor tyrosine kinase in an animal.

2. BACKGROUND OF THE INVENTION

2.1 Indolylquinones

Research interest concerning indolylquinones grew out of early observations that extracts of Chaetomium exhibited antibiotic properties. These observations led researchers to attempt the isolation of active species from cultures of these microorganisms. For example, Brewer et al. disclose the isolation of a purple pigment, which was termed cochliodinol, from isolates of *Chaetomium cochliodes* and *Chaetomium globosum* (1968, "The Production of Cochliodinol and a Related Metabolite by Chaetomium Species," *Can. J. Microbiol.* 14:861–866). Brewer et al. also disclose the synthetic conversion of cochliodinol to a diacetate compound. Id. Further, the antifungal properties of cochliodinol have also been documented (Meiler et al., 1971, "The Effect of Cochliodinol, a Metabolite of *Chaetomium cochliodes* on the Respiration of Microspores of *Fusarium oxysporum,*" *Can. J. Microbiol.* 17: 83–86).

The structure of cochliodinol was elucidated by Jerram et al. in 1975. (1975, "The Chemistry of Cochliodinol, a Metabolite of Chaetomiium spp.," *Can. J. Chem.* 53:727–737). Jerram et al. reported the structure of cochliodinol as: 2,5-dihydroxy-3,6-di(5'-(2"-methylbut-$\Delta A^{2"}$-ene)-indolyl-3')-cyclohexadiene-1,4-dione. The conversion of cochliodinol to various other derivatives, including its dimethyl and diacetyl analogues, was also disclosed. Id. Some of these derivatives were highly colored and suitable for use as dyes, while others were colorless. Id. Sekita discloses the isolation of other bis(3-indolyl)-dihydroxybenzoquinones, including isocochliodinol and neocochliodinol from *Chaetomium niuroum* and *C. amygaalisporum* (1983, "Isocochliodinol and Neocochliodinol, Bis(indolyl)-benzoquinones from Chaetomitrm spp.," *Chem. Pharm. Bull.* 31(9): 2998–3001).

Despite the therapeutic potential of cochliodinol and its derivatives, efficient methods suitable for large scale production of these compounds have remained elusive. U.S. Pat. No. 3,917,820 to Brewer et al. discloses the purple pigment cochliodinol and a process for its production by culturing various types of Chaetomium under aerobic conditions. However, the methods of Brewer require long incubation periods for cochliodinol production (2–8 days), the use of benzene, a known carcinogen, to effect chromatographic separation of cochliodinol from the culture and are limited to the few naturally occurring compounds. Moreover, Brewer discloses the isolation of only small quantities (0.75 grams) of cochliodinol from Chaetomiuim.

Another class of indolylquinones known as the asterriquinones in which the nitrogen of the indole ring is substituted, has been shown to exhibit antitumor activity. Arai et al. proposed the general name "asterriquinones" for the class of indolylquinones based upon asterriquinone (1981, "Metabolic Products of *Aspergillus terreus* IV. Metabolites of the Strain IFO 8835. (2) The Isolation and Chemical Structure of Indolyl Benzoquinone Pigments," *Chem. Pharm. Bull.* 29(4): 961–969). It should be noted that as used herein, the term "asterriquinone" has a more general meaning, and is used interchangeably with the term "indolylquinone." Yamamoto et al. disclose the antitumor activity of asterriquinone, i.e., 2,5-bis[N-(1",1"-dimethyl-2"-propenyl)indol-3'-yl]-3,6-dihydroxy-1,4-benzoquinone, and its isolation from the fungus *Aspergillus terreus* (1976, "Antitumor Activity of Asterriquinone, a Metabolic Product from *Aspergillus terreus,*" *Gann* 67:623–624).

Arai et al. disclose the isolation and characterization of 11 different kinds of bisindolyl-dimethoxyl-p-benzoquinones from *Aspergillus terreus*. Id. The isolation and structural determination of a number of other asterriquinones have also been reported. (Arai et al. 1981, "Metabolic Products of *Aspergillus terreus* VI. Metabolites of the Strain IFO 8835. (3) the Isolation and Chemical Structures of Colorless Metabolites," *Chem. Pharm. Bull.* 29(4): 1005–1012; Kaji et al., 1994, "Four New Metabolites of Aspergillus Terreus", *Chem. Pharm. Bull.* 42(8): 1682–1684). However, the separation of asterriquinones is troublesome because there are so many kinds of homologous pigments in the Aspergillis extracts. Moreover, the chromatographic purification of asterriquinones is typically carried out using benzene, a known carcinogen, as a solvent. Finally, only milligram quantities of asterriquinones have actually been isolated from these natural sources.

In view of their potential as anticancer agents, research has been directed to determination of the relationship between structure and antitumor activity of asterriquinones. For example, Arai et al. reported a study in which hydroxyl benzoquinone derivatives obtained by demethylation of bisindolyl-dimethoxyl-p-benzoquinones were found to have greater antitumor activity than the methoxyl derivatives (1981, "Metabolic Products of *Aspergilhis terreus* V. Demethylation of Asterriquinones," *Chem. Pharm. Bull.* 29(4): 991–999). Shimizu et al. noted that the presence of free hydroxyl groups in the benzoquinone moiety, as well the number and position of tert-, isopentenyl, or both pentyl groups, seems to have an effect on the antitumor activity of the compound (1982, "Antitumor Effect and Structure-Activity Relationship of Asterriquinone Analogs," *Gann* 73: 642–648). In an attempt to obtain information towards the development of more potent asterriquinone derivatives, Shimizu et al. conducted an investigation into the structure-activity relationship of asterriquinones in which the action mechanism of asterriquinone in its antitumor activity with reference to its interaction with DNA molecules and the plasma membrane of tumor cells was studied (1990, "Interaction of Asterriquinone with Deoxyribonucleic Acid in Vitro," *Chem. Pharm. Bull.* 38(9): 2617–2619). It was reported that a correlation exists between the pKa value of the asterriquinone derivative and its antitumor activity. Id. Maximum antitumor activity was observed for compounds with pKa's in the range of 6–7. Id.

Analysis of structure-activity relationships has led to attempts to obtain compounds with more potent antitumor activity by chemical modification of asterriquinone and related compounds isolated from natural sources (Shimizu et al., 1982, "Antitumor Activity of Asterriquinones from Aspergillus Fungil IV. An Attempt to Modify the Structure of Asterriquinones to Increase the Activity," *Chem. Pharm. Bull.* 30(5): 1896–1899). Although benzoquinone derivatives having aziridinyl groups in the molecule such as mitomycin C, carbazilquinone or "E 39" are well known potent anticancer agents, replacement of the functional groups at the 3 and 6 positions in the benzoquinone moiety of asterriquinone failed to enhance its antitumor potency. Id. Similarly, the introduction of an ethyleneimino group into the molecule did not increase antitumor activity. A dimethylallyl derivative of asterriquinone showed moderate activity against the ascites and solid tumors of Ehrlich carcinoma, while an allyl derivative did not. It was suggested that in order to enhance the antitumor activity, it may be necessary not only to alter the pKa value by alkylation, but also to introduce hydrophilic groups into the molecule.

In addition to their demonstrated antitumor activity, asterriquinone and some of its analogues have also been shown to be strong inhibitors of HIV-reverse transcriptase (Ono et al., 1991, "Inhibition of HIV-Reverse Transcriptase Activity by Asterriquinone and its Analogues," *Biochem. Biophys. Res. Commun.* 174(1): 56–62).

2.2 Protein Phosphorylation and Signal Transduction

Cells receive signals from their environment through the binding of extracellular molecules to the cell surface. These extracellular signals are essential for the correct regulation of such diverse cellular processes as proliferation, differentiation, chemotaxis, contractility, secretion, contact inhibition, cell survival, neurite outgrowth and metabolism, in particular, the metabolism of glucose. The extracellular molecules, which can be, inter alia, hormones such as insulin, growth factors, lymphokines, or neurotransmitters, are ligands that bind to the extracellular domains of specific cell surface receptors. The binding of these ligands to their receptors triggers cascades of reactions that bring about both the amplification of the original stimulus and the coordinate regulation of cellular processes. In addition to normal cellular processes, receptors and their extracellular ligands may be involved in abnormal or potentially deleterious processes such as virus-receptor interaction, inflammation and cellular transformation to cancerous states. In addition, it is believed that impaired insulin-stimulated glucose uptake observed in diabetic patients may be associated with altered insulin receptor signal transduction. Goodyear et al., 1995, *J. Clin. Invest.* 95:2195–2204.

A central feature of this signaling process, known as signal transduction, is the reversible phosphorylation of certain proteins. The phosphorylation or dephosphorylation of amino acid residues triggers conformational changes in regulated proteins that alter their biological properties. Proteins are phosphorylated by protein kinases and are dephosphorylated by protein phosphatases. Protein kinases and phosphatases are classified according to the amino acid residues they act on, with one class being serine-threonine kinases and phosphatases (reviewed in Scott, J. D. and Soderling, T. R., 1992, 2:289–295), which act on serine and threonine residues, and the other class being the tyrosine kinases and phosphatases (reviewed in Fischer, E. H. et al., 1991, *Science* 253:401–406; chlessinger, J. and Ullrich, A., 1992, *Neuron* 9:383–391; Ullrich, A. and Schlessinger, J., 1990, *Cell* 61:203–212), which act on tyrosine residues. The protein kinases and phosphatases may be further defined as being receptors, i.e., the enzymes are an integral part of a transmembrane, ligand-binding molecule, or as non-receptors, meaning they respond to an extracellular molecule indirectly by being acted upon by a ligand-bound receptor. Phosphorylation is a dynamic process involving competing phosphorylation and dephosphorylation reactions, and the level of phosphorylation at any given instant reflects the relative activities, at that instant, of the protein kinases and phosphatases that catalyze these reactions.

The importance of protein tyrosine phosphorylation in growth factor signal transduction, cell cycle progression and neoplastic transformation is now well established (Cantley, L. C. et al., 1991, *Cell* 64:281–302; Hunter, T., 1991, *Cell* 64:249–270; Nurse, 1990, *Nature* 344:503–508; Schlessinger, J. and Ullrich, A., 1992, *Neuron* 9:383–391; Ullrich, A. and Schlessinger, J., 1990, *Cell* 61:203–212). Subversion of normal growth control pathways leading to oncogenesis has been shown to be caused by activation or over-expression of protein tyrosine kinases which constitute a large group of dominant oncogenic proteins (reviewed in Hunter, T., 1991, *Cell* 64:249–270).

2.3 Protein Tyrosine Kinases

2.3.1. Receptor-Type Protein Tyrosine Kinases

Many cellular functions are mediated by the binding of growth factor ligands to membrane-bound protein tyrosine kinase ("PTK") receptors. Receptor-type protein tyrosine kinases having transmembrane topology have been studied extensively. The binding of certain ligands to the extracellular domain of a receptor protein tyrosine kinase is thought to induce dimerization of the receptor, resulting in the reversible auto-phosphorylation of receptor tyrosine residues within the intracellular domain of the tyrosine kinase. These individual phosphotyrosine residues may then serve as specific binding sites for a host of cytoplasmic signaling molecules, thereby activating various signal transduction pathways (Ullrich A., and Schlessinger, J., 1990, *Cell* 61:203–212).

The mechanism by which insulin receptor transmits signals to the interior of the cell upon insulin binding it slightly different. The insulin receptor is a disulfide-linked heterotetramer ($\alpha_2\beta_2$). Therefore, it does not dimerize upon insulin binding. Rather, insulin interaction with the extracellular portion of the insulin receptor causes a conformational change in the receptor that in turn causes the intracellular tyrosine kinases to become phosphoylated. As in the case with PTK receptors that dimerize, the individual phosphotyrosine residues may serve as binding sites for other molecules in the insulin signaling cascade.

2.3.2. Non-Receptor-Type Protein Tyrosine Kinases

The intracellular, cytoplasmic, non-receptor protein tyrosine kinases, may be broadly defined as those protein tyrosine kinases which do not contain a hydrophobic, transmembrane domain. Within this broad classification, one can divide the known cytoplasmic protein tyrosine kinases into eleven distinct morphotypes, including the SRC family, the FES family, the ABL family, the $Za_p$ 70 family and the JAK family. While distinct in their overall molecular structure, members of these morphotypic families of cytoplasmic protein tyrosine kinases may share non-catalytic domains in addition to sharing their catalytic kinase domains. Such non-catalytic domains include the SH2 and SH3 domains. These non-catalytic domains are thought to be important in the regulation of protein—protein interactions during signal transduction (Pawson, T. and Gish, G., 1992, *Cell* 71:359–362).

While the metabolic roles of cytoplasmic protein tyrosine kinases are less well understood than that of the receptor-type protein tyrosine kinases, significant progress has been made in elucidating some of the processes in which this class of molecules is involved. For example, members of the src family, lck and fyn, have been shown to interact with CD4/CD8 and the T cell receptor complex, and are thus implicated in T cell activation, (Veillette, A. and Davidson, D., 1992, *TIG* 8:61–66), certain cytoplasmic protein tyrosine kinases have been linked to certain phases of the cell cycle (Morgan, D. O. et al., 1989, *Cell* 57: 775–786; Kipreos, E. T. et al., 1990, *Science* 248: 217–220; Weaver et al., 1991, *Mol. Cell. Biol.* 11:4415–4422), and cytoplasmic protein tyrosine kinases have been implicated in neuronal development (Maness, P., 1992, *Dev. Neurosci* 14:257–270). Deregulation of kinase activity through mutation or over-expression is a well-established mechanism underlying cell transformation (Hunter et al., 1985, stipra; Ullrich et al., supra).

2.4 Adaptor Proteins

Adaptor proteins are intracellular proteins having characteristic conserved peptide domains (SH2 and/or SH3 domains, as described below) which are critical to the signal transduction pathway. Such adaptor proteins serve to link protein tyrosine kinases, especially receptor-type protein tyrosine kinases to downstream intracellular signaling pathways such as the RAS signaling pathway. It is thought that such adaptor proteins may be involved in targeting signal transduction proteins to the correct site in the plasma membrane or subcellular compartments, and may also be involved in the regulation of protein movement within the cell.

Such adaptor proteins are among the protein substrates of the receptor-type protein tyrosine kinases, and have in common one or two copies of an approximately 100 amino acid long motif. Because this motif was originally identified in c-Src-like cytoplasmic, non-receptor tyrosine kinases it is referred to as a Src homology 2 (SH2) domain. SH2-containing polypeptides may otherwise, however, be structurally and functionally distinct from one another (Koch, C. A. et al., 1991, *Science* 252:668–674). SH2 domains directly recognize phosphorylated tyrosine amino acid residues. The peptide domains also have independent sites for the recognition of amino acid residues surrounding the phosphotyrosine residue(s).

When a receptor protein tyrosine kinase binds an extracellular ligand, receptor dimerization is induced, which, in turn, leads to intermolecular autophosphorylation of the dimerized kinases (Schlessinger, J. and Ullrich, A., 1992, *Neuron* 9: 383–391). Receptor phosphorylation, therefore, creates SH2-binding sites, to which an adaptor protein may bind.

SH2 domains represent recognition motifs for specific tyrosine-phosphorylated peptide sequences and are usually accompanied by another conserved domain of 50–75 amino acid residues, known as the SH3 domain. The current view is that SH3 domains function, in part, as protein-binding from the cell surface that act to link signals transmitted from the cell surface to downstream effector genes such as ras (Pawson, T. and Schlesinger, J., 1993 *Current Biology*, 3:434–442).

On the basis of their primary structures, it is possible to divide SH-2 containing proteins into two main classes: Type I and Type II. (Schlessinger, J., and Ullrich, A, 1992, *Neuron* 9:383–391). Type I defines SH-2 containing have distinct enzymatic activities, such as phospholipase activity, tyrosine kinase activity, and putative GDP-GTP exchange functions. Proteins of this class are thought to exert their enzymatic activities and transmit signals upon tyrosine phosphorylation or by interacting with neighboring target proteins.

Type II SH-2 containing proteins are adaptor proteins that are composed of virtually only SH-2 and SH-3 domains. Mammalian growth factor receptor-binding protein 2 (GRB-2) is a 26 kilodalton member of the type II SH-2 containing proteins that has one SH-2 domain flanked by two SH-3 domains (Lowenstein et al., 1992, *Cell* 70:43–442). The GRB-2 adaptor protein binds to tyrosine-phosphorylated growth factor receptors through its SH-2 domain and to, inter alia, proline-rich regions of the son of sevenless (SOS) guanine nucleotide exchange factor through its SH-3 domains (Buday, L. and Dowvnward, J., 1993, *Cell* 73:611–620; Egan, S. E. et al., 1993, *Nature* 363:45–51; Li, N. et al., 1993, *Nature* 363:85–87; Gale, N. W. et al., 1993, *Nature* 363:88–92; Rozakis-Adcock et al., 1993, *Nature* 363:83–85; Chardin, P. et al., 1993, *Science* 260:1338–1343; Oliver, J. P. et al., *Cell* 73:179–191; Simon, M. A. et al., 1993, *Cell* 73:169–177). Therefore, binding of GRB-2 to the receptor kinases, allows for the recruitment of SOS to the plasma membrane, where Ras, a guanine-nucleotide binding signaling protein, is located (Schlessinger, J., 1993, *TIBS* 18:273–275). As a result of the recruitment of SOS to the inner cell membrane by GRB-2 upon growth factor receptor tyrosine phosphorylation, the active GTP bound form of Ras accumulates for downstream signaling (Gibbs, J. B. et al., 1990, *J. Biol. Chem.* 265:20437–2044; Satoh, T. et al., 1990, *Proc. Natl. Acad. Sci. USA* 87:5993–5997; Li, B. -Q. et at., 1992, *Science* 256:1456–1459; Buday, L. and Downward, J., 1993, *Mol. Cell. Biol.* 13:1903–1910; Medema, R. H. et al., 1993, *Mol. Cell. Biol.* 13:155–162).

2.5 Cell Proliferative Disorders

Growth factors and their receptors are crucial for normal cellular functions but can also act as oncogenes leading to cell transformation, oncogenesis, and cell proliferative disorders, including cancer. Activation of the oncogenic potential of normal cellular proteins may occur, e.g., by the uncoupling of the binding of the extracellular ligand to its receptor and the intracellular cascade of reactions, by alteration of the enzymatic activity of signaling proteins, or by inappropriate binding of signaling proteins to cellular components.

For example, it is known that the BCR-ABL oncoprotein is involved in the pathogenesis of leukemias, such as Philadelphia chromosome-positive human leukemia. BCR-ABL exhibits regulated tyrosine kinase activity that is not regulated by the binding of a ligand. It has recently been demonstrated (Pendergast, A. M. et al., 1993, *Cell* 75:175–185) that a tyrosine-phosphorylated region of the BCR-ABL binds the SH-2 domain of GRB-2, and that this interaction activates the Ras signaling pathway.

Thus, there are multiple events which occur along a signal transduction pathway which appear to be required for the ultimate appearance of a cell proliferative disorder such as the form of leukemia described above. One approach to the treatment of oncogenenic, cell proliferative disorders would be to attempt to "short circuit" abnormal signal transduction events which contribute to the appearance of such disorders, by interfering with one or more of these requisite events.

The amelioration of abnormal signal transduction events leading to cell proliferative disorder symptoms may be accomplished by, e.g., targeting and directly inhibiting the interactions of proteins in the signal transduction pathway. For example, in instances wherein the signal transduction event of interest involves an adaptor protein/protein tyrosine kinase interaction, the inhibition of such interactions may lead to the amelioration of cell proliferative disorder symptoms. The utility of this approach has been demonstrated using expression of signaling incompetent proteins in cells. For example, cells expressing a mutant form of Bcr-Abl which lacks the tyrosine residue necessary for binding of the GRB-2 SH2 domain, and which is thus signaling incompetent, no longer exhibit a transformed phenotype (RER) (Pendergast et al., supra).

However, there are many signal transduction proteins that contain at least one SH2 domain, and therefore, compounds that are not specific for a particular SH2-containing protein will shut down signal transduction pathways indiscriminately. If these non-specific compounds were administered to a subject suffering from a cell proliferative disorder, they might be toxic to the subject or cause side effects associated with shutting down numerous signal transduction pathways. Therefore, it is desirable to have compounds that are specific for one type of interaction, e.g. the GRB-2 SH2-phosphotyrosine or the GRB-2 SH3-polyproline interaction. The specific interference of the binding of GRB-2 with either an activated tyrosine kinase or a downstream protein could result in blocking an abnormal signal transduction pathway at a fairly early stage without blocking other pathwvays that rely on the interaction of other SH2-containing proteins with phosphotyrosine.

2.6 Diabetes Mellitus

Diabetes mellitus is a group of syndromes characterized by hyperglycemia, altered metabolism of lipids, carbohydrates, and proteins, and an increased risk of complications from vascular disease. There are two main types of diabetes mellitus: insulin-dependent diabetes mellitus (IDDM or Type I diabetes) and non-insulin-dependent diabetes mellitus (NIDDM or Type II diabetes). Insulin is a peptide hormone produced by the body that stimulates glucose uptake by cells, lipogenesis, and other general anabolic effects. Virtually all forms of diabetes mellitus are due to a decrease in the circulating concentration of insulin and a decrease in the response of peripheral tissues to insulin.

Insulin is responsible for maintaining glucose homeostasis in the body. When there is an excess of glucose in the body, or when tissues require fuel, insulin is released and binds to its protein tyrosine kinase receptor. The conformational change in the receptor resulting from insulin binding causes tyrosine phosphorylation of the insulin receptor intracellular tyrosine kinases. This in turn begins a signal transduction cascade that ultimately results in uptake of glucose by the cells. Depending on the type of cell, the glucose can be metabolized or stored as fat or glycogen for later use when needed, e.g., during starvation.

Insulin therapy is currently the most effective treatment of virtually all IDDM and many NIDDM patients. Human, porcine, bovine, or a mixture of porcine and bovine insulin are used in therapeutic preparations. Insulin cannot be administered orally because the protein is digested in the stomach. Rather, insulin must be administered intravenously, intramuscularly, or preferably, subcutaneously. Insulin injection differs from normal secretion of insulin in two major ways: the kinetics do not mimic the normal rapid rise and decline of insulin secretion in response to ingestion of nutrients, and the insulin diffuses into the peripheral circulation instead of being released into the portal circulation, thus eliminating the preferential effect of secreted insulin on hepatic metabolic processes. Insulin must be purified and supplied in a pharmaceutically acceptable carrier or diluent and is only stable for a few days. Thus, in addition to not ideally mimicking physiological insulin production, insulin therapy is also relatively expensive and inconvenient.

Diabetic patients suffer from a variety of disorders due to prolonged exposure of tissues to elevated concentrations of glucose, including premature atherosclerosis, intercapillary glomerulosclerosis, retinopathy, neuropathy and ulceration and gangrene of the extremities. Moreover, insulin therapy itself causes side effects, including hypoglycemia, insulin allergy and resistance, lipoatrophy at the site of insulin injection, lipohyperatrophy at sites of high insulin concentration, and insulin edema.

Because of the problems associated with insulin therapy, research effort has focused on finding alternative therapies for diabetes, and in particular the development of oral hypoglycemic agents. Oral hypoglycemic agents currently in use include the class of compounds known as the sulfonylureas, which act by stimulating insulin release from pancreatic cells, and the biguanides, which increase insulin action in peripheral tissues and reduce hepatic glucose output due to inhibition of gluconeogenesis. In addition, α-glucosidase inhibitors such as acarbose, which reduce intestinal absorption of carbohydrates, are also administered orally in the treatment of diabetes. However, there are many side effects associated with these oral hypoglycemic agents, including nausea and vomiting, cholestatic jaundice, agranulocytosis, aplastic and hemolytic anemias, generalized hypersensitivity reactions, and dermatological reactions associated with sulfonylureas; diarrhea, abdominal discomfort, nausea, metallic taste and anorexia associated with biguanides; and malabsorption, flatulence, and abdominal bloating associated with α-glucosidase inhibitors.

Thus, in view of the serious drawbacks associated with the current therapies for diabetes mellitus, there is a need in the art for an effective treatment for diabetes, which does not involve the inconvenience of insulin injection, or the side effects caused by existing oral hypoglycemic drugs used to treat diabetes. Therefore, there remains a need in the art for a method of controlling diabetes that is convenient, effective, inexpensive, and without major side effects.

3. Summary of the Invention

The present invention relates to methods and compositions for inhibition of cell signal transduction associated with cell proliferative disorders. Specifically, the present invention relates to particular indolylquinone compounds, and methods for using such compounds. In a preferred embodiment, the compounds of the invention inhibit the interaction of protein tyrosine kinases with the GRB-2 adaptor protein, resulting in inhibition and suppression of tumor growth. Thus, the compounds of the present invention are useful in the treatment of cancers involving solid tumors, and in particular, the inhibition and reversal of tumor growth.

The compounds of the present invention are described by the formula I below:

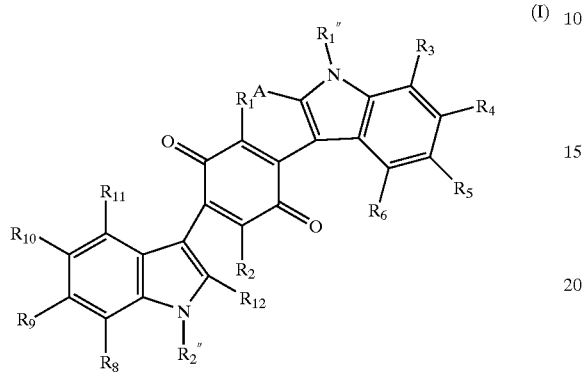

(I)

or a pharmaceutically acceptable salt thereof, wherein:
A is monocyclic aryl, bicyclic aryl or heteroaryl;
$R_1$ and $R_2$ are each independently Br, Cl, F, I, H, OH, or —OCOR, wherein R is lower alkyl, aryl or alkylaryl;
$R_1''$ and $R_2''$ are each independently H, $C_1$–$C_7$ alkyl, $C_2$–$C_7$ alkenyl, $C_2$–$C_7$ alkynyl, arylalkyl or aryl; and
$R_3$ to $R_6$ and $R_8$ to $R_{12}$ are each independently hydrogen, branched or unbranched $C_1$–$C_n$ alkyl, alkylcarboxy, $C_2$–$C_m$ alkenyl, $C_2$–$C_m$ alkynyl, alkenylcarboxy, monocyclic aryl, bicyclic aryl, heteroaryl, alkylaryl, hydroxy, hydroxyalkyl, $C_1$–$C_n$ alkoxy, nitro, halo, trihalomethyl, amido, carboxamido, carboxy, sulfonyl, sulfonamido, amino, mercapto, or 2-methylbut-2-en-4-yl, wherein n is an integer from 0 to 12, preferably 1–7, and m is an integer from 0 to 12, preferably 1–7.

Preferred compounds of the present invention are described by the formula II, below:

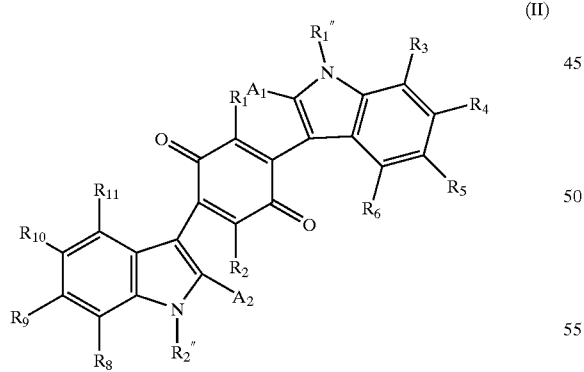

(II)

or a pharmaceutically acceptable salt thereof, wherein:
$A_1$ and $A_2$ are each individually carboxy, monocyclic aryl, bicyclic aryl or heteroaryl;
$R_1$ and $R_2$ are each independently Br, Cl, F, I, H, OH, or —OCOR, wherein R is lower alkyl, aryl or alkylaryl;
$R_1''$ and $R_2''$ are each independently H, $C_1$–$C_7$ alkyl, $C_2$–$C_7$ alkenyl, $C_2$–$C_7$ alkynyl, arylalkyl or aryl; and
$R_3$ to $R_6$ and $R_8$ to $R_{11}$ are each independently hydrogen, branched or unbranched $C_1$–$C_n$ alkyl, alkylcarboxy, $C_2$–$C_m$ alkenyl, $C_2$–$C_m$ alkynyl, alkenylcarboxy, aryl, alkylaryl, hydroxy, hydroxyalkyl, $C_1$–$C_n$ alkoxy, nitro, halo, trihalomethyl, amido, carboxamido, carboxy, sulfonyl, sulfonamido, amino, mercapto, or 2-methylbut-2-en-4-yl, wherein n is an integer from 0 to 12, preferably 1–7, and m is an integer from 0 to 12, preferably 1–7.

Preferred compounds of the present invention are compounds of formula I wherein A is:

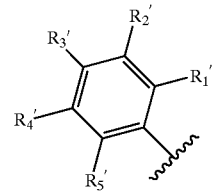

wherein $R_1'$ to $R_5'$ are each independently hydrogen, branched or unbranched $C_1$–$C_n$ alkyl alkylcarboxy, $C_2$–$C_m$ alkenyl, $C_2$–$C_m$ alkynyl, alkenylcarboxy, aryl, alkylaryl, hydroxy, hydroxyalkyl, $C_n$–$C_1$ alkoxy, nitro, halo, trihalomethyl, amido, carboxamido, carboxy, sulfonyl, sulfonamido, amino, mercapto, or 2-methylbut-2-en-4-yl, wherein n is an integer from 0 to 12, preferably 1–7, and m is an integer from 0 to 12, preferably 1–7.

or

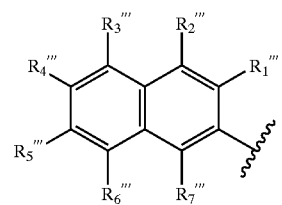

wherein $R_1'''$ to $R_7'''$ are each independently hydrogen, branched or unbranched $C_1$–$C_n$ alkyl, alkylcarboxy, $C_2$–$C_m$ alkenyl, $C_2$–$C_m$ alkynyl, alkenylcarboxy, aryl, alkylaryl, hydroxy, hydroxyalkyl, $C_1$–$C_n$ alkoxy, nitro, halo, trihalomethyl, amido, carboxamido, carboxy, sulfonyl, sulfonamido, amino, mercapto, or 2-methylbut-2-en-4-yl, wherein n is an integer from 0 to 12, preferably 1–7, and m is an integer from 0 to 12, preferably 1–7.

In preferred embodiments, $R_1'$ to $R_5'$ are H, and $R1'''$ to $R_7'''$ are H.

Preferred compounds of the present invention also include compounds of formula II wherein $A_1$ and $A_2$ are each independently

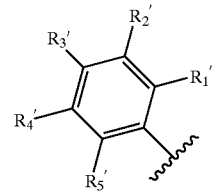

wherein $R_1'$ to $R_5'$ are each independently hydrogen, branched or unbranched $C_1$–$C_n$ alkyl, alkylcarboxy, $C_2$–$C_m$ alkenyl, $C_2$–$C_m$ alkynyl, alkenylcarboxy, aryl, alkylaryl, hydroxy, hydroxyalkyl, $C_1$–$C_n$ alkoxy, nitro, halo, trihalomethyl, amido, carboxamido, carboxy, sulfonyl, sulfonamido, amino, mercapto, or 2-methylbut-2-en-4-yl, wherein n is an integer from 0 to 12, preferably 1–7, and m is an integer from 0 to 12, preferably 1–7;

or

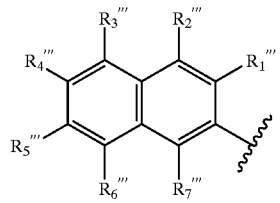

wherein $R_1'''$ to $R_7'''$ are each independently hydrogen, branched or unbranched $C_1$–$C_n$ alkyl, alkylcarboxy, $C_2$–$C_m$ alkenyl, $C_2$–$C_m$ alkynyl, alkenylcarboxy, aryl, alkylaryl, hydroxy, hydroxyalkyl, $C_1$–$C_n$ alkoxy, nitro, halo, trihalomethyl, amido, carboxamido, carboxy, sulfonyl, sulfonamido, amino, mercapto, or 2-methylbut-2-en-4-yl, wherein n is an integer from 0 to 12, preferably 1–7, and m is an integer from 0 to 12, preferably 1–7.

In preferred embodiments, $R_1'$ to $R_5'$ are H, and $R1'''$ to $R_7'''$ are H.

In addition, the present invention encompasses a pharmaceutical composition comprising a compound of the formula I or formula II, or a pharmaceutically acceptable salt thereof, and methods for using a compound or pharmaceutical composition of the invention in an animal. Preferably, the animal is a mammal, and most preferably, a human. In particular, the present invention encompasses a method for ameliorating the symptoms of a cell proliferative disorder. In some embodiments, the cell proliferative disorder involves an interaction between GRB-2 and protein tyrosine kinase, comprising administering a therapeutically effective amount of a compound of formula I or formula II, or a pharmaceutically acceptable salt thereof. The present invention also encompasses a method for ameliorating the symptoms of a cell proliferative disorder, wherein the cell proliferative disorder involves an interaction between GRB-2 adaptor proteins and protein tyrosine kinases, comprising administering a pharmaceutical composition comprising a compound of formula I or formula II. The present invention is based, in part, on the inventors' discovery that the disclosed compounds inhibit interactions of the GRB-2 adaptor protein with phosphorylated tyrosine kinases, thereby interrupting the cascade of cellular events which can lead to the development of cancer. Thus, the present invention also relates to methods for ameliorating symptoms of cell proliferative disorders associated with GRB-2 adaptor protein function, comprising administering an effective amount of a compound of formula I or formula II, or a pharmaceutical composition comprising a compound of formula I or formula II. The invention encompasses methods for treating a cell proliferative disorder. In certain embodiments, the cell proliferative disorder involves a protein tyrosine kinase/GRB-2 adaptor polypeptide complex. In some embodiments, the cell proliferative disorder involves an interaction between GRB-2 and tyrosine kinase.

The present invention also provides a method for ameliorating the symptoms of a cell proliferative disorder, comprising administering a therapeutically effective amount of a compound of the formula III below:

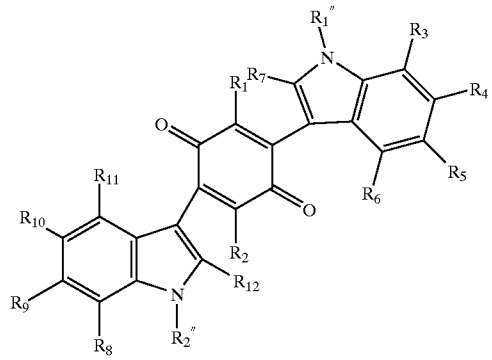

or a pharmaceutically acceptable salt, wherein:
$R_1$ and $R_2$ are each independently Br, Cl, F, I, H, OH, or —OCOR, wherein R is lower alkyl, aryl or alkylaryl;
$R_1''$ and $R_2''$ are each independently H, $C_1$–$C_7$ alkyl, $C_2$–$C_7$ alkenyl, $C_2$–$C_7$ alkynyl, arylalkyl or aryl; and
$R_3$ to $R_{12}$ are each independently hydrogen, branched or unbranched $C_1$–$C_n$ alkyl, alkylcarboxy, $C_2$–$C_m$ alkenyl, $C_2$–$C_m$ alkynyl, alkenylcarboxy, aryl, alkylaryl, hydroxy, hydroxyalkyl, $C_1$–$C_n$ alkoxy, nitro, halo, trihalomethyl, amido, carboxamido, carboxy, sulfonyl, sulfonamido, amino, mercapto, or 2-methylbut-2-en-4-yl, wherein n is an integer from 0 to 12, preferably 1–7, and m is an integer from 0 to 12, preferably 1–7.

In addition, the present invention encompasses method of ameliorating the symptoms of a cell proliferative disorder, wherein the cell proliferative disorder involves an interaction between GRB-2 and a tyrosine kinase, which comprises administering a therapeutically effective amount of a pharmaceutical composition comprising a compound of formula III.

The present invention further comprises a method for ameliorating the symptoms of a cell proliferative disorder. In particular embodiments, the cell proliferative disorder involves an interaction between GRB-2 and tyrosine kinase, comprising administering a therapeutically effective amount of a compound of the formula (IV):

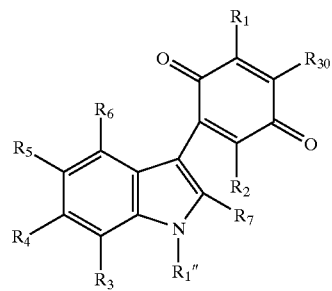

or a pharmaceutically acceptable salt thereof, wherein:
$R_1$, $R_2$ and $R_{30}$ are each independently Br, Cl, F, I, H, OH or —OCOR, wherein R is lower alkyl, aryl or alkylaryl;
$R_1''$ is H, $C_1$–$C_7$ alkyl, $C_2$–$C_7$ alkenyl, $C_2$–$C_7$ alkynyl, arylalkyl or aryl; and
$R_3$ to $R_7$ are each independently hydrogen, branched or unbranched $C_1$–$C_n$ alkyl, alkylcarboxy, $C_2$–$C_m$ alkenyl, alkynyl, alkenylcarboxy, aryl, alkylaryl, hydroxy, hydroxyalkyl, $C_1$–$C_n$ alkoxy, nitro, halo, trihalomethyl, amido, carboxamido, carboxy, sulfonyl, sulfonamido, amino, mercapto, or 2-methylbut-2-en-4-yl, wherein n is an integer from 0 to 12 and m is an integer from 0 to 12.

The present invention also encompasses a method of ameliorating the symptoms of a cell proliferative disorder comprising administering an effective amount of a pharmaceutical composition comprising a compound formula IV. The invention also relates to a method of inhibiting interactions between GRB-2 and tyrosine kinases, comprising administering an effective amount of a compound of formula III, a compound of formula IV, a pharmaceutical composition comprising a compound of formula III, or a pharmaceutical composition comprising a compound of formula IV.

In another aspect, the present invention relates to methods for treating insulin-related disorders, including, but not limited to diabetes, insulin resistence, insulin deficiency and insulin allergy, which comprise administering to a patient a therapeutically effective amount of a compound of formula I, formula II, formula III, or formula IV or a therapeutically effective amount of a pharmaceutical composition comprising a compound of formula I, formula II, formula III, or formula IV. It has been discovered that the compounds of formulae I, II, III and IV have a hypoglycemic effect when administered to an animal, and are thus effective for treating the symptoms of insulin deficiency and insulin resistance in animals.

In particular, the present invention encompasses a method for treating diabetes or ameliorating the symptoms of diabetes comprising administering a therapeutically effective amount of a compound of formula I, II or III, or a pharmaceutically acceptable salt thereof. Administration of the compounds of formula I, II or III to a patient results in a lowering of the blood glucose level of the patient. Thus, the present invention encompasses a method of lowering the blood glucose level in an animal, comprising administering an effective amount of a compound of formula I, II or III, or a pharmaceutical composition comprising a compound of formula I, II or III. Without limiting the present invention to any particular mechanism of action to explain the hypoglycemic effect of the compounds of formulae I, II and III, it is believed that these compounds mimic the action of insulin in the body. In particular, it is believed that the compounds of the invention activate the insulin receptor tyrosine kinase in an animal, thereby triggering a cascade of cellular events leading to glucose uptake. Thus, the present invention also relates to a method of stimulating insulin receptor tyrosine kinase activity in an animal, comprising administering an effective amount of a compound of formula I, II or III.

The present invention encompasses methods for the treatment of both insulin-dependent or type I diabetes (formerly termed juvenile-onset of ketosis-prone diabetes) and non-insulin-dependent or type II diabetes (formerly termed adult-onset, maturity-onset or nonketotic diabetes). The methods of the present invention are suitable for treatment of mammals for veterinary use, or in humans for clinical uses. The invention relates to methods for treating and ameliorating the symptoms of insulin deficiency and other insulin disorders in an animal. The methods of the present invention are suitable for the treatment and amelioration of symptoms caused by a deficiency in insulin, or due to malfunctioning insulin-stimulated signal transduction leading to glucose uptake. In the case of insulin deficiency, the compounds described herein mimic the effects of insulin through interaction with insulin receptor kinase, thereby triggering the cascade of events resulting in glucose uptake and metabolism. Since the compounds of the invention stimulate and/or activate the insulin receptor protein tyrosine kinase, the methods of the invention are useful in the treatment of diabetic patients who do not produce enough insulin, and in diabetic patients who may produce insulin, but who are resistant to insulin.

In another aspect the present invention provides a method for the synthesis of indolylquinones which comprises reacting a substituted or unsubstituted 2,5-dihalo-1,4-benzoquinone with one or more substituted or unsubstituted indoles in a polar organic solvent and in the presence of metal carbonate.

In one embodiment, the present invention provides a method for preparing a symmetrical indolylquinone compound of the formula V:

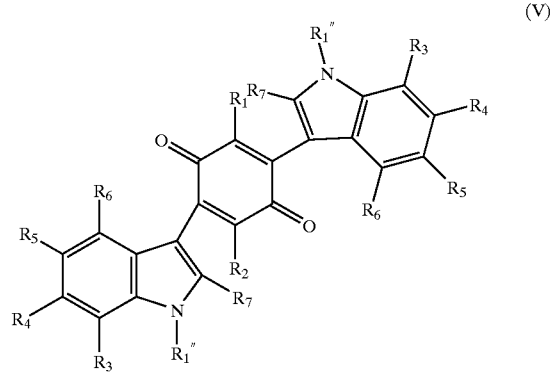

(V)

wherein:

$R_1$ and $R_2$ are each independently Br, Cl, F, I, H, OH or —OCOR, wherein R is, lower alkyl, aryl or alkylaryl;

$R_1''$ is H, $C_1$–$C_7$ alkyl, $C_2$–$C_7$ alkenyl, $C_2$–$C_7$ alkynyl, arylalkyl or aryl; and $R_3$ to $R_7$ are each independently hydrogen, branched or unbranched $C_1$–$C_n$ alkyl, alkylcarboxy, $C_2$–$C_m$ alkenyl, $C_2$–$C_m$ alkynyl, alkenylcarboxy, aryl, alkylaryl, hydroxy, hydroxyalkyl, $C_1$–$C_n$ alkoxy, nitro, halo, trihalomethyl, amido, carboxamido, carboxy, sulfonyl, sulfonamido, amino, mercapto, or 2-methylbut-2-en-4-yl, wherein n is an integer from 0 to 12, preferably 1–7, and m is an integer from 0 to 12, preferably 1–7.

$R_1$ and $R_2$ are preferably Br, Cl, F, H or OH.

The method comprises reacting a substituted or unsubstituted 2,5-dihalo-1,4-benzoquinone, preferably a 2,5-dibromo-1,4-benzoquinone compound of the formula VI:

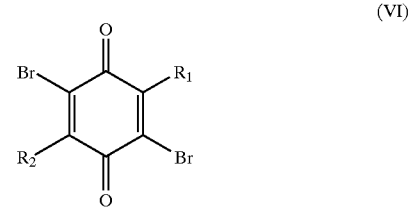

(VI)

wherein $R_1$ and $R_2$ are as defined above; with at least one indole of the formula VII:

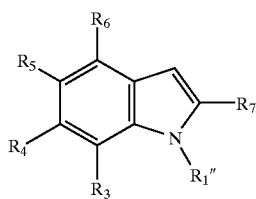

(VII)

wherein $R_1''$ and $R_3$–$R_7$ are as defined above. The reaction is carried out in a polar organic solvent and in the presence of metal carbonate under mild conditions which are further discussed below.

The method may further comprise reacting the indolylquinone compound of formula V with an alkali metal hydroxide to produce a compound of the formula V, wherein $R_1$ and $R_2$ are OH.

Further, the method may further comprise reacting the indolylquinone compound of formula V wherein $R_1$ and $R_2$ are Br, with an alkali metal hydroxide and an alcohol of the formula R'OH, wherein R' is lower alkyl or alkylaryl, to produce an indolylquinone compound of the formula V, wherein $R_1$ is $OR_1'$ and $R_2$ is $OR_2'$ wherein $R_1'$ and $R_2'$ are each independently lower alkyl or alkylaryl.

In another embodiment, the present invention provides a method for preparing an indolylquinone compound of the formula III, which comprises:

(a) reacting a substituted or unsubstituted 2,5-dibromo-1,4-benzoquinone compound of the formula VI:

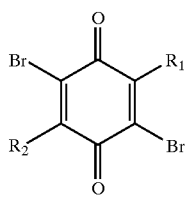

(VI)

wherein $R_1$ and $R_2$ are as defined above; with one equivalent of a first indole of the formula VII:

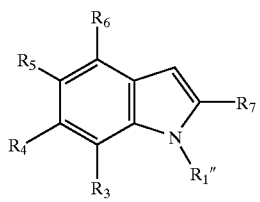

(VII)

wherein $R_1''$ and $R_3$–$R_7$ are as defined above; in a polar organic solvent and in the presence of metal carbonate;

(b) reacting the intermediate product of step (a) with one equivalent of a second indole of the formula VIII:

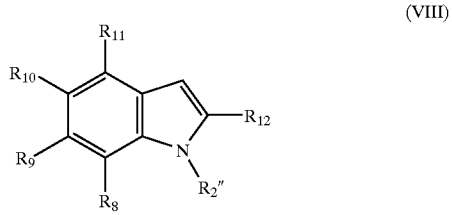

(VIII)

wherein $R_2''$ and $R_8$–$R_{12}$ are as defined above. Both reactions are carried out in a polar organic solvent and in the presence of metal carbonate under mild conditions which are further discussed below.

The invention also encompasses further reacting the indolylquinone compound of formula III with an alkali metal hydroxide to produce a compound of the formula III wherein $R_1$ and $R_2$ are OH.

Further, the invention encompasses reacting the indolylquinone of formula III wherein $R_1$ and $R_2$ are Br, F, Cl or I, with an alkali metal hydroxide and an alcohol of the formula R'OH, wherein R' is lower alkyl or alkylaryl, to produce an indolylquinone compound of the formula III, wherein $R_1$ is $OR_1'$, and $R_2$ is $OR_2'$, wherein $R_1'$ and $R_2'$ are each independently lower alkyl, aryl or alkylaryl.

In another embodiment, the present invention provides a method for preparing a mono-indolylquinone compound of the formula IV:

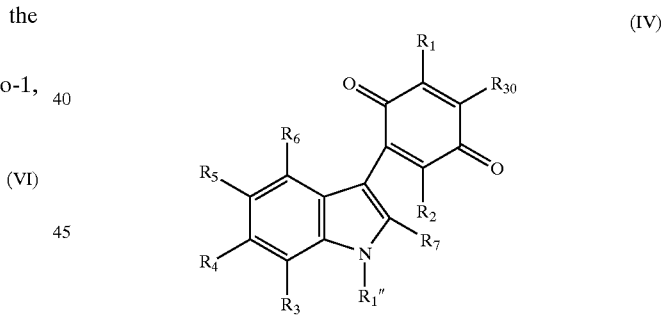

(IV)

wherein:

$R_1$, $R_2$ and $R_{30}$ are each independently Br, Cl, F, I, H, OH or —OCOR, wherein R is lower alkyl, aryl or alkylaryl;

$R_1''$ is H, $C_1$–$C_7$ alkyl, $C_2$–$C_7$ alkenyl, $C_2$–$C_7$ alkynyl, arylalkyl or aryl; and $R_3$ to $R_7$ are each independently hydrogen, branched or unbranched $C_1$–$C_n$ alkyl, alkylcarboxy, $C_2$–$C_m$ alkenyl, alkynyl, alkenylcarboxy, aryl, alkylaryl, hydroxy, hydroxyalkyl, $C_1$–$C_n$ alkoxy, nitro, halo, trihalomethyl, amido, carboxamido, carboxy, sulfonyl, sulfonamido, amino, mercapto, or 2-methylbut-2-en-4-yl, wherein n is an integer from 0 to 12 and m is an integer from 0 to 12.

This method comprises reacting a substituted or unsubstituted 2,5-dibromo-1,4-benzoquinone compound of the formula VI:

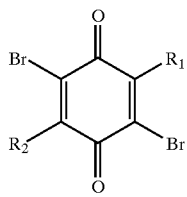

(VI)

wherein R₁ and R₂ are as defined above, with one indole of the formula VII:

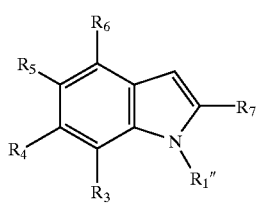

(VII)

wherein

R₁″ and R₃–R₇ are as defined above. The reaction is carried out in a polar organic solvent and in the presence of metal carbonate.

The method of the present invention may further comprise reacting the indolylquinone compound of formula IV with an alkali metal hydroxide to produce a compound of the formula IV wherein R₁ and R₂ are OH.

The method may further comprise reacting the indolylquinone compound of formula IV wherein R₁, R₂ and R₃₀ are Br, F, Cl or I, with a mixture of an alkali metal hydroxide and an alcohol of the formula R'OH, wherein R' is lower alkyl or alkylaryl, to produce an indolylquinone compound of the formula IV wherein R₁ is OR₁'0 and R₂ is OR₂' wherein R₁' and R₂' are each independently lower alkyl, aryl or alkylaryl.

In another embodiment, the present invention further encompasses methods for producing large quantities of known, naturally occurring indolylquinones in high purity and in high yield. In yet another embodiment, the present invention is directed to known, synthetically prepared naturally occurring indolylquinones of high purity which are obtainable in large quantities and in high yield. The invention also encompasses the preparation of novel monoindolylquinones, i.e., compounds substituted with only one indole, and the monoindolylquinone compounds, as described below.

"Protein tyrosine kinase" will, herein, be abbreviated "PTK". It is to be understood that "PTK" may refer to either a transmembrane, receptor-type protein tyrosine kinase or a cytoplasmic protein tyrosine kinase, unless otherwise indicated.

By the term "alkyl" as used herein is meant a straight or branched chain saturated hydrocarbon group having from 1 to 20 carbons, preferabably 1–12 carbons, such as methyl, ethyl, isopropyl, n-butyl, s-butyl, t-butyl, 3-methyl-n-butyl, n-amyl, isoamyl, n-hexyl, n-octyl and n-decyl; "alkenyl" and "alkynyl" are used to mean straight or branched chain hydrocarbon groups having from 2 to 12 carbons and unsaturated by a double or triple bond respectively, such as vinyl, allyl, propargyl, 1-methylvinyl, but-1-enyl, but-2-enyl, but-2-ynyl, 1 methylbut-2-enyl, pent-1-enyl, pent-3-enyl, 3-methylbut-1-ynyl, 1,1-dimethylallyl, hex-2-enyl and 1-methyl-1-ethylallyl; "alkylaryl" means the aforementioned alkyl groups substituted by a phenyl group such as benzyl, phenethyl, phenopropyl, 1-benzylethyl, phenobutyl and 2-benzylpropyl; "aryl" as used herein includes a monocyclic aromatic ring, including aromatic hydrocarbons; "bicyclic aryl" as used herein includes bicyclic rings, wherein at least one ring is aromatic, including aromatic hydrocarbons; "heteroaryl" as used herein includes monocyclic or bicyclic rings, wherein at least one ring is heteroaromatic, including heteroaromatic hydrocarbons; the term "hydroxy-alkyl" means the aforementioned alkyl groups substituted by a single hydroxyl group such as 2-hydroxyethyl, 2-hydroxypropyl, 3-hydroxypropyl, 4-hydroxybutyl, 1-hydroxybutyl and 6-hydroxyhexyl.

The term "substituted" as used herein means that the group in question may bear one or more substituents including but not limited to a radical in which one or more hydrogen atoms are each independently replaced with the same or different substituent(s). Typical substituents include, but are not limited to, alkoxy, —X, —R, —O—, =O, —OR, —O—OR, —SR, —S⁻, =S, —NRR, =NR, —CX₃, —CN, —OCN, —SCN, —NCO, —NCS, —NHCHO, —NHCOC₁–C₄alkyl, —NHCOCH₃, —NHCOCH₂Cl, —NHCOCHC₂, —NHCOCCl₃, —NHCOCF₃, —NHCOCH₂C₆H₄-o-NO₂, —NHCOCH₂OC₆H₄-o-NO₂, —NHCOCH₂COCH₃, —NHCOCH₂—N⁺C₅H₅Cl⁻, —NHCOCH₂NHCS₂CH₂C₆H₅, —NHCOCH₂CH₂C₆H₅, —NHCOCH₂C₆H₄-p-OH, —NHCOCH₂CH₂C₆H₄-o-NO₂, —NHCOC(CH₃)₂OC₆H₄-o-NO₂, —NHCOC(CH₃)₂OC₆H₄-o-N=NC₆H₅, —NHCO(CH₂)₃Cl, —NHCOCH(CH₃)₂, —NHCOCH=CHC₆H₄-o-NO₂, —NHCO-2-pyridyl, —NO, —NO₂, =N₂, —N₃, —NHOH, —S(O)₂O⁻, —S(O)₂OH, —S(O)₂R, —P(O)(O⁻)₂, —P(O)(OH)₂, —C(O)R, —C(O)X, —C(S)R, —C(S)X, —COOH, —C(O)OR, —C(O)O⁻, —C(S)OR, —C(O)SR, —C(S)SR, —C(O)NRR, —C(S)NRR, and —C(NR)NRR, where each X is independently a halogen (preferably —F, —Cl or —Br) and each R is independently —H, alkyl, lower alkyl, alkenyl, alkynyl, aryl, alkylaryl, heteroaryl, bicyclic aryl, hydroxyalkyl and other substituents known to those skilled in the art.

Other features and advantages of the invention will be apparent from the following description of the preferred embodiments thereof, and from the claims.

BRIEF DESCRIPTION OF THE FIGURE

FIG. 1 is a bar graph depicting the results of an ELISA assay quantitating the amount of tyrosine phosphorylation, and potentially of activation, of the insulin receptor protein tyrosine kinase β subunit upon stimulation of cells with various bis-indolylquinone compounds and insulin. The compounds tested are as follows: (a) 2,5-dihydroxy-3,6-di-(2-methylindol-3-yl)-1,4-quinone; (b) 2,5-dihydroxy-3,6-di-[2-(3-methyl-n-butyl)indol-3-yl]-1,4-quinone; (c) 2,5-dihydroxy-3,6-di-(3-ethylindol-3-yl)-1,4-quinone; (d) 2,5-dihydroxy-3,6-di-(2-n-butylindol-3-yl)-1,4-quinone; (e) 2,5-diacetoxy-3,6-di-[2-(3-methy-n-butyl)indol-3-yl]-1,4-quinone; (f) 3-(2-carboxyindol-3-yl)-2,5-dihydroxy-6-(2-methylindol-3-yl)-1,4-quinone; (g) 2,5-dihydroxy-3,6-di-(2-phenylindol-3-yl)-1,4-quinone; (h) 2,5-dihydroxy-6-[2-(3-methyl-n-butyl)indol-3-yl]-3-(2-phenylindol-3-yl)-1,4-quinone; (i) 2,5-dihydroxy-6-(2-methylindol-3-yl)-3-(2-phenylindol-3-yl)-1,4-quinone; (j) 6-(2-n-butylindol-3-yl)-3-(2-carboxyindol-3-yl)-2,5-dihydroxy-1,4-quinone; (k) 2,5-dihydroxy-3,6-di[2-(2phenylethyl)indol-3-yl]-1,4-quinone; (l) 3-(2-carboxyindol-3-yl)-2,5-dihydroxy-6-[2-(3-methyl-n-butyl)indol-3-yl]-1,4-quinone; (m) 3-(2-carboxyindol-3-yl)-2,5-dihydroxy-6-(2-phenylindol-3-yl)-1,4-quinone; (o) 2,5-dihydroxy-3,6-di-(5-methoxy-2- methylindol-3-yl)-1,4-quinone; (p) 3,6-di-(5-chloro-2-methylindol-3-yl)-2,5-dihydroxy-1,4-quinone; (q) 3-(2-carboxy-5-chloroindol-3-yl)-2,5-dihydroxy-6-(2-methyl-5-methoxyindol-3-yl)-1,4-quinone; (r) 2,5-dihydroxy-3,6-di-(2-naphthylindol-3-yl)-1,4-quinone; (s) 3-[2-(N-butylcarboxamido)-indol-3-yl)]-6-(n-butylindol-3-yl)-2,5-dihydroxy-1,4-quinone; (t) 2,5-dimethoxy-3,6-di-[2-(3-methyl-n-butyl)indol-3-yl]-1,4-quinone; (u) 2,5-dihydroxy-3-(1,2-dimethylindol-3-yl)-6-(2-methylindol-3-yl)-1,4-quinone; (v) 3-(1-benzyl-2-methylindol-3-yl)-2,5-dihydroxy-6-(2-methylindol-3-yl)-1,4-quinone; (w) 2-hydroxy-5-methoxy-3,6-di-[2-(3-methyl-n-butyl)-indol-3-yl]-1,4-quinone; and (x) 2,5-dihydroxy-6-(indol-3-yl)-3-[2(2-methylbut-2-ene-4-yl)-indol-3-yl]-1,4-quinone.

4. DETAILED DESCRIPTION OF THE INVENTION

Described herein are compounds, compositions and methods for the inhibition of cell signal transduction. In preferred embodiments, the compounds, compositions and methods inhibit interactions of protein tyrosine kinases and adaptor proteins, especially those interactions associated with a cell proliferative disorder. Also described herein are methods for treating insulin-related disorders in an animal using indolylquinone compounds as hypoglycemic agents and insulin mimetics. Specifically, described below are particular organic compounds, methods for the synthesis of such compounds, and techniques utilizing such compounds.

4.1 The Compounds of the Invention

The compounds of the present invention are described by the following formula I:

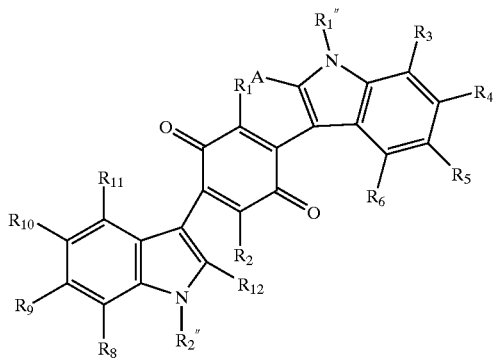

(I)

or a pharmaceutically acceptable salt thereof, wherein:

A is monocyclic aryl, bicyclic aryl or heteroaryl;

$R_1$ and $R_2$ are each independently Br, Cl, F, I, H, OH, or —OCOR, wherein R is lower alkyl, aryl or alkylaryl;

$R_1''$ and $R_2''$ are each independently H, $C_1$–$C_7$ alkyl, $C_2$–$C_7$ alkenyl, $C_2$–$C_7$ alkynyl, arylalkyl or aryl; and $R_3$ to $R_6$ and $R_8$ to $R_{12}$ are each independently hydrogen, branched or unbranched $C_1$–$C_n$ alkyl, alkylcarboxy, $C_2$–$C_m$ alkenyl, $C_2$–$C_m$ alkynyl, alkenylcarboxy, monocyclic aryl, bicyclic aryl, heteroaryl, alkylaryl, hydroxy, hydroxyalkyl, $C_1$–$C_n$ alkoxy, nitro, halo, trihalomethyl, amido, carboxamido, carboxy, sulfonyl, sulfonamido, amino, mercapto, or 2-methylbut-2-en-4-yl, wherein n is an integer from 0 to 12, preferably 1–7, and m is an integer from 0 to 12, preferably 1–7.

Preferred compounds of the present invention are described by the formula II:

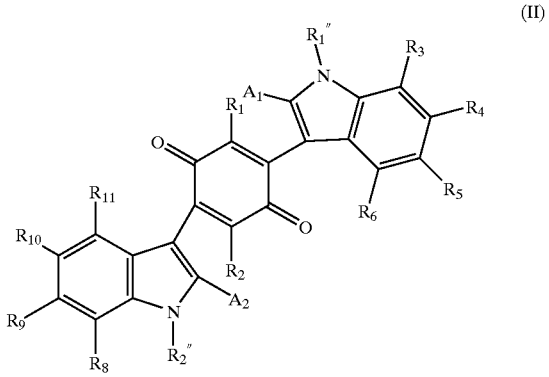

(II)

or a pharmaceutically acceptable salt thereof, wherein:

$A_1$ and $A_2$ are each independently carboxy, monocyclic aryl, bicyclic aryl or heteroaryl;

$R_1$ and $R_2$ are each independently Br, Cl, F, I, H, OH, or —OCOR, wherein R is lower alkyl, aryl or alkylaryl;

$R_1''$ and $R_2''$ are each independently H, $C_1$–$C_7$ alkyl, $C_2$–$C_7$ alkenyl, $C_2$–$C_7$ alkynyl, arylalkyl or aryl; and $R_3$ to $R_6$ and $R_8$ to $R_{11}$ are each independently hydrogen, branched or unbranched $C_1$–$C_n$ alkyl, alkylcarboxy, $C_2$–$C_m$ alkenyl, $C_2$–$C_m$ alkynyl, alkenylcarboxy, aryl, alkylaryl, hydroxy, hydroxyalkyl, $C_1$–$C_n$ alkoxy, nitro, halo, trihalomethyl, amido, carboxamido, carboxy, sulfonyl, sulfonamido, amino, mercapto, or 2-methylbut-2-en-4-yl, wherein n is an integer from 0 to 12, preferably 1–7, and m is an integer from 0 to 12, preferably 1–7.

Preferred compounds of the present invention are compounds of formula 1 wherein A is, compounds of formula II wherein $A_1$ and $A_2$ are each independently:

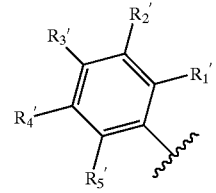

wherein $R_1'$ to $R_5'$ are each independently hydrogen, branched or unbranched $C_1$–$C_n$ alkyl, alkylcarboxy, $C_2$–$C_m$ alkenyl, $C_2$–$C_m$ alkynyl, alkenylcarboxy, aryl, alkylaryl, hydroxy, hydroxyalkyl, $C_1$–$C_n$ alkoxy, nitro, halo, trihalomethyl, amido, carboxamido, carboxy, sulfonyl, sulfonamido, amino, mercapto, or 2-methylbut-2-en-4-yl, wherein n is an integer from 0 to 12, preferably 1–7, and m is an integer from 0 to 12, preferably 1–7; or

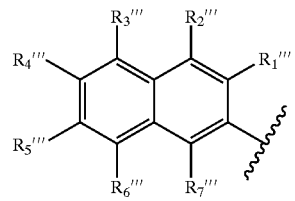

wherein $R_1'''$ to $R_7'''$ are each independently hydrogen, branched or unbranched $C_1$–$C_n$ alkyl, alkylcarboxy, $C_2$–$C_n$ alkenyl, $C_2$–$C_m$ alkynyl, alkenylcarboxy, aryl, alkylaryl, hydroxy, hydroxyalkyl, $C_1$–$C_n$ alkoxy, nitro, halo, trihalomethyl, amido, carboxamido, carboxy, sulfonyl, sulfonamido, amino, mercapto, or 2-methylbut-2-en-4-yl, wherein n is an integer from 0 to 12, preferably 1–7, and m is an integer from 0 to 12, preferably 1–7.

In a preferred embodiment, $R_1'$ to $R_5'$ are H; and $R_{12}$ is carboxy or alkyl, wherein alkyl is a straight or branched chain saturated $C_1$–$C_{20}$ hydrocarbon group; preferably methyl, ethyl, isopropyl, n-butyl, s-butyl, t-butyl, 3-methyl-n-butyl, n-amyl, isoamyl, n-hexyl, n-octyl and n-decyl.

In another preferred embodiment, $R_1'''$ to $R_7'''$ are H.

Preferred compounds of formula I of the invention include, but are not limited to:

(f) 3-(2-carboxyindol-3-yl)-2,5-dihydroxy-6-(2-methylindol-3-yl)-1,4-quinone;
(h) 2,5-dihydroxy-6-[2-(3-methyl-n-butyl)indol-3-yl]-3-(2-phenylindol-3-yl)-1,4-quinone;
(i) 2,5-dihydroxy-6-(2-methylindol-3-yl)-3-(2-phenylindol-3-yl)-1,4-quinone;
(j) 6-(2-n-butylindol-3-yl)-3-(2-carboxyindol-3-yl)-2,5-dihydroxy-1,4-quinone;
(l) 3-(2-carboxyindol-3-yl)-2,5-dihydroxy-6-[2-(3-methyl-n-butyl)indol-3-yl]-1,4-quinone;
(m) 3-(2-carboxyindol-3-yl)-2,5-dihydroxy-6-(2-phenylindol-3-yl)-1,4-quinone;
(n) 3-(2-n-butylindol-3-yl)-6-(2-carboxy-5-chloroindol-3-yl)-2,5-dihydroxy-1,4-quinone; and
(q) 3-(2-carboxy-5-chloroindol-3-yl)-2,5-dihydroxy-6-(2-methyl-5-methoxyindol-3-yl)-1,4-quinone.

Preferred compounds of formula II of the invention include, but are not limited to:

(g) 2,5-dihydroxy-3,6-di-(2-phenylindol-3-yl)-1,4-quinone; and
(r) 2,5-dihydroxy-3,6-di-(2-naphthylindol-3-yl)-1,4-quinone.

Other preferred compounds of the invention include, but are not limited to:

(o) 2,5-dihydroxy-3,6-di-(5-methoxy-2-methylindol-3-yl)-1,4-quinone;
(p) 3,6-di-(5-chloro-2-methylindol-3-yl)-2,5-dihydroxy-1,4-quinone;
(s) 3-[2-(N-butylcarboxamido)-indol-3-yl)]-6-(n-butylindol-3-yl)-2,5-dihydroxy-1,4-quinone;
(u) 2,5-dihydroxy-3-(1,2-dimethylindol-3-yl)-6-(2-methylindol-3-yl)-1,4-quinone;
(v) 3-(1-benzyl-2-methylindol-3-yl)-2,5-dihydroxy-6-(2-methylindol-3-yl)-1,4-quinone; and
(w) 2-hydroxy-5-methoxy-3,6-di-[2-(3-methyl-n-butyl)-indol-3-yl]-1,4-quinone.

4.2 Protein Tyrosine Kinase/Adaptor Protein Complexes

The PTK/adaptor protein complexes which may be disrupted by the compounds, compositions, and methods of the invention comprise at least one member of the PTK family of proteins and at least one member of the adaptor family of proteins, as described below. Under standard physiological conditions, the components of such complexes are capable of forming stable, non-covalent attachments with one or more of the other PTK/adaptor protein complex components. Preferably, the compounds of the invention inhibit PTK/adaptor protein complexes wherein the PTK component is an epidermal growth factor receptor (EGF-R) protein tyrosine kinase molecule, a platelet derived growth factor receptor (PDGF-R) protein tyrosine kinase molecule or an insulin growth factor-like receptor tyrosine kinase molecule (IGF-1R). The methods of the present invention may be particularly useful for inhibiting PTK/adaptor protein complexes, wherein the PTK component is an insulin growth factor-like receptor tyrosine kinase molecule (IGF-1R).

Intracellular, cytoplasmic PTK components of the PTK/adaptor protein complexes may include, for example, members of the Src family, such molecules as src, yes, fgr, fyn, lyn, hck, lck, and blk; members of the Fes family, such as fes and fer; members of the Abl family, such as abl and arg; and members of the Jak family, such as jak1 and jak2. Transmembrane, receptor PTK components of the PTK/adaptor protein complexes may include, for example, such molecules as members of the FGF receptor, Sevenless/ROS, Insulin receptor, PDGF receptor, and EGF receptor family of growth factor receptors.

The adaptor protein components of the PTK/adaptor protein complexes comprise one or more SH2 and/or one or more SH3 non-catalytic domains. The SH2 and SH3 domains which may be a part of the adaptor proteins are as described, above, for the PTK components. Adaptor proteins which may be components of the PTK/adaptor protein complexes may include, for example, p85, c-Crk, SHC, Nck, ISGF3α, guanine triphosphatase activator protein (GAP), and members of the GRB subfamily of proteins, such as GRB-1, GRB-2, GRB-3, GRB-4, GRB-7, and GRB-10. The compounds of the invention are particularly useful for inhibiting PTK/adaptor protein complexes wherein the adaptor protein component is GRB-2.

4.3 Treatment of PTK/Adaptor Protein Complex-Related Cell-Proliferative Disorders The compounds described herein and/or pharmaceutical compositions of the invention (described below in Section 4.7) may be used for the treatment of cell proliferative disorders, such as oncogenic disorders, involving a PTK capable of complexing with a member of the SH2- and/or SH3-containing family of adaptor proteins. The methods and compounds of the invention may be preferentially utilized in the treatment of cell proliferative disorders involving PTK/adaptor protein complexes wherein the PTK component is EGF-R, PDGF-R, MCT or IGF-1R. Most preferably, the compounds of the invention may be used in the treatment of cell proliferative disorders involving complexes of PTK and GRB-2.

Among the oncogenic disorders which may be treated by the compounds of the invention are, for example, BCR-ABL-associated cancers (such as, for example, chronic myelogenous and acute lymphocytic leukemias), gliomas, glioblastomas, melanoma, human ovarian cancers, human breast cancers (especially HER-2IGRB-7-associated human breast cancers), and human prostate cancers.

Assays for determining the effectiveness of a compound in the disruption of a PTK/adaptor protein complex are described below in Section 4.4. Methods for the administering the compounds and/or pharmaceutical compositions of the invention to patients are also described below in Section 4.7.

"Disruption", as used here, is meant to refer not only to a physical separation of PTK/adaptor protein complex components, but is also meant to refer to a perturbation of the activity of the PTK/adaptor complexes, regardless of whether or not such complexes remain able, physically, to form. "Activity", as used here, refers to the function of the PTK/adaptor protein complex in the signal transduction cascade of the cell in which such a complex is formed, i.e., refers to the function of the complex in effecting or inhibiting the transduction of an extracellular signal into a cell. The compounds and pharmaceutical compositions of the invention may or may not directly interfere with (i.e., inhibit or enhance) the enzymatic activity of the protein tyrosine kinase of interest.

4.4 Assays for the Disruption of PTK/Adaptor Protein Complexes

A variety of methods may be used to assay the ability that the compounds of the invention exhibit to disrupt PTK/adaptor protein complexes. For example, in vitro complex formation may be assayed by, first, immobilizing one component, or a functional portion thereof, of the complex of interest to a solid support. Second, the immobilized complex component may be exposed to a compound such as one identified as above, and to the second component, or a functional portion thereof, of the complex of interest. Third, it may be determined whether or not the second component is still capable of forming a complex with the immobilized component in the presence of the compound.

Additionally, in vivo complex formation may be assayed by utilizing co-immunoprecipitation techniques well known to those of skill in the art. Briefly, a cell line capable of forming a PTK/adaptor complex of interest may be exposed to one or more of the compounds of the invention, and a cell lysate may be prepared from this exposed cell line. An antibody raised against one of the components of the complex of interest may be added to the cell lysate, and subjected to standard immunoprecipitation techniques. In cases where a complex is still formed, the immunoprecipitation will precipitate the complex, whereas in cases where the complex has been disrupted, only the complex component to which the antibody is raised will be precipitated.

1. The effect of a compound of the invention on the transformation capability of the PTK/adaptor protein of interest may be directly assayed. For example, one or more of the compounds of the invention may be administered to a cell such as a fibroblast or hematopoietic cell capable of forming a PTK/adaptor complex which, in the absence of a compound of the invention, would lead to the cell's transformation (Muller, A. J. et al., 1991, *Mol. Cell. Biol.* 11:1785–1792; McLaughlin, J. et al., 1987, *Proc. Natl. Acad. Sci. USA* 84:6558–6562). The transformation state of the cell may then be measured in vitro, by monitoring, for example, its ability to form colonies in soft agar (Lugo and Witte, 1989, *Mol. Ce25 ll. Biol.* 9:1263–1270; Gishizky, M. L. and Witte, O. N., 1992, *Science* 256:836–839). Alternatively, a cell's transformation state may be monitored in vivo by determining its ability to form tumors in immunodeficient nude or severe combined immunodeficiency (SCID) mice (Sawyers, C. L. et al., 1992, *Blood* 79:2089–2098). Further, the ability of the compounds of the present invention, to inhibit various tumor cell lines, such as for example, melanoma, prostate, lung and mammary tumor cell lines established as SC xenografts can be examined.

4.5 Methods for Treating Insulin-Related Disorders

Another embodiment of the present invention encompasses the treatment, prevention and regulation of insulin-related disorders such as diabetes using compounds that can act in vivo as insulin mimetics. Although an understanding of the mechanism by which the compounds act is not required in order to practice the present invention, the compounds are believed to activate the insulin receptor and induce receptor signaling. Such compounds are described by formula III:

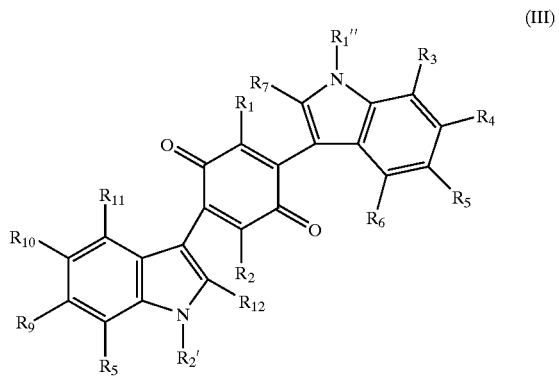

(III)

or a pharmaceutically acceptable salt thereof, wherein:
$R_1$ and $R_2$ are each independently Br, Cl, F, I, H, OH, or —OCOR, wherein R is lower alkyl, aryl or alkylaryl;
$R_1''$ and $R_2''$ are each independently H, $C_1$–$C_7$ alkyl, $C_2$–$C_7$ alkenyl, $C_2$–$C_7$ alkynyl, arylalkyl or aryl;
$R_3$ to $R_{12}$ are each independently hydrogen, branched or unbranched $C_1$–$C_n$ alkyl, alkylcarboxy, $C_2$–$C_m$ alkenyl, $C_2$–$C_m$ alkynyl, alkenylcarboxy, aryl, alkylaryl, hydroxy, hydroxyalkyl, $C_1$–$C_n$ alkoxy, nitro, halo, trihalomethyl, amido, carboxamido, carboxy, sulfonyl, sulfonamido, amino, mercapto, or 2-methylbut-2-en-4-yl, wherein n is an integer from 0 to 12, preferably 1–7, and m is an integer from 0 to 12, preferably 1–7; and
$R_1$ and $R_2$ are preferably Br, Cl, F, H or OH.

Groups $R_3$—$R_{12}$ may be substituted or unsubstituted where appropriate. Specific examples of the compounds useful for treating diabetes in accordance with the methods of the invention can be found in Table 1, below.

Compounds that may be useful for treating diabetes in accordance with the methods of the invention include, but are not limited to:

(a) 2,5-dihydroxy-3,6-di-(2-methylindol-3-yl)-1,4-quinone;
(b) 2,5-dihydroxy-3,6-di-[2-(3-methyl-n-butyl)indol-3-yl]-1,4-quinone;
(c) 2,5-dihydroxy-3,6-di-(3-ethylindol-3-yl)-1,4-quinone;
(d) 2,5-dihydroxy-3,6-di-(2-n-butylindol-3-yl)-1,4-quinone;
(e) 2,5-diacetoxy-3,6-di-[2-(3-methyl-n-butyl)indol-3-yl]-1,4-quinone;
(f) 3-(2-carboxyindol-3-yl)-2,5-dihydroxy-6-(2-methylindol-3-yl)-1,4-quinone;
(g) 2,5-dihydroxy-3,6-di-(2-phenylindol-3-yl)-1,4-quinone;
(h) 2,5-dihydroxy-6-[2-(3-methyl-n-butyl)indol-3-yl]-3-(2-phenylindol-3-yl)-1,4-quinone;
(i) 2,5-dihydroxy-6-(2-methylindol-3-yl)-3-(2-phenylindol-3-yl)-1,4-quinone;
(j) 6-(2-n-butylindol-3-yl)-3-(2-carboxyindol-3-yl)-2,5-dihydroxy-1,4-quinone;
(k) 2,5-dihydroxy-3,6-di-[2-(2-phenylethyl)indol-3-yl]-1,4-quinone;
(l) 3-(2-carboxyindol-3-yl)-2,5-dihydroxy-6-[2-(3-methyl-n-butyl)indol-3-yl]-1,4-quinone;
(m) 3-(2-carboxyindol-3-yl)-2,5-dihydroxy-6-(2-phenylindol-3-yl)-1,4-quinone;
(n) 3-(2-n-butylindol-3-yl)-6-(2-carboxy-5-chloroindol-3-yl)-2,5-dihydroxy-1,4-quinone;
(o) 2,5-dihydroxy-3,6-di-(5-methoxy-2-methylindol-3-yl)-1,4-quinone;

(p) 3,6-di-(5-chloro-2-methylindol-3-yl)-2,5-dihydroxy-1,4-quinone;

(q) 3-(2-carboxy-5-chloroindol-3-yl)-2,5-dihydroxy-6-(2-methyl-5-methoxyindol-3-yl)-1,4-quinone;

(r) 2,5-dihydroxy-3,6-di-(2-naphthylindol-3-yl)-1,4-quinone;

(s) 3-[2-(N-butylcarboxamido)-indol-3-yl)]-6-(n-butylindol-3-yl)-2,5-dihydroxy-1,4-quinone;

(t) 2,5-dimethoxy-3,6-di-[2-(3-methyl-n-butyl)indol-3-yl]-1,4-quinone;

(u) 2,5-dihydroxy-3-(1,2-dimethylindol-3-yl)-6-(2-methylindol-3-yl)-1,4-quinone;

(v) 3-(1-benzyl-2-methylindol-3-yl)-2,5-dihydroxy-6-(2-methylindol-3-yl)-1,4-quinone; and (w) 2-hydroxy-5-methoxy-3,6-di-[2-(3-methyl-n-butyl)-indol-3-yl]-1,4-quinone.

Preferred compounds for treating diabetes in accordance with the methods of the invention include, but are not limited to:

(k) 2,5-dihydroxy-3,6-di-[2-(2-phenylethyl)indol-3-yl]-1,4-quinone;

(l) 3-(2-carboxyindol-3-yl)-2,5-dihydroxy-6-[2-(3-methyl-n-butyl)indol-3-yl]-1,4-quinone;

(p) 3,6-di-(5-chloro-2-methylindol-3-yl)-2,5-dihydroxy-1,4-quinone; and (v) 3-(1-benzyl-2-methylindol-3-yl)-2,5-dihydroxy-6-(2-methylindol-3-yl)-1,4-quinone.

In another embodiment of the present invention, compounds that can be used as insulin mimetics in accordance with the methods of the invention are described by formula IV:

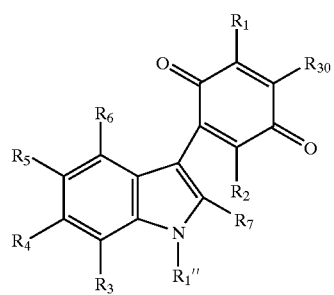

(IV)

or a pharmaceutically acceptable salt thereof, wherein:

$R_1$, $R_2$ and $R_{30}$ are each independently Br, Cl, F, I, H, OH or —OCOR, wherein R is lower alkyl, aryl or alkylaryl;

$R_1''$ is H, $C_1$–$C_7$ alkyl, $C_2$–$C_7$ alkenyl, $C_2$–$C_7$ alkynyl, arylalkyl or aryl; and $R_3$ to $R_7$ are each independently hydrogen, branched or unbranched $C_1$–$C_n$ alkyl, alkylcarboxy, $C_2$–$C_m$ alkenyl, alkynyl, alkenylcarboxy, aryl, alkylaryl, hydroxy, hydroxyalkyl, $C_1$–$C_n$ alkoxy, nitro, halo, trihalomethyl, amido, carboxamido, carboxy, sulfonyl, sulfonamido, amino, mercapto, or 2-methylbut-2-en-4-yl, wherein n is an integer from 0 to 12 and m is an integer from 0 to 12.

Specific compounds in this embodiment of the present invention can be found in Table 2, below.

The present invention also encompasses methods for treating diabetes using compounds of formula I:

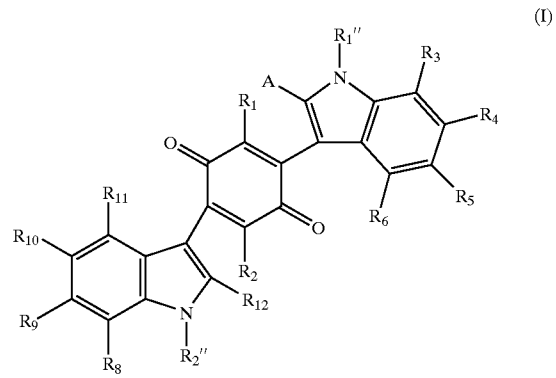

(I)

and pharmaceutically acceptable salts thereof, wherein:

A is monocyclic aryl, bicyclic aryl or heteroaryl;

$R_1$ and $R_2$ are each independently Br, Cl, F, I, H, OH, or —OCOR, wherein R is lower alkyl, aryl or alkylaryl;

$R_1''$ and $R_2''$ are each independently H, $C_1$–$C_7$ alkyl, $C_2$–$C_7$ alkenyl, $C_2$–$C_7$ alkynyl, arylalkyl or aryl; and $R_3$ to $R_6$ and $R_8$ to $R_{12}$ are each independently hydrogen, branched or unbranched $C_1$–$C_n$ alkyl, alkylcarboxy, $C_2$–$C_m$ alkenyl, $C_2$–$C_m$ alkynyl, alkenylcarboxy, monocyclic aryl, bucyclic aryl, heteroaryl, alkylaryl, hydroxy, hydroxyalkyl, $C_1$–$C_n$ alkoxy, nitro, halo, trihalomethyl, amido, carboxamido, carboxy, sulfonyl, sulfonamido, amino, mercapto, or 2-methylbut-2-en-4-yl, wherein n is an integer from 0 to 12, preferably 1–7, and m is an integer from 0 to 12, preferably 1–7.

The present invention also encompasses methods for treating diabetes using compounds of formula II:

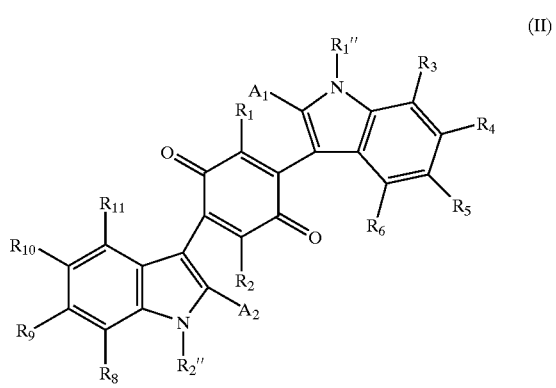

(II)

or a pharmaceutically acceptable salt thereof, wherein:

$A_1$ and $A_2$ each independently carboxy, monocyclic aryl, bicyclic aryl or heteroaryl;

$R_1$ and $R_2$ are each independently Br, Cl, F, I, H, OH, or —OCOR, wherein R is lower alkyl, aryl or alkylaryl;

$R_1''$ and $R_2''$ are each independently H, $C_1$–$C_7$ alkyl, $C_2$–$C_7$ alkenyl, $C_2$–$C_7$ alkynyl, arylalkyl or aryl; and $R_3$ to $R_6$ and $R_8$ to $R_{11}$ are each independently hydrogen, branched or unbranched $C_1$–$C_n$ alkyl, alkylcarboxy, $C_2$–$C_m$ alkenyl, $C_2$–$C_m$ alkynyl, alkenylcarboxy, aryl, alkylaryl, hydroxy, hydroxyalkyl, $C_1$–$C_n$ alkoxy, nitro, halo, trihalomethyl, amido, carboxamido, carboxy, sulfonyl, sulfonamido, amino, mercapto, or 2-methylbut-2-en-4-yl, wherein n is an integer from 0 to 12, preferably 1–7, and m is an integer from 0 to 12, preferably 1–7.

In a preferred embodiment, the methods for treating diabetes of the present invention utilize compounds of formula I wherein A is, or formula II wherein $A_1$: and $A_2$ are each independently:

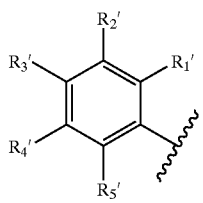

wherein $R_1'$ to $R_5'$ are each independently hydrogen, branched or unbranched $C_1$–$C_n$ alkyl alkylcarboxy, $C_2$–$C_m$ alkenyl, $C_2$–$C_m$ alkynyl, alkenylcarboxy, aryl, alkylaryl, hydroxy, hydroxyalkyl, $C_1$–$C_n$ alkoxy, nitro, halo, trihalomethyl, amido, carboxamido, carboxy, sulfonyl, sulfonamido, amino, mercapto, or 2-methylbut-2-en-4-yl, wherein n is an integer from 0 to 12, preferably 1–7, and m is an integer from 0 to 12, preferably 1–7; or

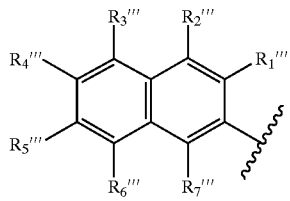

wherein $R_1'''$ to $R_7'''$ are each independently hydrogen, branched or unbranched $C_1$–$C_n$ alkyl, alkylcarboxy, $C_2$–$C_m$ alkenyl, $C_2$–$C_m$ alkynyl, alkenylcarboxy, aryl, alkylaryl, hydroxy, hydroxyalkyl, $C_1$–$C_n$ alkoxy, nitro, halo, trihalomethyl, amido, carboxamido, carboxy, sulfonyl, sulfonamido, amino, mercapto, or 2-methylbut-2-en-4-yl, wherein n is an integer from 0 to 12, preferably 1–7, and m is an integer from 0 to 12, preferably 1–7.

In preferred embodiments, $R_1'$ to $R_5'$ are $H_1'''$ and $R_7'''$ to $R_7$ are H.

In one embodiment, the methods of the present invention utilize compounds of formula I, wherein $R_{12}$ is an alkyl group selected from the group consisting of methyl, ethyl, isopropyl, n-butyl, s-butyl, t-butyl, 3-methyl-n-butyl, n-amyl, isoamyl, n-hexyl, n-octyl and n-decyl.

4.6 Assays for Insulin Mimetic Activity

A variety of methods are available for assaying the ability of compounds to mimic the effects of insulin. For example, in vitro assays for insulin receptor activation and phosphorylation may be performed. In one assay, insulin receptor protein tyrosine kinase activity is measured. Cells expressing the insulin receptor are treated with the test compounds or insulin. Cells are then lysed and insulin receptor is captured with an anti-insulin receptor antibody. Activity of the PTK is then measured with [$\gamma$-$^{32}$P]ATP and poly (Glu:Tyr) as substrate as the amount of $^{32}$P incorporation by the PTKs of compound treated cells into the peptide compared to the amount of $^{32}$P incorporation by the PTKs of insulin treated cells. In a second assay, the amount of tyrosine-phosphorylated insulin receptor is measured in treated and untreated cells. Cells treated with test compounds, insulin, and untreated cells are lysed and the proteins are separated by gel electrophoresis, blotted onto a membrane, and detected with an antibody to phosphotyrosine to determine the relative amounts of phosphorylated insulin receptor present. In a third assay, proteins from cells treated with test compounds and insulin are immunoprecipitated with an antibody to phosphotyrosine and the activity of PI-3 kinase, a protein that is downstream from the insulin receptor in the signaling cascade, is determined.

Glucose uptake in cultured cells and in intact muscles may also be determined in vitro. Cells or muscle tissues are first treated with the test compounds or insulin, and are then exposed to radiolabeled glucose. Glucose uptake is then quantitated by quantitating relative amounts of radioactivity in the cells or tissues.

In vivo efficacy of test compounds in lowering blood glucose levels or in increasing glucose tolerance can be tested using diabetic or obese mice, respectively. In the first instance, test compounds are administered to diabetic mice orally, mice are denied access to food, and plasma glucose levels are monitored before and after administration with a glucometer. In the second instance, test compounds are administered to obese mice orally, mice are denied access to food, and then a bolus of glucose is injected intraperitoneally. Glucose levels are monitored using a glucometer.

4.7 Pharmaceutical Compositions and Methods of Administration

The compounds of the invention, as described, above, in Section 4.1, may be administered to a patient at therapeutically effective doses to treat or ameliorate cell proliferative disorders. In some embodiments, the compounds of the invention are administered to treat cell proliferative disorders involving PTK/GRB-2 interactions. In addition, indolylquinone compounds described herein may be administered to a patient to treat or ameliorate the symptoms of insulin-related disorders. In the case of cell proliferative disorders, a therapeutically effective dose refers to that amount of the compound sufficient to result in amelioration of symptoms of a cell proliferative disorder. In the treatment of insulin-related disorders, a therapeutically effective dose refers to that amount of the compound sufficient to ameliorate the symptoms of the insulin-related disorder. As used herein, a therapeutically effective dose also means an amount of the compound sufficient to control blood glucose levels of the patient, or to maintain the blood glucose levels of the patient at a normal level.

The methods described below for determining the effective dosage of the compounds of the invention are appropriate for determining effective doses for both the treatment of diabetes and treatment of cell proliferative disorders. Further, described below are methods for formulations and pharmaceutical compositions comprising the compounds of the invention, and methods for the administration of such compounds, formulations, and compositions. The formulation methods, pharmaceutical compositions and methods of administration described below are suitable both in the treatment of cell proliferative disorders and of insulin-related disorders.

4.7.1. Effective Dose

Toxicity and therapeutic efficacy of the compounds of the invention can be determined by standard pharmaceutical procedures in cell cultures or experimental animals, e.g., for determining the $LD_{50}$ (the dose lethal to 50% of the population) and the $ED_{50}$ (the dose therapeutically effective in 50% of the population). The dose ratio between toxic and therapeutic effects is the therapeutic index and it can be expressed as the ratio $LD_{50}/ED_{50}$. Compounds which exhibit large therapeutic indices are preferred. While compounds that exhibit toxic side effects may be used, care should be taken to design a delivery system that targets such compounds to the site of affected tissue in order to minimize potential damage to uninfected cells and, thereby, reduce side effects.

The data obtained from the cell culture assays and animal studies can be used in formulating a range of dosage for use in humans. The dosage of such compounds lies preferably within a range of circulating concentrations that include the $ED_{50}$ with little or no toxicity. The dosage may vary within this range depending upon the dosage form employed and the route of administration utilized. For any compound used in the methods of the invention, the therapeutically effective dose can be estimated initially from cell culture assays. A dose may be formulated in animal models to achieve a circulating plasma concentration range that includes the $IC_{50}$ (i.e., the concentration of the test compound which achieves a half-maximal inhibition of symptoms) as determined in cell culture. Such information can be used to more accurately determine useful doses in humans. Levels in plasma may be measured, for example, by high performance liquid chromatography.

Dosage amount and interval may be adjusted individually to provide plasma levels of the active moiety which are sufficient to maintain inhibition of adaptor protein/protein tyrosine kinase interactions, to maintain reasonable blood glucose levels, or minimal effective concentration (MEC). The MEC will vary for each compound but can be estimated from in vitro data, e.g., the interactions using the assays described herein. Dosages necessary to achieve the MEC will depend on individual characteristics and route the administration. However, HPLC assays or bioassays can be used to determine plasma concentrations.

Dosage intervals can also be determined using the MEC value. Compounds should be administered using a regimen which maintains plasma levels above the MEC for 10–90% of the time, preferably between 30–90% and most preferably between 50–90%. In the case of insulin-related disorders, such as diabetes, compounds should be administered so as to provide improvement in clinical symptoms and blood and urine glucose levels. The compounds may be used alone or in combination with other glucose-lowering agents, including insulin.

4.7.2. Formulation and Administration

As discussed, above, adaptor proteins, and specifically GRB-2, are intracellular proteins. Thus, PTK/adaptor protein interactions are intracellular, regardless of whether the PTK of interest is of the transmembrane or the intracellular type. Therefore, the compounds of the invention act intracellularly to interfere with the formation and/or activity of the PTK/adaptor complexes. Furthermore, evidence of the interaction of an asymmetrical asterriquinone with the insulin receptor indicates that the compound acts directly on the intracellular PTK portion of the receptor. A variety of methods are known to those of skill in the art for administration of compounds which act intracellularly, as, for example, discussed in this Section.

Pharmaceutical compositions for use in accordance with the compounds of the present invention may be formulated in conventional manner using one or more physiologically acceptable carriers or excipients.

Thus, the compounds and their physiologically acceptable salts and solvates may be formulated for administration by inhalation or insufflation (either through the mouth or the nose) or oral, buccal, parenteral or rectal administration.

For oral administration, the pharmaceutical compositions may take the form of, for example, tablets or capsules prepared by conventional means with pharmaceutically acceptable excipients such as binding agents (e.g., pregelatinised maize starch, polyvinylpyrrolidone or hydroxypropyl methylcellulose); fillers (e.g., lactose, microcrystalline cellulose or calcium hydrogen phosphate); lubricants (e.g., magnesium stearate, talc or silica); disintegrants (e.g., potato starch or sodium starch glycolate); or wetting agents (e.g., sodium lauryl sulphate). The tablets may be coated by methods well known in the art. Liquid preparations for oral administration may take the form of; for example, solutions, syrups or suspensions, or they may be presented as a dry product for constitution with water or other suitable vehicle before use. Such liquid preparations may be prepared by conventional means with pharmaceutically acceptable additives such as suspending agents (e.g., sorbitol syrup, cellulose derivatives or hydrogenated edible fats); emulsifying agents (e.g., lecithin or acacia); non-aqueous vehicles (e.g., almond oil, oily esters, ethyl alcohol or fractionated vegetable oils); and preservatives (e.g., methyl or propyl-p-hydroxybenzoates or sorbic acid). The preparations may also contain buffer salts, flavoring, coloring and sweetening agents as appropriate.

Preparations for oral administration may be suitably formulated to give controlled release of the active compound.

For buccal administration the compositions may take the form of tablets or lozenges formulated in conventional manner.

For administration by inhalation, the compounds for use according to the present invention may be conveniently delivered in the form of an aerosol spray presentation from pressurized packs or a nebuliser, with the use of a suitable propellant, e.g., dichlorodifluoromethane, trichlorofluoromethane, dichlorotetrafluoroethane, carbon dioxide or other suitable gas. In the case of a pressurized aerosol the dosage unit may be determined by providing a valve to deliver a metered amount. Capsules and cartridges of e.g. gelatin for use in an inhaler or insufflator may be formulated containing a powder mix of the compound and a suitable powder base such as lactose or starch.

The compounds may be formulated for parenteral administration by injection, e.g., by bolus injection or continuous infusion. Formulations for injection may be presented in unit dosage form, e.g., in ampoules or in multi-dose containers, with an added preservative. The compositions may take such forms as suspensions, solutions or emulsions in oily or aqueous vehicles, and may contain formulatory agents such as suspending, stabilizing and/or dispersing agents. Alternatively, the active ingredient may be in powder form for constitution with a suitable vehicle, e.g., sterile pyrogen-free water, before use.

The compounds may also be formulated in rectal compositions such as suppositories or retention enemas, e.g., containing conventional suppository bases such as cocoa butter or other glycerides.

In addition to the formulations described previously, the compounds may also be formulated as a depot preparation. Such long acting formulations may be administered by implantation (for example subcutaneously or intramuscularly) or by intramuscular injection. Thus, for example, the compounds may be formulated with suitable polymeric or hydrophobic materials (for example as an emulsion in an acceptable oil) or ion exchange resins, or as sparingly soluble derivatives, for example, as a sparingly soluble salt.

The compositions may, if desired, be presented in a pack or dispenser device which may contain one or more unit dosage forms containing the active ingredient. The pack may for example comprise metal or plastic foil, such as a blister pack. The pack or dispenser device may be accompanied by instructions for administration.

4.8 Syntheses of Mono- and Bis-Indolylquinones

As mentioned above, the present invention relates to a synthetic route for the preparation of a wide variety of indolylquinones including asterriquinone compounds having interesting antitumor and/or insulin mimetic activity. As a result, the invention provides a major contribution to the art in that naturally occurring compounds with important therapeutic properties can be prepared in large quantities, e.g., quantities of about 1 gram or more, with purity in excess of about 95% and in high yield. The availability of large quantities allows the skilled artisan to more quickly and easily test these naturally occurring compounds. Prior to the present invention, such compounds were isolated from natural sources in limited quantities (e.g., about 750 mg or less) and low purity (e.g., less than about 95%). With the present invention, large quantities can more easily be obtained and the purification of complex natural product mixtures is avoided. Finally, the present invention provides a means for preparing novel analogues of the naturally occurring indolylquinones, which analogues may prove to be of greater interest than the naturally occurring compounds for their therapeutic activity or other properties.

More specifically, the present invention provides a solvent-based reaction of indoles and haloquinones in the presence of metal carbonate. It has been discovered that the reaction of indoles and halo-quinones using a polar organic solvent and metal carbonate provides a rapid and efficient reaction under mild conditions, which include but are not limited to mild temperatures, short reaction times and standard/ambient pressures. Thus, the present method is well suited for large scale and commercial production of indolylquinones.

More specifically, the present invention provides methods for the preparation of indolylquinones which involve the reaction of a 2,5-dihalo-1,4-benzoquinone of the formula VI with at least one indole of the formula VII. When one indole is used, a symmetrical bis-indolylquinone of the formula V is obtained as the product. In the alternative, step-wise or concurrent addition of two different indoles may be used to obtain an asymmetrical bis-indolylquinone of the formula III. For example, an asymmetrical bis-indolylquinone may be made by the reaction of a 2,5-dihalo-1,4-benzoquinone with about one equivalent of a first indole, followed by addition of about 1.5 equivalents of a second indole. Preferably, the preparation of asymmetrical bis-indolylquinones is carried out in the presence of about 3 equivalents of metal carbonate. As another alternative, mixtures of two or more indoles may be reacted with the starting quinone to give a mixture of symmetrical and asymmetrical bis-indolylquinones. Finally, the controlled addition of one equivalent of at least one indole to the starting quinone in the presence of about one equivalent of metal carbonate can be used to obtain one or more mono-indolylquinones.

The preferred 2,5-dihalo-1,4-quinones useful in the present invention are the 2,5-dibromo-1,4-benzoquinones of formula VI, which may be substituted or unsubstituted, wherein $R_1$ and $R_2$ are each independently Br, Cl, F, I, OH, H or —OCOR, wherein R is lower alkyl, aryl or alkylaryl. Alternatively, the 2,5-dichloro-, difluoro- or diiodo-1,4-benzoquinones may be used in the methods of the invention. A particularly preferred 2,5-dibromo-1,4-quinone is 2,3,5,6-tetrabromo-1,4-benzoquinone.

The indoles useful in the present invention may be substituted at the 1, 2, 3, 4, 5 or 7 positions with hydrogen, branched or unbranched $C_1$–$C_n$ alkyl, alkylcarboxy, $C_2$–$C_m$ alkenyl, $C_2$–$C_m$ alkynyl, alkenylcarboxy, aryl, akylaryl, hydroxy, hydroxyalkyl, $C_1$–$C_n$ alkoxy, nitro, halo, trihalomethyl, amido, carboxamido, carboxy, sulfonyl, sulfonamido, amino, mercapto, or 2-methylbut-2-en-4-yl, wherein n is an integer from 0 to 12, preferably 1–7, and m is an integer from 0 to 12, preferably 1–7. Preferably, the indoles used in the present invention are substituted at the 2 position. Least preferred indoles are the unsubstituted indoles. Certain indoles useful in the present invention are available from commercial sources such as the Aldrich Chemical Company, Milwaukee, Wis. Alternatively, the indoles may be prepared via a cyclization procedure according to the method of Verley and Bedure, 1925, *Bull. Soc. Chim. Fr.* (37): 190.

Any non-nucleophilic, aprotic solvent may be used in the methods of the invention. Mixtures of solvents may also be used. Preferred solvents are inert or non-reactive, polar organic solvents including but not limited to acetonitrile, dimethyl formamide (DMF) and tetrahydrofuran (THF). A particularly preferred solvent is acetonitrile. The solvent volume will depend upon the scale of the reactors, and may range from a few milliliters up to a multi-liter volumes useful in large-scale production. Reactant concentrations are set forth below.

It is believed that the metal carbonate used in the methods of the present invention assists the reaction of the 2,5-dihalo-1,4-quinone and the indole by scavenging the hydrogen bromide by-product formed in the reaction. Any metal carbonate or mixture of metal carbonates may be used; however, cesium carbonate, potassium carbonate, sodium carbonate, lithium carbonate and mixtures thereof are preferred. A particularly preferred metal carbonate is cesium carbonate. The amount of metal carbonate used in the method ranges from about 2 to about 10 equivalents based on the haloquinone; preferably 2 to 5 equivalents; and most preferably 3 to 4 equivalents.

The reaction may be run at any concentration ranging from about 0.1M to about 5M (molarity based on the haloquinone). Preferably the reaction is run at a concentration of about 1M.

As mentioned above, the reaction to produce a mono-indolylquinone is preferably carried out in the presence of about two equivalents of metal carbonate. Reactions to produce symmetrical or asymmetrical bis-indolylquinones are preferably carried out in the presence of about 3 equivalents of metal carbonate.

According to the methods of the invention, the reaction of the 2,5-dihalo-1,4-quinone with the indole may be run at temperatures ranging from about −10° C. to about 100° C. However, a particularly beneficial aspect of the present invention is that harsh conditions and high temperatures are not required to effect this reaction. Preferably the reaction of the 2,5-dihalo-1,4-quinone is run at a temperature in the range of about 0° C. to about 30° C. More preferably, the reaction is run at about room temperature.

The reaction of the 2,5-dihalo-1,4-quinone with the indole may be conducted under an inert atmosphere such as nitrogen or argon; however, the reaction may also be run in atmospheric air. The reaction may be run at any pressure up to 500 psig; however, it is preferable to conduct the reaction at atmospheric pressure.

The reaction time will vary according to the specific reactants and reaction conditions used, but generally will be from about 2 hours to about 72 hours.

After reaction of the 2,5-dihalo-2,4-quinone and the indole, the product indolylquinones are typically isolated according to standard workup procedures. For example, the crude reaction mixture may be diluted with 1N hydrochloric acid, followed by extraction with an organic solvent such as ethyl acetate. Typically, the organic layer is washed with brine and then dried over anhydrous sodium sulfate. As an alternative to extraction, the crude reaction mixture may simply be filtered to remove solids. The solvent is removed under reduced pressure, and the crude residue is purified by recrystallization, flash chromatography, High Pressure Liquid Chromatography (HPLC) or a combination thereof. Preferably, the residue is purified using flash chromatography and/or High Pressure Liquid Chromatography (HPLC).

In a preferred embodiment, the symmetrical bis-indolylquinone of formula V is further reacted with an alkali metal hydroxide to give a bis-indol-2,5-dihydroxy-1,4-quinone. Preferred alkali metal hydroxides are sodium and potassium hydroxide, or mixtures thereof. Preferably, this reaction is carried out in a mixture of ethanol and tetrahydrofuran using concentrated aqueous KOH at a reflux temperature of about 85° C. for up to 20 hours. The bis-indol-2,5-dihydroxy-1,4-quinones prepared in this manner may be isolated according to standard workup and purification procedures as described above.

In other embodiments, the methods of the present invention comprise reacting a symmetrical compound of formula V wherein $R_1$ and $R_2$ are Br, or an asymmetrical compound of formula III wherein $R_1$ and $R_2$ are Br, with an alkali metal hydroxide and an alcohol of the formula R'OH wherein R' is lower alkyl or alkylaryl, to a produce symmetrical indolylquinone of the formula V wherein $R_1$ is $OR_1'$ and $R_2'$ is $OR_2'$, wherein $R_1'$ and $R_2'$ are each independently lower alkyl or alkylaryl; or an asymmetrical indolylquinone of formula III, wherein $R_1$ is $OR_1'$ and $R_2$ is $OR_2'$, wherein $R_1'$ and $R_2'$ are each independently lower alkyl or alkylaryl.

Specific compounds which can be made according to the methods of the present invention are described by formula IX below. $R_1$–$R_{12}$ of the formula can be as listed in Table I following the formula. Illustrative preparations of these compounds are found in the working examples.

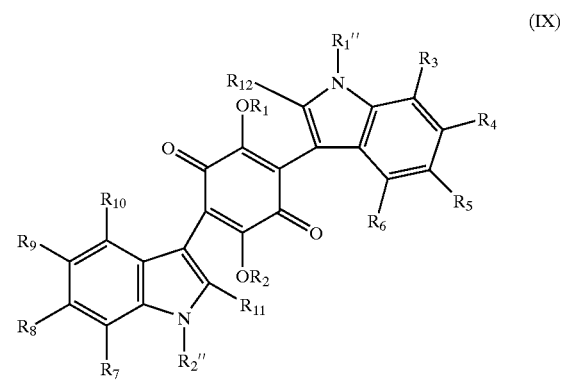

(IX)

TABLE 1

| Ex. | Compound | $R_1 = R_2$ | $R_{11}$ | $R_{12}$ | $R_1''$, $R_2''$, $R_3$–$R_{10}$ |
|---|---|---|---|---|---|
| 5.1.1 | 1 | H | 3-methyl-n-butyl | 3-methyl-n-butyl | |
| 5.1.2 | 1 | H | 3-methyl-n-butyl | 3-methyl-n-butyl | |
| 5.1.3 | 2 | H | n-butyl | n-butyl | |
| 5.1.4 | 3 | H | methyl | methyl | |
| 5.1.5 | 4 | H | 2-methylbut-2-en-4-yl | 2-methylbut-2-en-4-yl | |
| 5.1.6 | 5 | Ac | 2-methylbut-2-en-4-yl | 2-methylbut-2-en-4-yl | |
| 5.1.7 | 6 (e) | Ac | 3-methyl-n-butyl | 3-methyl-n-butyl | |
| 5.1.8 | 1 | H | 3-methyl-n-butyl | 3-methyl-n-butyl | |
| 5.1.9 | 7 | H | H | H | $R_5 = R_9 = Br$ |
| 5.1.10 | 8 | H | allyl | allyl | |
| 5.1.11 | 9 | H | n-propyl | n-propyl | |
| 5.1.12 | 10 | H | aminocarbonyl | aminocarbonyl | |
| 5.1.13 | 11 | Ac | aminocarbonyl | aminocarbonyl | |
| 5.1.14 | 12 | benzoyl | allyl | allyl | |
| 5.1.15 | 13 | H | cyano | cyano | |
| 5.1.16 | 14 | H | H | H | $R_6 = R_{10} =$ methoxycarbonyl |
| 5.1.17 | 15 | H | H | H | $R_3 = R_5 = R_7 = R_9 =$ methoxy |
| 5.1.18 | 16 | H | H | H | $R_3 = R_6 = R_7 = R_{10} =$ methoxy |
| 5.1.19 | 17 | H | H | H | $R_5 = R_9 =$ nitro |
| 5.1.20 | 18 | H | H | H | $R_6 = R_{10} =$ 4-chlorobenzoylamino |
| 5.1.21 | 19 | H | 4-chlorophenyl | 4-chlorophenyl | |
| 5.1.22 | 20 | H | 4-fluorophenyl | 4-fluorophenyl | |
| 5.1.23 | 21 | H | H | H | $R_4 = R_6 = R_8 = R_{10} =$ methoxy |
| 5.1.24 | 22 | H | H | H | $R_4 = R_5 = R_8 = R_9 =$ methoxy |
| 5.1.25 | 23 | H | H | H | $R_6 = R_{10} =$ cyano |
| 5.1.26 | 24 | H | H | H | $R_5 = R_9 =$ trifluoromethylphenylaminocarbonyl |
| 5.1.27 | 25 | H | 4-trifluoromethyl phenylaminocarbonyl | 4-trifluoromethyl phenylaminocarbonyl | |

TABLE 1-continued

| Ex. | Compound | $R_1 = R_2$ | $R_{11}$ | $R_{12}$ | $R_1''$, $R_2''$, $R_3$–$R_{10}$ |
|---|---|---|---|---|---|
| 5.1.28 | 26 (c) | H | ethyl | ethyl | |
| 5.1.29 | 27 | H | H | H | $R_4 = R_8 = NO_2$<br>$R_5 = R_9 = Br$ |
| 5.1.30 | 28 | Me | 2-methylbut-2-en-4-yl | 2-methylbut-2-en-4-yl | |
| 5.1.31 | 29 | Me | 3-methyl-n-butyl | 3-methyl-n-butyl | |
| 5.1.32 | 1 (b) | H | 3-methyl-n-butyl | 3-methyl-n-butyl | |
| 5.1.33 | 3 (a) | H | methyl | methyl | |
| 5.1.34 | 26 | H | ethyl | ethyl | |
| 5.1.35 | 2 (d) | H | n-butyl | n-butyl | |
| 5.1.36 | 31 | H | but-1-en-4-yl | but-1-en-4-yl | |
| 5.1.37 | 32 | H | 4-methyl-n-pentyl | 4-methyl-n-pentyl | |
| 5.1.38 | 33 (k) | H | 2-phenylethyl | 2-phenylethyl | |
| 5.1.39 | 34 | H | H | 3-methyl-n-butyl | |
| 5.1.40 | 35 | H | ethyl | ethyl | $R_5 = R_9 = $ carboxy |
| 5.1.41 | 36 | H | n-propyl | n-propyl | $R_5 = R_9 = $ carboxy |
| 5.1.42 | 37 | H | 3-methyl-n-butyl | 3-methyl-n-butyl | $R_5 = R_9 = $ carboxy |
| 5.1.43 | 38 | H | 4-carboxy-n-butyl | 4-carboxy-n-butyl | |
| 5.1.44 | 39 | H | H | 3-methyl-n-butyl | $R_5 = $ carboxy |
| 5.1.45 | 40 | H | ethyl | ethyl | $R_5 = R_9 = $ amino |
| 5.1.46 | 41 | H | n-propyl | n-propyl | $R_5 = R_9 = $ amino |
| 5.1.47 | 42 | H | 3-methyl-n-butyl | 3-methyl-n-butyl | $R_5 = R_9 = $ amino |
| 5.1.48 | 6 | acetyl | 3-methyl-n-butyl | 3-methyl-n-butyl | |
| 5.1.49 | 43 | H | ethyl | ethyl | $R_5 = R_9 = $ 4-methylphenyl-sulfonylamino |
| 5.1.50 | 44 | H | n-propyl | n-propyl | $R_5 = R_9 = $ 4-methylphenyl-sulfonylamino |
| 5.1.51 | 45 | H | 3-methyl-n-butyl | 3-methyl-n-butyl | $R_5 = R_9 = $ 4-methylphenyl-sulfonylamino |
| 5.1.52 | 46 | H | 2-methylbut-1-en-4-yl | 2-methylbut-1-en-4-yl | |
| 5.1.53 | 47 | H | 2-methylpent-2-en-5-yl | 2-methylpent-2-en-5-yl | |
| 5.1.54 | 48 (g) | H | phenyl | phenyl | |
| 5.1.55 | 49 | H | carboxy | carboxy | |
| 5.1.56 | 50 (f) | H | methyl | carboxy | |
| 5.1.57, 5.1.63 | 51 (i) | H | methyl | phenyl | |
| 5.1.58, 5.1.62 | 52 (h) | H | 3-methyl-n-butyl | phenyl | |
| 5.1.59 | 53 (j) | H | n-butyl | carboxy | |
| 5.1.60 | 54 | H | n-propyl | carboxy | |
| 5.1.61 | 55 | H | n-propyl | n-propyl | $R_4 = R_8 = $ carboxy |
| | 56 (l) | H | 3-methyl-n-butyl | carboxy | |
| 5.1.64 | 57 (m) | H | phenyl | carboxy | |
| | 58 (n) | H | carboxy | n-butyl | $R_9 = $ Cl |
| | 59 (o) | H | methyl | methyl | $R_5 = R_9 = $ methoxy |
| | 60 (p) | H | methyl | methyl | $R_5 = R_9 = $ Cl |
| | 61 (q) | H | methyl | carboxy | $R_5 = $ Cl<br>$R_9 = $ methoxy |
| | 62 (r) | H | naphthyl | naphthyl | |
| | 63 (s) | H | n-butyl | N-butylcarboxamido | |
| | 64 (t) | $CH_3$ | 3-methyl-n-butyl | 3-methyl-n-butyl | |
| | 65 (w) | $R_1 = H$<br>$R_2 = CH_3$ | 3-methyl-n-butyl | 3-methyl-n-butyl | |
| | 66 (u) | H | methyl | methyl | $R_1'' = CH_3$ |

TABLE 1-continued

| Ex. | Compound | $R_1 = R_2$ | $R_{11}$ | $R_{12}$ | $R_1'', R_2'', R_3$–$R_{10}$ |
|---|---|---|---|---|---|
| | 67 (v) | H | methyl | methyl | $R_1''$ = benzyl |

Unless otherwise indicated, $R_3$–$R_{10}$, $R_1''$ and $R_2''$ = hydrogen.

The mono-indolylquinone compounds which can be made according to the methods of the present invention are described by formula (IV) below. $R_1$–$R_7$ and $R_{30}$ can be as listed in Table 2 below.

TABLE 2

(IV)

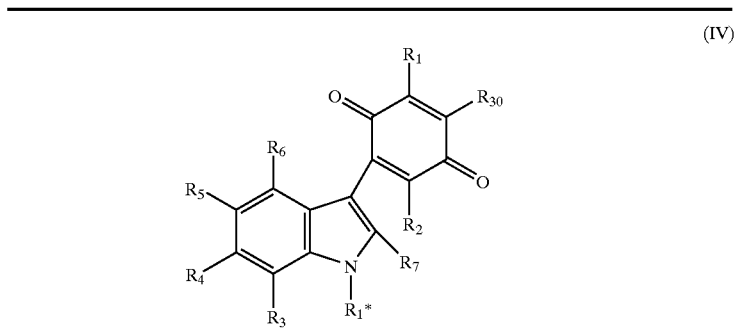

| Compound # | $R_1 = R_2 = R_{30}$ | $R_7$ | $R_3$–$R_6$ |
|---|---|---|---|
| (1a) | Br | 3-methyl-n-butyl | |
| (2a) | Br | n-butyl | |
| (3a) | Br | methyl | |
| (4a) | Br | 2-methylbut-2-en-4-yl | |
| (1a) | Br | 3-methyl-n-butyl | |
| (7a) | Br | H | $R_5$ = Br |
| (8a) | Br | allyl | |
| (9a) | Br | n-propyl | |
| (10a) | Br | aminocarbonyl | |
| (13a) | Br | cyano | |
| (14) | Br | H | $R_6$ = methoxycarbonyl |
| (15a) | Br | H | $R_3 = R_6$ = methoxy |
| (17a) | Br | H | $R_5$ = nitro |
| (18a) | Br | H | $R_6$ = 4-chlorobenzoylamino |
| (19a) | Br | 4-chlorophenyl | |
| (20a) | Br | 4-fluorophenyl | |
| (21a) | Br | H | $R_4 = R_6$ = methoxy |
| (22a) | Br | H | $R_4 = R_5$ = methoxy |
| (23a) | Br | H | $R_6$ = cyano |
| (24a) | Br | H | $R_5$ = trifluoro-methylphenylaminocarbonyl |
| (25a) | Br | 4-trifluoromethyl-phenylaminocarbonyl | |
| (26a) | Br | ethyl | |
| (27a) | Br | H | $R_4 = NO_2$; $R_5$ = Br |
| (1a) | Br | 3-methyl-n-butyl | |
| (31a) | Br | but-1-en-4-yl | |
| (32a) | Br | 4-methyl-n-pentyl | |
| (33a) | Br | 2-phenylethyl | |
| (34a) | Br | H | |
| (35a) | Br | ethyl | $R_5$ = carboxy |
| (36a) | Br | n-propyl | $R_5$ = carboxy |
| (37a) | Br | 3-methyl-n-butyl | $R_5$ = carboxy |
| (38a) | Br | 4-carboxy-n-butyl | |
| (39a) | Br | H | $R_5$ = carboxy |
| (40a) | Br | ethyl | $R_5$ = amino |
| (41a) | Br | n-propyl | $R_5$ = amino |
| (42a) | Br | 3-methyl-n-butyl | $R_5$ = amino |
| (43a) | Br | ethyl | $R_5$ = 4-methylphenyl-sulfonylamino |
| (44a) | Br | n-propyl | $R_5$ = 4-methylphenyl-sulfonylamino |
| (45a) | Br | 3-methyl-n-butyl | $R_5$ = 4-methylphenyl-sulfonylamino |

TABLE 2-continued (IV)

Compound # $R_1 = R_2 = R_{30}$   $R_7$                     $R_3-R_6$

| Compound # | $R_1 = R_2 = R_{30}$ | $R_7$ | $R_3-R_6$ |
|---|---|---|---|
| (46a) | Br | 2-methylbut-1-en-4-yl | |
| (47a) | Br | 2-methylpent-2-en-5-yl | |
| (48a) | Br | phenyl | |
| (49a) | Br | carboxy | |
| (55a) | Br | n-propyl | $R_4 = R_8$ = carboxy |

Unless otherwise indicated, $R_3-R_6$ = hydrogen.

As mentioned above, the compounds of Tables 1 and 2 have therapeutic activity for example as antifungal agents, antibacterial agents, modulators of cell proliferative disorders (e.g., antitumor agents), GRB-2 inhibitors, and insulin mimetics. In addition, these compounds may be useful in the dye industry.

5. EXAMPLES

In this section, examples of the methods described above are provided for illustration only and not by way of limitation. The reactants and starting materials are either readily synthesized or purchased from commercial sources.

5.1 EXAMPLE

Synthesis of Indolylquinone Compounds

Example 5.1.1

2,5-Dihydroxy-3,6-di-[2-(3-methyl-n-butyl)indol-3-yl]-1,4-quinone

1) Into a 250 ml round bottom flask, equipped with a magnetic stir bar, was placed 2-(3-methyl-n-butyl) indole (2.95 g), cesium carbonate (10.3 g) bromanil (3.34 g), and acetonitrile (79 ml). The mixture was stirred at room temperature for 45 hours. Following dilution with 1 N hydrochloric acid (250 ml), the crude mixture was extracted with ethyl acetate (500 ml). The organic layer was washed with brine (200 ml) and dried with sodium sulfate. After removal of solvent under reduced pressure, the crude residue was filtered through a short plug of flash silica, eluting with 20% ethyl acetate/hexane. The solvent was removed under reduced pressure, and the residue was purified by flash chromatography (15% ethyl acetate/hexane) to yield 2,5-dibromo-3,6-di-[2-(3-methyl-n-butyl)indol-3-yl]-1,4-quinone (553 g, 11%) as a blue crystalline solid.

Note: When the reaction was performed on 27.2 mg of starting indole, 95 mg cesium carbonate, 31 mg bromanil and 0.72 ml acetonitrile, the reaction was complete after 1.5 hours, and the product yield was 28%.

2) To a stirred solution of 2,5-dibromo-3,6-di-[2-(3-methyl-n-butyl)indol-3-yl]-1,4-quinone (553 mg), ethanol (9 ml), and tetrahydrofuran (9 ml) in a 100 ml round bottom flask equipped with a reflux condenser was added 2N aqueous potassium hydroxide solution (9 ml). The mixture was heated at 85° C. for 13 hours, followed by dilution with 1N aqueous sodium hydroxide solution (150 ml). The mixture was washed with 3:1 hexane/ethyl acetate (400 ml). After setting aside the aqueous layer, the organic layer was washed with another portion of 1N aqueous sodium hydroxide solution (150 ml) and then discarded. The basic aqueous layers were combined, acidified by adding 6N hydrochloric acid (60 ml), and extracted with ethyl acetate (300 ml). The organic layer was washed with brine (100 ml) and dried with sodium sulfate. Removal of solvent afforded 345 mg (78%) of 2,5-Dihydroxy-3,6-di-[2-(3-methyl-n-butyl)indol-3-yl]-1,4-quinone as a reddish-purple crystalline solid.

3) Preparation of 2-(3-methyl-n-butyl)-indole.

Carbonyldiimidazole (65 g) was mixed with 500 ml of dry dichloromethane in a 2-L round bottom flask and stirred magnetically. A solution of 4-methylvaleric acid in 200 ml of dichloromethane was added dropwise over 45 minutes and the mixture was stirred for another 1.25 hours. o-Toluidine (45 g) in 100 ml of dichloromethane was then added over about 20 minutes. After stirring for 2 hours the mixture was washed with water and then the solvent was stripped on a rotary evaporator. The residue was mixed with 150 ml of methanol and 75 ml of water and put in the freezer. Filtration of the precipitate, dilution of the filtrate with water and refiltration of the precipitate gave 75 g (94%) of vacuum dried N-(2-methylphenyl)-4-methylvaleramide which was used without further treatment in the next step.

The following procedure is cited in *Bull. Soc. Chim. Fr.* (37):190 (1925). N-(2-methylphenyl)-4-methylvaleramide (20.5 g), sodium amide (90%) (11.0 g), and tetralin (100 ml) were mixed in a 500 ml round bottom flask equipped with a magnetic stirrer and reflux condenser and heated at reflux for 2 hours. After cooling to room temperature, ethanol (10 ml) was added, followed by H$_2$O (150 ml). The layers were separated, the organic layer was filtered through a pad of anhydrous magnesium sulfate, and the solution was placed in a 200 ml round bottom flask equipped with a 10-inch vacuum jacketed Vigreux column. Tetralin was distilled at 35–45° C./0.5 mm Hg. The residue was transferred to a 50 ml round bottom flask equipped with a 4-inch Vigreux column, and distillation at 118–129° C./0.5 mm Hg provided 2-(3-methyl-n-butyl)-indole 13.1 g (70%) as a slightly yellow solid.

Example 5.1.2
2,5-Dihydroxy-3,6-di-[2-(3-methyl-n-butyl)indol-3-yl]-1,4-quinone (larger scale)

1) Into a 250 ml round bottom flask, equipped with a magnetic stir bar, was placed 2-(3-methyl-n-butyl)indole (30.0 g), cesium carbonate (62.6 g) bromanil (27.2 g), and acetonitrile (64 ml). The mixture was stirred at room temperature for 20 hours. Following dilution with 1N hydrochloric acid (500 ml), the crude mixture was extracted with ethyl acetate (1 L). The organic layer was washed with brine (400 ml) and dried with sodium sulfate. The solvent was removed under reduced pressure, the residue was purified by flash chromatography (30% ethyl acetate/hexane) to yield a 1:1 mixture of the desired product, 2,5-dibromo-3,6-di-[2-(3-methyl-n-butyl)indol-3-yl]-1,4-quinone and the undesired by-product, 2,6-dibromo-3,5-di-[2-(3-methyl-n-butyl)indol-3-yl]-1,4-quinone (42.3 g, 46% yield of desired product by HPLC) as a blue crystalline solid.

2) To a stirred solution of 1:1 mixture of 2,5-dibromo-3,6-di-[2-(3-methyl-n-butyl)indol-3-yl]-1,4-quinone and 2,6-dibromo-3,5-di[2-(3-methyl-n-butyl)indol-3-yl]-1,4-quinone (42.3 g), ethanol (166 ml), and tetrahydrofuran (166 ml) in a 1 L 3-necked round bottom flask equipped with a reflux condenser was added 4N aqueous potassium hydroxide solution (166 ml). The mixture was heated at 85° C. for 10 hours, followed by dilution with 1N hydrochloric acid (500 ml). The mixture was extracted with ethyl acetate (1 L). The organic layer was washed with brine (250 ml) and dried with sodium sulfate. Removal of solvent afforded 35.1 g of crude (about 50% pure) 2,5-Dihydroxy-3,6-di-[2-3-methyl-n-butyl)indol-3-yl]-1,4-quinone to be purified by HPLC.

In a separate experiment, purification of about 20 g of the crude product (about 50% pure) by HPLC resulted in 5 g of 2,5-Dihydroxy-3,6-di-[2-(3-methyl-n-butyl)indol-3-yl]-1,4-quinone with a purity of 97%.

Example 5.1.3
2,5-Dihydroxy-3,6-di-(2-n-butyl-indol-3-yl)-1,4-quinone

This compound was synthesized in the same manner as Example 2 except the starting indole was 2-n-butyl-indole. Preparation of 2-n-butyl-indole o-Toluidine (55 g) was mixed with 100 ml dry pyridine and 200 ml dry tetrahydrofuran in a 1-L 3-necked round bottom flask fitted with a Trubore stirrer, thermometer and a dropping funnel, under nitrogen. Then, with cooling in a refrigerated bath, valeryl chloride (60.3 g) was added dropwise over 1 hour. The mixture was stirred for another hour at room temperature and then poured onto 500 g ice and water. The precipitate was washed repeatedly with water on a Buchner funnel. The precipitate (88.9 g, 93%) was cyclized according to Verley and Bedure, 1925, *Bull. Soc. Chim. Fr.* (37): 190 to afford 2-n-butyl indole (67.4 g, 84%) as a very slightly yellow oil.

Example 5.1.4
2,5-Dihydroxy-3,6-di-[2-methyl-indol-3-yl]-1,4-quinone

This compound was synthesized in the same manner as Example 2 except the reaction time was 24 hours.

Example 5.1.5
2,5-Dihydroxy-3,6-di-[2-(2-methylbut-2-en-4-yl)indol-3-yl]1,4-quinone This compound may be synthesized as follows:

A mixture of 100 mg of 2,5-diacetoxy-3,6-dibromo-1,4-quinone, 180 mg of 3-[2-(2-methylbut-2-en-4-yl)indole, prepared by the Fisher indole synthesis, 10 ml of anhydrous dimethylforamide, and powdered potassium carbonate, is heated at 100° C. for 24 hours. The cooled mixture is partitioned between ethyl acetate and water. The ethyl acetate layer is then washed with brine, dried over sodium sulfate, filtered and concentrated. The crude product is then purified on a medium pressure liquid chromatography column in a solvent mixture of dichloromethane and methanol to provide 25 mg of 2,5-diacetoxy-3,6-di-[2-(2-methylbut-2-en-4-yl)indol-3-yl]1,4-quinone. 2,5-Diacetoxy-3,6-di-[2(2-methylbut-2-4-yl)indol-3-yl]1,4-quinone is then hydrolysed with 1 N aqueous sodium hydroxide solution in methanol. Acidification of the above mixture produces the crude product after filtration. Further crystallization in ethanol and water produces the title compound.

Other suitably protected quinones such as 3,6-dibromo-2,5-ditrimethylsiloxy-1,4-quinone, 3,6-dibromo-2,5-di-(t-butyldimethylsiloxy-1,4-quinone, 2,5-dibenzoxy-3,6-dibromo-1,4-quinone, 3,6-dibromo-2,5-diisobutyroxy-1,4-quinone, 2,5-dibenzyloxy-3,6-dibromo-1,4-quinone or 2,5-diallyoxycarbonyloxy-3,6-dibromo-1,4-quinone which can be prepared from commercially available 2,4-dibromo-3,6-dihydroxy-1,4-quinone may also be used as starting materials. These protecting groups can be removed by conventional deprotection methods such as diluted acid, potassium fluoride or palladium (0) complex or palladium on carbon with hydrogen or by methods described by Greene and Wuts (1991, "Protective Groups In Organic Synthesis," John Wiley and Son). Other solvents such as pyridine or dimethylsulfoxide (DMSO) may be used in place of dimethyl formamide.

Example 5.1.6
2,5-Diacetoxy-3,6-di-[2-(2-methylbut-2-en-4-yl)indol-3-yl]1,4-quinone (compound (e))

2,5-Diacetoxy-3,6-di-[2-(2-methylbut-2-en-4-yl)indol-3-yl]1,4-quinone is prepared as in Example 5.

Example 5.1.7
2,5-Diacetoxy-3,6-di-[2(3-methyl-n-butyl)indol-3-yl]1,4-quinone Hydrogenation of 2,5-diacetoxy-3,6-di-[2-(2-methylbut-2-en-4-yl)indol-3-yl]1,4-quinone methanol with 5% palladium on carbon under 1 atmosphere of hydrogen produced the title compound.

Example 5.1.8
2,5-Dihydroxy-3,6-di-[2-(3-methyl-n-butyl)indol-3-yl]1,4-quinone Base hydrolysis of 2,5-diacetoxy-3,6-di-[2-(3-methyl-n-butyl)indol-3-yl]1,4-quinone as described in Example 5 produced the title compound.

Under similar conditions as those described in Examples 5 to 8, the following compounds are prepared using either 2,5-dibromo-3,6-dihydroxy-1,4-quinone or 2,3,5,6-tetrabromoquinone as starting materials:

Example 5.1.9
3,6-Di-[5-(bromo)indol-3-yl]-2,5-dihydroxy-1,4-quinone

Example 5.1.10
3,6-Di-[2-(allyl)indol-3-yl]-2,5-dihydroxy-1,4-quinone

Example 5.1.11
2,5-Dihydroxy-3,6-di-[2-(n-propyl)indol-3-yl]1,4-quinone

This compound was prepared under conditions similar to those described in Examples 5 to 8.

Example 5.1.12
3,6-Di-[2-(aminocarbonyl)indol-3-yl]-2,5-dihydroxy-1,4-quinone

Example 5.1.13
2,5-Diacetoxy-3,6-di-[2(aminocarbonyl)indol-3-yl]-1,4-quinone

Example 5.1.14
3,6-Di-[2-allylindol-3-yl]-2,5-dibenzoyloxy-1,4-quinone

Example 5.1.15
2,5-Dihydroxy-3,6-di-[2-(cyano)indol-3-yl]1,4-quinone

Example 5.1.16
2,5-Dihydroxy-3,6-di-[4-(methoxycarbonyl)indol-3-yl]1,4-quinone

Example 5.1.17
2,5-Dihydroxy-3,6-di-[5,7-(dimethoxy)indol-3-yl]1,4-quinone

Example 5.1.18
2,5-Dihydroxy-3,6-di-[4,7-(dimethoxy)indol-3-yl]1,4-quinone

Example 5.1.19
2,5-Dihydroxy-3,6-di-[5-(nitro)indol-3-yl]1,4-quinone

Example 5.1.20
3,6-di-[4(4-chlorobenzoylamino)indol-3-yl]-2,5-dihydroxy-1,4-quinone

Example 5.1.21
3,6-di-[2-(4-chlorophenyl)indol-3-yl]-2,5-dihydroxy-1,4-quinone

Example 5.1.22
2,5-Dihydroxy-3,6-di-[2-(4-fluorophenyl)indol-3-yl]1,4-quinone

Example 5.1.23
2,5-Dihydroxy-3,6-di-[4,6-(dimethoxy)indol-3-yl]1,4-quinone

Example 5.1.24
2,5-Dihydroxy-3,6-di-[2-(5-hydroxy-6-methoxy)indol-3-yl]1,4-quinone

Example 5.1.25
2,5-Dihydroxy-3,6-di-[4-(cyano)indol-3-yl]1,4-quinone

Example 5.1.26
2,5-Dihydroxy-3,6-di-[5-(4-trifluoromethylphenylaminocarbonyl)indol-3-yl]1,4-quinone

Example 5.1.27
2,5-Dihydroxy-3,6-di-[2-(4-trifluoromethylphenylaminocarbonyl)indol-3-yl]1,4-quinone

Example 5.1.28
2,5-Dihydroxy-3,6-di-[2-(ethyl)indol-3-yl]1,4-quinone (compound (c))

This compound was prepared under conditions similar to those described in Examples 5 to 8.

Example 5.1.29
3,6-di-[2-(5-bromo-6-nitro)indol-3-yl]-2,5-dihydroxy-1,4-quinone

Example 5.1.30
2,5-Dimethoxy-3,6-di-[2-(2-methylbut-2-en-4-yl)indol-3-yl]1,4-quinone Methylation of Example 5 with methyl iodide and potassium carbonate in dimethylformamide followed by purification produces the title compound. This compound may also be prepared by heating 2,5-dibromo-3,6-di[2-(2-methylbut-2-en-4-yl)indol-3-y]1,4-quinone in methanol in the presence of powdered potassium carbonate.

Example 5.1.31
2,5-Dimethoxy-3,6-di-[2(3-methyl-n-butyl)indol-3-yl]1,4-quinone Hydrogenation of Example 30 under conditions as those in Example 3 produced the title compound.

Example 5.1.32
Preparation of 2,5-Dihydroxy-3,6-di-[2-(3-methyl-n-butyl)indol-3-yl]-1,4-quinone (compound (b))

To a glass tube containing 2-(3-methyl-n-butyl)indole (400 mg), bromanil (431 mg) and potassium carbonate (703 mg), equipped with a magnetic stir bar, was added dimethylformamide (10 ml). The mixture was stirred at room temperature for 40 hours. Following dilution with 1N hydrochloric acid (100 ml), the crude mixture was extracted with ethyl acetate (200 ml). The organic layer was washed with brine (100 ml) and dried with sodium sulfate. After removal of solvent under reduced pressure, the crude residue was filtered through a short plug of flash silica, eluting with 30% ethyl acetate/hexane. The solvent was removed under reduced pressure, and the residue was purified by flash chromatography (15% ethyl acetate/hexane) to yield 2,5-dibromo-3,6-di-[2-(3-methyl-n-butyl)indol-3-yl]-1,4-quinone (40 mg, 7%) as a blue crystalline solid.

To a stirred solution of 2,5-dibromo-3,6-di-[2-(3-methyl-n-butyl)indol-3-yl]-1,4-quinone (40 mg) in methanol (1.5 ml) was added 2N methanolic sodium hydroxide (0.251 ml). The solution was stirred at room temperature for 24 hours, followed by dilution with water (50 ml). The product was extracted with ethyl acetate (100 ml), washed with brine (50 ml) and dried with sodium sulfate. Removal of solvent under reduced pressure provided 2,5-methoxy-3,6-di-[2-(3-methyl-n-butyl)indol-3-yl]-1,4-quinone (30 mg, 90%) as a yellow crystalline solid.

To a stirred solution of 2,5-dimethoxy-3,6-di-[2-(3-methyl-n-butyl)indol-3-yl]-1,4-quinone (9 mg) in ethanol (2 ml) was added 1 N aqueous potassium hydroxide (1 ml). The mixture was heated at 85° C. for 3.5 hours, then diluted with 1 N hydrochloric acid (25 ml). The product was extracted with ethyl acetate (50 ml), washed with brine (25 ml) and dried with sodium sulfate. The solvent was removed under reduced pressure to afford 2,5-dihydroxy-3,6-di-[2-(3-methyl-n-butyl)indol-3-yl]-1,4-quinone (8 mg) as a reddish-brown crystalline solid.

5.1.32a) Preparation of 2-(2-methyl-1-buten-4-yl)indole.

To a stirred solution of 2-methylindole (1 g) in diethyl-ether (76 ml) under nitrogen was added a 1.6 M solution of n-butyllithium in hexane (14.3 ml) slowly dropwise via syringe. Potassium tert-butoxide (1.711 g) was then added, producing a bright yellow mixture. After stirring at room temperature under nitrogen for 50 minutes, the mixture was cooled to −78° C., whereupon 3-bromo-2-methylpropene (1.54 ml) was added dropwise via syringe, giving a red-orange solution. The reaction mixture was stirred at −78° C. for 2 hours, then quenched with water (10 ml). After warming to room temperature, water (150 ml) and 1 N hydrochloric acid (1 ml) was added to neutralize the reaction mixture. The mixture was extracted with ethyl acetate (250 ml), and the organic layer was washed with brine (100 ml) and dried with sodium sulfate. The solvent was removed under reduced pressure, and the crude residue was purified by flash chromatography (4% ethyl acetate/hexane) to afford 2-(2-methyl-1-butene-4-yl)indole (664 mg. 47%) as a waxy yellow solid.

5.1.32b) This indole is preferably synthesized by the method of Example 1.

However, this indole may also be prepared as follows:

Preparation of 2-(3-methyl-n-butyl)indole

Into a 3-necked round bottom flask under a blanket of nitrogen was placed 5% palladium catalyst on charcoal (771 mg). A solution of 2-(2-methyl-1-buten-4-yl) indole (671 mg) in ethanol (36 ml) was added to the flask, which was evacuated and charged with hydrogen twice. The mixture was stirred vigorously under hydrogen (1 atmosphere) for 2 hours, followed by filtration through a pad of Celite. The solvent was removed under reduced pressure and the crude residue was purified by flash chromatography (3% ethyl acetate/hexane) to give 2-(3-methyl-n-butyl)indole (400 mg, 59%) as a yellow crystalline solid.

Example 5.1.33

Preparation of 2,5-Dihydroxy-3,6-di-[2-(methyl)indol-3-yl]-1,4-quinone (compound (a))

This compound is preferably synthesized by the method of Example 2 using 2-methylindole as the starting indole. However, this compound may also be prepared by the method of Example 32 using 2-methylindole as the starting indole.

Example 5.1.34

Preparation of 3,6-Di-(2-ethylindol-3-yl)-2,5-dihydroxy-1,4-quinone

This compound is preferably synthesized by the method of Example 2 using 2-ethylindole as the starting indole. However, this compound may also be prepared by the method of Example 32 using 2-ethylindole as the starting indole. Preparation of 2-ethylindole: Refer to 32a) using methyl iodide as the alkylating agent.

Example 5.1.35

Preparation of 3,6-Di-(2-butylindol-3-yl) 2,5-dihydroxy-1,4-quinone (compound (d)): This compound is preferably synthesized by the method of Example 2 using 2-butylindole as the starting indole. Preparation of 2-butylindole: Refer to Example 3. However, this compound may also be prepared by the method of Example 32 using 2-butylindole as the starting indole. Preparation of 2-(but-1-en-4-yl)indole: Refer to 32a) using allyl bromide as the alkylating agent. Preparation of 2-butylindole: Refer to 32b) using 2-(but-1-en-4-yl) indole as the starting material.

Example 5.1.36

Preparation of 3,6-Di-[2-(but-1-en-4-yl)indol-3-yl]2,5-dihydroxy-1,4-quinone

This compound is preferably synthesized by the method of Example 2 but may also be prepared according to the method of Example 32 using 2-(but-1-en-4-yl)indole as the starting indole.

Example 5.1.37

Preparation of 2,5-Dihydroxy-3,6-di-[2-(4-methyl-n-pentyl)indol-3-yl]-1,4-quinone: This compound is preferably synthesized by the method of Example 2 but may also be prepared according to Example 32 using 2-(4-methyl-n-pentyl)indole as the starting indole. Preparation of 2-(2-methyl-2-penten-5-yl)indole: Refer to Example 1 using 5-methylhexanoic acid as the starting acid. This indole may also be prepared according to Example 32a) using 4-bromo-2-methyl-2-butene as the alkylating reagent. Preparation of 2-(4-methyl-n-pentyl)indole: Refer to 32b) using 2-(2-methyl-2-penten-5-yl)indole as the starting material.

Example 5.1.38

Preparation of 2,5-Dihydroxy-3,6-di-[2-(2-phenylethyl)indol-3-yl]-1,4-quinone (compound (k)): This compound is preferably synthesized by the method of Example 2 but may also be prepared according to Example 32 using 2-(2-phenylethyl)indole as the starting indole. Preparation of 2-(2-phenylethyl)indole: Refer to Example 3 using 3-phenylpropionyl chloride as the starting acid chloride. This indole may also be prepared according to Example 32a) using benzyl bromide as the alkylating agent.

Example 5.1.39

Preparation of 2,5-Dihydroxy-6-(indol-3-yl)-3-[2-(3-methyl-n-butyl)indol-3-yl]-1,4-quinone This synthesis is achieved by treating 2-(3-methyl-n-butyl)indole with 2 equivalents of bromanil in the presence of cesium carbonate in dimethylformamide, followed by workup and purification similar to Example 32. The resultant mono-indolyl adduct is optionally treated with 2 equivalents of indole under the same conditions as above to provide the bis-indolyl product.

Example 5.1.40

Preparation of 3,6-Di-(5-carboxy-2-ethylindol-3-yl)-2,5-dihydroxy-1,4-quinone: Refer to Example 32 using 5-carboxy-2-ethylindole as the starting indole. Preparation of 5-carboxy-2-ethylindole: Refer to Example 3 using methyl 4-amino-3-methylbenzoate and propionyl chloride as the starting compounds. The methyl ester is hydrolyzed upon workup of the cyclization to give 5-carboxy-2-ethylindole. This synthesis may also be accomplished beginning with 5-chloro-2-methylindole, which is alkylated with methyl indole. The product chloroindole is converted to its Grignard species and exposed to carbon dioxide to finish the synthesis.

Example 5.1.41

Preparation of 3,6-Di-[5-carboxy-2-(n-propyl)indol-3-yl]-2,5-dihydroxy-1,4-quinone:

Refer to Example 32 using 5-carboxy-2-propylindole as the starting indole. Preparation of 5-carboxy-2-propylindole: Refer to Example 1 using methyl 4-amino-3-methyl-benzoate instead of o-toluidine or refer to 40 using ethyl iodide as the alkylating agent.

Example 5.1.42

Preparation of 3,6-Di-[5-carboxy-2-(3-methyl-n-butyl)indol-3-yl]-2,5-dihydroxy-1,4-quinone Refer to Example 32 using 5-carboxy-2-(3-methyl-n-butyl)indole as the starting indole. Preparation of 5-carboxy-2-(2-methyl-1-buten-4-yl)indole:

Refer to 40 using 3-bromo-2-methylpropene as the alkylating agent.

Preparation of 5-carboxy-2-(3-methyl-n-butyl)indole: Refer to Example 1 using methyl 4-amino-3-methyl-benzoate instead of o-toluidine, or refer to Example 32b) using 5-carboxy-2-(2-methyl-1-buten-4-yl)indole as the starting material.

Example 5.1.43
Preparation of 3,6-Di-[2-(4-carboxy-n-butyl)indol-3-yl]-2,5-dihydroxy-1,4-quinone:

Refer to Example 32 using 2-(4-carboxy-n-butyl)indole as the starting indole. Preparation of 2-(4-carboxy-3-buten-1-yl)indole:

Refer to 32(a) using 4-bromo-2-butenoic acid as the alkylating agent. Preparation of 2-(4-carboxy-n-butyl) indole: Refer to Example 3 using methyl adipyl chloride as the acid chloride. The methyl ester was hydrolyzed in the cyclization workup to provide the product carboxyindole. In the alternative, refer to Example 32b) using 2-(4-carboxy-3-buten-1-yl) indole as the starting material.

Example 5.1.44
Preparation of 3-[5-Carboxy-2-(3-methyl-n-butyl)indol-3-yl]-2,5-dihydroxy-6-(indol-3-yl)-1,4-quinone Refer to Example 39 using 5-carboxy-2-(3-methyl-n-butyl)indole in the first step.

Example 5.1.45
Preparation of 3,6-Di-(5-amino-2-ethylindol-3-yl)-2,5-dihydroxy-1,4-quinone Refer to Example 32 using 5-amino-2-ethylindole as the starting indole. Preparation of 5-amino-2-ethylindole: Refer to Example 3 using 2-methyl-4-nitroaniline and propionyl chloride to give 5-nitro-2-ethylindole, which is reduced to the desired amino compound using catalytic hydrogenation as in 32b.

In the alternative, this synthesis may be accomplished with a standard nitration of 2-ethylindole using sodium nitrate and sulfuric acid similar to that cited in *Chem. Lett.* (7): 1125–1128 (1991). The resultant 5-nitro-2-ethylindole is reduced to the desired amino compound using catalytic hydrogenation as in 32b).

Example 5.1.46
Preparation of 3,6-Di-[5-amino-2-(n-propyl)indol-3-yl]-2,5-dihydroxy-1,4-quinone Refer to Example 32 using 5-amino-2-(n-propyl)indole as the starting indole. Preparation of 5-amino-2-(n-propyl)indole: Refer to Example 45 using butyryl chloride. In the alternative, refer to the synthesis cited in *Chem. Lett.* (7): 1125–1128 (1991) cited in Example 45 using 2-n-propylindole.

Example 5.1.47
Preparation of 3,6-Di-[5-amino-2-(3-methyl-n-butyl)indol-3-yl]2,5-dihydroxy-1,4-quinone Refer to Example 32 using 5-amino-2-(3-methyl-n-butyl)indole as the starting indole. Preparation of 5-amino-2-(3-methyl-n-butyl)indole: Refer to Example 1 using 2-methyl-4-nitroaniline instead of o-toluidine. The resultant 5-nitro-2-(3-methyl-n-butyl)-indole is reduced to the desired amino compound as in 32b. The synthesis may also be accomplished according to Example 45 using 2-(3-methyl-n-butyl) indole.

Example 5.1.48
Preparation of 2,5-Diacetoxy-3,6-di-[2-(3-methyl-n-butyl)indol-3-yl]-1,4-quinone This synthesis was accomplished by treating 2,5-hydroxy-3,6-di-[2-(3-methyl-n-butyl)indol-3-yl]-1,4-quinone with acetic anhydride in the presence of pyridine.

Example 5.1.49
Preparation of 3,6-Di-[2-ethyl-5-(4-methylphenylsulfonylamino)indol-3-yl]-2,5-dihydroxy-1,4-quinone Refer to Example 32 using 2-ethyl-5-(4-methylphenylsulfonylamino)indole as the starting indole. Preparation of 2-ethyl-5-(4-methylphenylsulfonylamino) indole: The above compound is synthesized by treating 5-amino-2-ethylindole with p-toluenesulfonyl chloride in the presence of triethylamine.

Example 5.1.50
Preparation of 2,5-Dihydroxy-3,6-di-[5-(4-methylphenylsulfonylamino)-2-(n-propyl)indol-3-y1]-1,4-quinone Refer to Example 32 using 5-(4-methylphenylsulfonylamino)-2-(n-propyl)indole as the starting indole. Preparation of 5-(4-methylphenylsulfonylamino)-2-(n-propyl)indole: Refer to 49 using 5-amino-2-propylindole.

Example 5.1.51
Preparation of 2,5-Dihydroxy-3,6-di-[2-(3-methyl-n-butyl)-5-(4-methylphenylsulfonylamino)indol-3-yl]-1,4-quinone Refer to Example 32 using 2-(3-methyl-n-butyl)-5-(4-methylphenylsulfonylamino) indole as the starting indole. Preparation of2-(3-methyl-n-butyl)-5-(4-methylphenylsulfonylamino)indole: Refer to 49 using 5-amino-2-(3-methyl-n-butyl)indole.

Example 5.1.52
Preparation of 2,5-Dihydroxy-3,6-di-[2-(2-methylbut-1-en-4-yl)indol-3-yl]-1,4-quinone Refer to Example 32 using 2-(2-methylbut-1-en-4-yl) indole as the starting indole.

Example 5.1.53
2,5-dihydroxy-2,6-di-[2-(2-methylpent-2-en-5-yl)-indol-3-yl]-1,4-quinone

Example 5.1.54
2,5-dihydroxy-3,6-di-(2-phenylindol-3-yl)-1,4-quinone (compound (g)): Refer to Example 2 using 2-phenylindole as the starting indole

Example 5.1.55
2,5-dihydroxy-3,6-di-(2-carboxyindol-3-yl)-1,4-quinone

Example 5.1.56
Preparation of 3-(2-carboxyindol-3-yl)-2,5-dihydroxy-6-(2-methylindol-3-yl)-1,4-quinone (compound (f)):

1) Into a 10 ml screw-cap glass tube was placed bromanil (1 g), cesium carbonate (2.3 g), ethyl indole-2-carboxylate (446 mg), and acetonitrile (2.36 ml). After stirring the mixture at room temperature for 3 hours, during which the mono-indolylquinone 6-(2-ethylcarboxyindol-3-yl)-2,3,5-tribromo-1,4-quinone was formed, 2-methylindole (464 mg) was added. The mixture was stirred at room temperature for 24 hours, after which 1 N hydrochloric acid (100 ml) was added. The aqueous layer was extracted with ethyl acetate (200 ml). The organic layer was washed with brine (100 ml) and dried with sodium sulfate. Following removal of the solvent under reduced pressure, the crude residue was purified by flash chromatography (30% ethyl acetate/hexane) to provide 2,5-dibromo-3-(2-ethylcarboxyindol-3-yl)-6-(2-methylindol-3-yl)-1,4-quinone (0.37 g) as a blue crystalline solid. Alternatively, the mono-indolylquinone 6-(2-ethylcarboxyindol-3-yl)-2,3,5-tribromo-1,4-quinone may isolated separately and used in further reactions with other indoles.

2) To a stirred solution of 2,5-dibromo-3-(2-ethylcarboxyindol-3-yl)-6-(2-methylindol-3-yl)-1,4-quinone (0.37 g), ethanol (1.6 ml), and tetrahydrofuran (1.6 ml) was added 4 N aqueous potassium hydroxide solution (1.6 ml). The mixture was heated at 85° C. for 10 hours, followed by dilution with 1N hydrochloric acid (75 ml). The mixture was extracted with ethyl acetate (150 ml). The organic layer was washed with brine (75 ml) and dried with sodium sulfate. Removal of solvent afforded 3-(2-carboxyindol-3-yl)-2,5-dihydroxy-6-(2-methylindol-3-yl)-1,4-quinone (0.258 g) as a reddish brown crystalline solid.

Example 5.1.57

Preparation of 2,5-dihydroxy-6-(2-methylindol-3-yl)-3-(2-phenylindol-3-yl)-1,4-quinone (compound (i)). This compound was prepared according to the procedure of Example 56. It doesn't matter what order the two indoles are added in—the same product is obtained.

Example 5.1.58

Preparation of 2,5-dihydroxy-6-[2-(3-methyl-n-butyl)indol-3-yl]-3-(2-phenylindol-3-yl)-1,4-quinone (compound (h)). This compound was prepared according to the procedure of Example 56. As in Example 57, the order of addition of the two indoles doesn't matter.

Example 5.1.59

Preparation of 6-[2-(n-butyl)-indol-3-yl]-3-(2-carboxyindol-3-yl)-2,5-dihydroxy-1,4-quinone (compound (0)). This compound was prepared according to the procedure of Example 56.

Example 5.1.60

Preparation of 3-(2-carboxyindol-3-yl)-2,5-dihydroxy-6-[2-(n-propyl)-indol-3-yl]-1,4-quinone. This compound was prepared according to the procedure of Example 56.

Example 5.1.61

Preparation of 3,6-di(6-carboxy-2-n-propylindol-3-yl)-2,5-dihydroxy-1,4-quinone: Refer to Example 2 using 6-carboxy-2-n-propylindole as the starting indole. Preparation of 6-carboxy-2-n-propylindole: Refer to Example 3 using methyl 3-amino-4-methylbenzoate and butyryl chloride as the starting compounds. The methyl ester was hydrolyzed upon workup of the cyclization to give 6-carboxy-2-n-propylindole.

Example 5.1.62

Preparation of 2,5-dihydroxy-6-[2-(3-methyl-n-butyl)indol-3-yl]-3-(2-phenylindol-3-yl)-1,4-quinone (compound (h))

A mixture of tetrabromo-1,4-benzoquinone (5 g, 11.8 mmol), 2-phenylindole (2.28 g, 1 equiv.) and cesium carbonate (11.53 g, 3 equiv.) in acetonitrile (12 mL) was stirred at room temperature for 3 hours. To the reaction mixture was then added 2-(3-methyl-butyl)-indole (3.32 g, 1.5 equiv.). After stirring at room temperature for 24 hours, tetrahydrofuran ("THF") (30 mL), ethyl alcohol ("EtOH") (30 mL) and 4N potassium hydroxide ("KOH") (30 mL) was added and the mixture was heated at 85° C. for 10 hours. The cooled reaction was acidified with 1N hydrochloric acid ("HCl") followed by extraction with ethyl acetate ("EtOAc"). After concentration, the residue was purified by high performance liquid chromatography ("HPLC") to give 2,5-dihydroxy-6-[2-(3-methyl-n-butyl)indol-3-yl]-3-(2-phenylindol-3-yl)-1,2-quinone as a purple crystalline solid.

$^1$H nuclear magnetic resonance ("$^1$H NMR") (360 MHz, dimethyl-$d_6$ sulfoxide) δ11.58 (br s, 1H, NH), 11.07 (br s, 1H, NH), 10.67 (br s, 2H, 2×OH), 7.65 (m, 2H), 7.44 (m, 2H), 7.29–7.4 (m, 4H), 7.2 (m, 1H), 7.14 (m, 1H), 7.0 (m, 2H), 6.92 (m, 1H), 2.6 (m, 2H, CH$_2$), 1.53 (m, 3H), 0.87 (d, J=6.5 Hz, 6H, 2×CH$_3$).

mass spectrometry ("MS") m/z (mass to charge ratio) 517 [M$^+$+1].

Example 5.1.63

Preparation of 2,5-dihydroxy-6-(2-methylindol-3-yl)-3-(2-phenylindol-3-yl)-1,4-quinone (compound (i))

A mixture of tetrabromo-1,4-benzoquinone (1.48 g, 3.5 mmol), 2-phenylindole (0.68 g, 1 equiv.) and cesium carbonate (3.43 g, 3 equiv.) in acetonitrile (4 mL) was stirred at room temperature for 3 hours. To the reaction mixture was then added 2-methylindole (0.69 g, 1.5 equiv.). After stirring at room temperature for 24 hours, THF (9 mL), EtOH (9 mL) and 4N KOH (9 mL) was added and the mixture was heated at 85° C. for 10 hours. The cooled reaction was acidified with 1N HCl followed by extraction with EtOAc. After concentration, the residue was purified by HPLC to give 2,5-dihydroxy-6-(2-methylindol-3-yl)-3-(2-phenylindol-3-yl)-1,4-quinone as a purple crystalline solid.

$^1$HNMR (360 MHz, dimethyl-$d_6$ sulfoxide) δ11.57 (br s, 1H, NH), 11.10 (br s, 1H, NH), 10.6 (br s, 2H, 2×OH), 7.67 (m, 2H), 7.43 (m, 3H), 7.3 (m, 3H), 7.2 (m, 1H), 7.14 (m, 1H), 7.03 (m, 2H), 6.92 (m, 1H), 2.27 (m, 3H, CH$_3$).
MS m/z 461 [M$^+$+1].

Example 5.1.64

Preparation of 3-(2-carboxyindol-3-yl)-2,5-dihydroxy-6-(2-phenylindol-3-yl)-1,4-quinone (compound (m))

A mixture of tetrabromo-1,4-benzoquinone (1.0 g, 2.36 mmol), ethyl indole-2-carboxylate (0.45 g, 1 equiv.) and cesium carbonate (2.31 g, 3 equiv.) in acetonitrile (3 mL) was stirred at room temperature for 3 hours. To the reaction mixture was then added 2-phenylindole (0.68 g, 1.5 equiv.). After stirring at room temperature for 24 hours, THF (6 mL), EtOH (6 mL) and 4N KOH (6 mL) was added and the mixture was heated at 85° C. for 10 hours. The cooled reaction was acidified with 1N HCl followed by extraction with EtOAc. After concentration, the residue was purified by HPLC to give 3-(2-carboxyindol-3-yl)-2,5-dihydroxy-6-(2-phenylindol-3-yl)-1,4-quinone as a purple crystalline solid.
MS m/z 490.9 [M$^+$+1].

5.2 Example

Inhibition EGFR/GRB-2 Interactions

In the Example presented in this Section, the compounds (h) 2,5-dihydroxy-6-[2-(3-methyl-n-butyl)indol-3-yl]-3-(2-phenylindol-3-yl)-1,4-quinone and (i) 2,5-dihydroxy-6-(2-methylindol-3-yl)-3-(2-phenylindol-3-yl)-1,4-quinone are demonstrated to effectively inhibit the binding of tyrosine phosphorylated EGF-receptor to a GRB-2 SH2 peptide domain in comparison to the compound (m) 3-(2-carboxyindol-3-yl)-2,5-dihydroxy-6-(2-phenylindol-3-yl)-1,4-quinone.

5.2.1 Materials and Methods

Adaptor-GST fusion protein. The adaptor-GST (glutathione-S-transferase) fusion proteins used herein were GRB-2-GST fusion proteins prepared by expression in *E. coli* transformed with GRB-2/pGEX constructs. The GRB-2 portions of these fusion proteins consisted of only the SH2 domain of the GRB-2 protein. Transformed cells are grown in Luria broth (LB) supplemented with ampicillin. After reaching an optical density (OD) at 600 nm of 0.3, the cells are induced for 6 hours with isopropyl β-D-thiogalactopyranoside (IPTG) in order to express the fusion protein.

After the 6 hour expression period, the cells are precipitated, pelleted at 10,000×g for 10 minutes at 4° C., washed, and resuspended in phosphate buffered saline (PBS). Next, the cells are lysed by sonication (6 strokes, 5 seconds per stroke). Insoluble material is removed by centrifugation at 10,000×g for 10 minutes at 4° C., and the supernatant is passed over a Glutathion-Sepharose column. Bound GRB-2-GST fusion protein is eluted off the column with 5 mM reduced glutathion, then dialyzed against PBS.

Immobilized EGF-R tyrosine kinase molecule. Epidermal growth factor receptor tyrosine kinase (EGF-R). EGF-R was isolated from cells overexpressing EGF-R, specifically, the A431 (ATCC CRL 1551), cell line. The cells are lysed in HNTG buffer (20 mM Hepes/HCl, pH 7.4, 150 mM NaCl, 1.0% Triton X-100, 5% glycerol, 1 mM phenylmethylsulfonyl fluoride (PMSF), 1 mg/l aprotinin, 1 mg/L leupeptin, 10 mg/L benzamidine).

EGF-R protein was isolated from the cell lysates by immobilization onto microtiter plates, as described below. EGF-R was subsequently phosphorylated in vitro, as explained below.

The EGF-R molecule was immobilized onto microtiter plates. Microtiter plates were prepared by first coating the wells of the plate, overnight at 4° C., with an anti-EGF-R monoclonal antibody directed against the extracellular domain of EGFR (UBI, #05–101) at a concentration of 0.5 $\mu$g (in PBS) per microtiter well, at a final volume of 150 $\mu$l per well. After overnight coating, the coating solution was removed from the microtiter wells, and replaced with blocking buffer (5% dry milk in PBS) for 30 minutes at room temperature, after which the blocking buffer is removed and the wells were washed 4 times with TBST buffer (150 mM NaCl, 50 mM Tris-HCl, pH 7.2, 0.1% Triton X-100).

Cell lysate from EGF-R-expressing cells were added to each well, in 150 $\mu$l of PBS, incubated 30 minutes at room temperature, with shaking. Unbound EGF-R was removed by washing wells 5 times with TBST buffer. Approximately 50–100 ng of EGF-R protein was bound per well.

It was important to use an EGF-R overexpressing cell line which exhibits a high endogenous phosphatase activity, such as the A431 cell line used herein. This is because during lysis and incubation with the immobilized antibody, the phosphatases remove phosphate groups from the EGF-R molecules, thus prohibiting endogenous adaptor proteins, such as GRB proteins, to bind EGFR, which could potentially lead to artifactual results. Alternatively, cells may be starved before lysis, if the cell line utilized may be readily starved.

Preparation of autophophorylated EGF-R. The following in vitro kinase reaction yielded autophosphorylated EGF-R. The kinase reaction was initiated by the addition of 15 $\mu$l of ATP/Mn$^{2+}$ mix (in 50 mM MnCl$_2$, final concentration of 10 $\mu$M ATP, for a total volume of 150 $\mu$l. The plate was incubated for 5 minutes at room temperature, shaking, the supernatant was aspirated, and the plates were then washed 5 times with TBST.

Assay procedure. Either 30 ng GRB-2-GST fusion proteins (i.e. a 1:1 ratio of EGF-R:GRB-2 proteins) or 5 ng GRB-2-GST fusion proteins (i.e. a 4:1 ratio of EGF-R:GRB-2 proteins) were added to the phosphorylated EGF-R coated microtiter wells in incubation buffer (0.1 M potassium phosphate buffer, pH 6.5) for 30 minutes, at room temperature, in the presence of Compound I. Control wells were incubated with GRB-2-GST fusion proteins in the absence of Compound I.

After incubation, wells were washed extensively with TBST. The amount of GRB-2-GST fusion protein bound to the immobilized EGF-R is then preferably determined by with a purified rabbit antiserum against the GST-moiety of the fusion protein (New Victoria, Australia; Catalog No. 00001605). Incubations were for 30 minutes at room temperature. After incubation, antibody was removed and the wells are washed extensively with TBST. For visualization, wells were next incubated with a TAGO goat-anti-rabbit peroxidase antibody at room temperature for 30 minutes. After incubation, the antibody was removed, the wells were washed with tap water, and then with TBST. Substrate solution, ABTS (2,2'-Azinobis(3-ethylbenzthiazolinesulfonic acid)/H$_2$O$_2$ (1.2 $\mu$l HH$_2$O$_2$ to 10 ml ABTS) was applied to the wells, and incubated for 20 minutes at room temperature. The reaction was stopped by addition of 5NH$_2$SO$_4$. The O.D. at 410 nm was determined for each well. Utilizing this technique, it is normally possible to detect as little as 2 ng GRB-2-GSI over background.

Alternatively, after incubation of the test substance and the GRB-2-GST fusion protein on the EGF-R wells, biotinylated monoclonal antibodies e.g., EL-6 or EL-12, may be utilized to assay fusion protein binding. The epitopes recognized by such antibodies map on the SH2 domain of GRB-2, but do not interfere with GRB-2 binding to phosphorylated EGFR. Binding of these antibodies is then determined by using a streptavidin-biotinylated horseradish peroxidase reactant.

Additionally, after incubation of the test substance and the GRB-2-GST fusion protein on the EGF-R wells, binding of the fusion protein to the immobilized EGFR may be assayed by incubating with 1 mM 1-chloro-2,4 dinitrobenzene (CDNB) and 1.54 mg/ml reduced glutathion in incubation buffer. The OD is then measured at 340 nm. This reaction is linear up to OD 1.0, and can be stopped with competitive GST inhibitors, as described in Mannervik and Danielson (Mannervik, B. and Danielson, U. H., 1988, CRC Critical Reviews in Biochemistry 23:238).

5.2.2 Results

The compounds (h) 2,5-dihydroxy-6-[2-(3-methyl-n-butyl)indol-3-yl]-3-(2-phenylindol-3-yl)-1,4-quinone, (i) 2,5-dihydroxy-6-(2-methylindol-3-yl)-3-(2-phenylindol-3-yl)-1,4-quinone, and (m) 3-(2-carboxyindol-3-yl)-2,5-dihydroxy-6-(2-phenylindol-3-yl)-1,4-quinone were tested for their ability to inhibit the binding of tyrosine phosphopilated EGF-receptor to an SH2 peptide domain of the GRB-2 adaptor protein, according to the assays described, above, in Section 5.2.1.

The compounds (h) 2,5-dihydroxy-6-[2-(3-methyl-n-butyl)indol-3-yl]-3-(2-phenylindol-3-yl)-1,4-quinone and (i) 2,5-dihydroxy-6-(2-methylindol-3-yl)-3-(2-phenylindol-3-yl)-1,4-quinone proved to be potent inhibitors of GRB-2/SH2 binding, having IC$_{50}$ values of 0.6 $\mu$M and 2.9 $\mu$M, respectively. In contrast, the compound (m) 3-(2-carboxyindol-3-yl)-2,5-dihydroxy-6-(2-phenylindol-3-yl)-1,4-quinone is a less potent inhibitor, with an IC$_{50}$ value of 22 $\mu$M. (IC$_{50}$, as used herein, refers to the concentration of test compound required to inhibit one-half of GRB-2/SH2 binding relative to the amount of binding which occurs in the absence of test compound.)

5.3 Example

Inhibition of Cellular Proliferation

The Example presented herein demonstrates that the compounds (h) 2,5-dihydroxy-6-[2-(3-methyl-n-butyl)

indol-3-yl]-3-(2-phenylindol-3-yl)-1,4-quinone, (i) 2,5-dihydroxy-6-(2-methylindol-3-yl)-3-(2-phenylindol-3-yl)-1,4-quinone of the invention are potent inhibitors of cellular proliferation, in comparison to compound (m) 3-(2-carboxyindol-3-yl)-2,5-dihydroxy-6-(2-phenylindol-3-yl)-1,4-quinone.

5.3.1 Materials and Methods

A431-Sulforhodamine B (SRB) Growth Assay. A431 (ATCC#CRL 1555) cells were seeded at 2000 cells/well in 96-well flat bottom plates in normal growth media, which was 10% FBS/RPMI supplemented with 2 mM glutamine. The plates of cells were incubated for about 24 hours at 37° C. The compound of formula III, the compound of formula IV and 3-[2,5-Dihydroxy-3,6-dioxo-4-(2-phenyl-1H-indol-3-yl)-cyclohexa-1,4-dienyl]-1H-indole-2-carboxylic acid were prepared at 2 times the desired highest final concentration and serially diluted in 0.5% FBS/RPMI growth media supplemented with 2 mM glutamine in a 96-well round bottom plate. Before each compound was transferred to the plates containing the cells, the normal growth media was removed and 0.5% FBS/RPMI supplemented with 2 mM glutamine was added to the cells. Plates then received an equal volume of compound dilution per well making the total volume per well 200 µl. DMSO serves as the vector control up to 0.2% as final concentration. The cells were then incubated at 37° C. in a humidified 5% $CO_2$ incubator. Four days following dosing of compound, the media was discarded and 200 µl/well of ice-cold 10% TCA (Trichloroacetic Acid) was added to fix cells. After 60 minutes at 4° C., the TCA was discarded and the plate was rinsed 5 times with water. The plate was then air-dried and 100 µl/well of 0.4% SRB (Sulforhodamine B from Sigma) 20 in 1% Acetic Acid was added to stain cells for 10 minutes at room temperature. The SRB was discarded and the plate was rinsed 5 times with 1% Acetic Acid. After the plate was completely dried, 100 µl/well of 10 mM Tris-base was added to solubilize the dye. After 5 to 10 minutes, the plate was read on a Dynatech ELISA Plate Reader at dual wavelengths at 570 nm and 630 mn.

5.3.2 Results

A431 cells, which overexpress EGF receptor, were contacted with (h) 2,5-dihydroxy-6-[2-(3-methyl-n-butyl)indol-3-yl]-3-(2-phenylindol-3-yl)-1,4-quinone, (i) 2,5-dihydroxy-6-(2-methylindol-3-yl)-3-(2-phenylindol-3-yl)-1,4-quinone, or (m) 3-(2-carboxyindol-3-yl)-2,5-dihydroxy-6-(2-phenylindol-3-yl)-1,4-quinone to test the effect the compounds on cell proliferation, utilizing the SRB protocols described, above, in Section 5.3.1.

The compounds (h) 2,5-dihydroxy-6-[2-(3-methyl-n-butyl)indol-3-yl]-3-(2-phenylindol-3-yl)-1,4-quinone and (i) 2,5-dihydroxy-6-(2-methylindol-3-yl)-3-(2-phenylindol-3-yl)-1,4-quinone have $IC_{50}$ values of 0.21 and 2.7 µM, respectively and therefore proved to be potent inhibitors of cell proliferation of A431 cells. In contrast, (m) 3-(2-carboxyindol-3-yl)-2,5-dihydroxy-6-(2-phenylindol-3-yl)-1,4-quinone was not a potent inhibitor of cell proliferation, having an $IC_{50}$ value of greater than 100 µM. $IC_{50}$, as used herein, refers to the concentration of test compound required to inhibit cell proliferation to 50% of the level seen in A431 cells which have not been contacted to the test compounds.

Thus, the results depicted in this Section demonstrate that the compounds (h) 2,5-dihydroxy-6-[2-(3-methyl-n-butyl)indol-3-yl]-3-(2-phenylindol-3-yl)-1,4-quinone and (i) 2,5-dihydroxy-6-(2-methylindol-3-yl)-3-(2-phenylindol-3-yl)-1,4-quinone act to inhibit cell proliferation. These results, taken together with those shown in the Example presented in Section 5.2, above, which demonstrated that the compounds (h) 2,5-dihydroxy-6-[2-(3-methyl-n-butyl)indol-3-yl]-3-(2-phenylindol-3-yl)-1,4-quinone and (i) 2,5-dihydroxy-6-(2-methylindol-3-yl)-3-(2-phenylindol-3-yl)-1,4-quinone act to inhibit adaptor protein binding to the SH2 domain of the protein tyrosine kinase receptor EGFR, indicate that these compounds act as cell growth inhibitors that block GRB-2 interaction with its binding partners (such as, for example, protein tyrosine kinase molecules). Given these activities, the compounds may represent anti-cell proliferation agents.

5.4 Example

LDH Cytotoxicity Assay

The Example presented herein demonstrates that the compounds (h) 2,5-dihydroxy-6-[2-(3-methyl-n-butyl)indol-3-yl]-3-(2-phenylindol-3-yl)-1,4-quinone, (i) 2,5-dihydroxy-6-(2-methylindol-3-yl)-3-(2-phenylindol-3-yl)-1,4-quinone are cytotoxic to cells, in comparison to compound (m) 3-(2-carboxyindol-3-yl)-2,5-dihydroxy-6-(2-phenylindol-3-yl)-1,4-quinone.

5.4.1 Materials and Methods

On Day 0, A431 cells were plated at an appropriate density in a 96-well flat-bottomed plate in 100 µl of media per well. Cells were allowed to attach overnight. On Day 1, 120 µl of growth media were added to all wells in columns 1–11 in the 96-well plate.

In a second 96-well plate, one of the compounds to be tested (solubilized in DMSO) and 240 µl media at a 2x final drug concentration (generally, 2x=0.4% DMSO) were added to wells in column 12, at rows A, B, C, and D. Another of the compounds to be tested was similarly added in column 12, at rows E, F, G and H. The compounds were serially diluted in growth medium from columns 12 through column 2 at 1:2 (120 µl). Column 1, the control sample, was untreated with compound. Once the serial dilution was complete, 100 µl of compound plus media were transferred to the analogous wells in the plate containing the cells, giving a final compound concentration of 1x(0.2% DMSO). The compounds were allowed to incubate with the cells for four days.

On Day 5, the medium on the dosed cells was transferred to a new 96-well plate (supernatant) and any remaining medium was removed from the dosed cells. Fresh medium was added to the cells (lysate). All plates were frozen at −80° C. for two hours to overnight. The plates were then thawed at 37° C., and 50 µl of sample was added to new plates, along with 50 µl of LDH substrate mix (Cyto-96, non-radioactive cytotoxicity assay kit, Cat #G1780, Promega). Plates were incubated in the dark for 15–30 minutes, and 50 µl of stop solution was added to each sample. Plates were read within 30 minutes of adding the stop solution on a plate reader with a 490 nm filter and a 630 nm reference filter.

The toxicity was calculated as follows: % Toxicity= $(OD_{sup}/(OD_{sup}+OD_{lys}))\times 100$, where OD=optical density read with the plate reader. Basic toxicity/background was calculated from the untreated sample and was subtracted from the calculated values derived from the treated samples.

5.4.2 Results

A431 cells, which overexpress EGF receptor, were contacted with (h) 2,5-dihydroxy-6-[2-(3-methyl-n-butyl)indol- 3-yl]-3-(2-phenylindol-3-yl)-1,4-quinone, (i) 2,5-dihydroxy-6-(2-methylindol-3-yl)-3-(2-phenylindol-3-yl)-1,4-quinone, or (m) 3-(2-carboxyindol-3-yl)-2,5-dihydroxy-6-(2-phenylindol-3-yl)-1,4-quinone to test the cytotoxicity of the compounds in the LDH cytoxicity assay, described above, in Section 5.4.1. The results show that the $EC_{50}$, which is the dose that is cytotoxic to 50% of the cells, is 6.5 μM for compound (h), and 10.2 μM for compound (i). In contrast, compound (m) is not cytotoxic to cells, with an $EC_{50}$ of greater than 100 μM.

5.5 Example

In Vivo Inhibition of Tumor Growth

The Example presented herein demonstrates that the compounds of the present invention are effective in vivo inhibitors of tumor growth.

5.5.1 Materials and Methods

A431cells were grown in culture, as described in Section 5.4.1, supra, and implanted subcutaneously into the hind-flank of a female Balb/c nu/nu mouse at $3 \times 10^6$ in 100 μl of PBS on Day 0. The compounds (h) 2,5-dihydroxy-6-[2-(3-methyl-n-butyl)indol-3-yl]-3-(2-phenylindol-3-yl)-1,4-quinone and (i) 2,5-dihydroxy-6-(2-methylindol-3-yl)-3-(2-phenylindol-3-yl)-1,4-quinone at 75 mg/kg/day or 100 mg/kg/day in DMSO, were administered intraperitoneally (IP) in a volume of 50 μl beginning on Day 1. Tumors were measured using venier calipers and tumor volume is calculated as a product of tumor length, width, and height.

5.5.2 Results

In vivo studies with A431 vulvar carcinoma tumor cells were performed using the xenograft model in athymic mice. The compounds (h) 2,5-dihydroxy-6-[2-(3-methyl-n-butyl)indol-3-yl]-3-(2-phenylindol-3-yl)-1,4-quinone and (i) 2,5-dihydroxy-6-(2-methylindol-3-yl)-3-(2-phenylindol-3-yl)-1,4-quinone effectively inhibited tumor cell growth in vivo by 49% at 75 mg/kg/day and 55% at, 100 mg/kg/day for compound (h) and by 35% at 75 mg/kg/day and 51% at 100 mg/kg/day for compound (i).

5.6 Example

Insulin Receptor Activation

5.6.1 Materials and Methods

NIH 3T3 cells overexpressing human insulin receptor (H25 cells) were seeded into 24-well plates and grown to confluence. They were then deprived of serum by overnight incubation in DMEM containing 0.1% BSA (starvation medium).

Time course experiments. The H25 cells were then stimulated with insulin (100 nM) or were exposed to a particular test compound as indicated (100 μM) in starvation medium at 37° C. Aliquots of cells were removed at various time points after stimulation. The cells were lysed in 50 μl of 2×SDS-PAGE loading buffer. Ten microliters of each lysate were fractionated on an 8% SDS polyacrylamide gel and then transferred to nitrocellulose. The blot was probed with PY99 (anti-pTyr/HRP conjugate; Santa Cruz Biotechnology) and visualized with ECL reagents (Amersham).

Non-time course experiments. The H25 cells were stimulated with insulin (100 nM) or were exposed to a particular test compound as indicated (100 μM) in starvation medium for 20 min. at 37° C. After this stimulation period, the medium was removed and the cells were lysed in 50 μl of 2×SDS-PAGE loading buffer. Ten microliters of each lysate were fractionated on an 8% SDS polyacrylamide gel and then transferred to nitrocellulose. The blot was probed with PY99 (anti-pTyr/HRP conjugate; Santa Cruz Biotechnology) and visualized with ECL reagents (Amersham).

5.6.2 Results

Time course data were obtained for the following compounds: (h) 2,5-dihydroxy-6-[2-(3-methyl-n-butyl)indol-3-yl]-3-(2-phenylindol-3-yl)-1,4-quinone; (k) 2,5-dihydroxy-3,6-di-[2-(2-phenylethyl)indol-3-yl]-1,4-quinone; (u) 2,5-dihydroxy-3-(1,2-dimethylindol-3-yl)-6-(2-methylindol-3-yl)-1,4-quinone; (v) 3-(1-benzyl-2-methylindol-3yl)-2,5-dihydroxy-6-(2-methylindol-3-yl)-1,4-quinone; and insulin. Within five minutes of stimulation with insulin, two phosphoprotein bands corresponding to the insulin receptor β subunit (95 kDa) and IRS (130 kDa) could be observed. Maximal phosphorylation of the insulin receptor β subunit was observed about 30 minutes after exposure to insulin, and then slowly decreased. In contrast, the amount of phospho-IRS remained fairly constant for the duration of the experiment (2 hours). Each of the compounds tested induced protein phosphorylation with a time course similar to that of insulin. Based on Applicants' experimentation, a beneficial property of an insulin mimetic compound may be that it not only stimulates phosphorylation of the insulin receptor tyrosine kinase, but that it also allows dephosphorylation, i.e., deactivation, of the receptor to occur in order to shut down the insulin stimulated pathway. Like insulin, all compounds tested in this experiment transiently activated the insulin receptor PTK and exhibit similar time-course profiles.

Various compounds were also tested in non-time-course experiments in order to determine whether they could stimulate tyrosine phosphorylation of the insulin receptor PTK. These compounds include:

(a) 2,5-dihydroxy-3,6-di-(2-methylindol-3-yl)-1,4-quinone;
(b) 2,5-dihydroxy-3,6-di-[2-(3-methyl-n-butyl)indol-3-yl]-1,4-quinone;
(c) 2,5-dihydroxy-3,6-di-(3-ethylindol-3-yl)-1,4-quinone;
(d) 2,5-dihydroxy-3,6-di-(2-n-butylindol-3-yl)-1,4-quinone;
(e) 2,5-diacetoxy-3,6-di-[2-(3-methyl-n-butyl)indol-3-yl]-1,4-quinone;
(f) 3-(2-carboxyindol-3-yl)-2,5-dihydroxy-6-(2-methylindol-3-yl)-1,4-quinone;
(g) 2,5-dihydroxy-3,6-di-(2-phenylindol-3-yl)-1,4-quinone;
(h) 2,5-dihydroxy-6-[2-(3-methyl-n-butyl)indol-3-yl]-3-(2-phenylindol-3-yl)-1,4-quinone;
(i) 2,5-dihydroxy-6-(2-methylindol-3-yl)-3-(2-phenylindol-3-yl)-1,4-quinone;
(j) 6-(2-n-butylindol-3-yl)-3-(2-carboxyindol-3-yl)-2,5-dihydroxy-1,4-quinone;
(k) 2,5-dihydroxy-3,6-di-[2-(2-phenylethyl)indol-3-yl]-1,4-quinone;
(l) 3-(2-carboxyindol-3-yl)-2,5-dihydroxy-6-[2-(3-methyl-n-butyl)indol-3-yl]-1,4-quinone;
(m) 3-(2-carboxyindol-3-yl)-2,5-dihydroxy-6-(2-phenylindol-3-yl)-1,4-quinone;
(n) 3-(2-n-butylindol-3-yl)-6-(2-carboxy-5-chloroindol-3-yl)-2,5-dihydroxy-1,4-quinone;
(o) 2,5-dihydroxy-3,6-di-(5-methoxy-2-methylindol-3-yl)-1,4-quinone;
(p) 3,6-di-(5-chloro-2-methylindol-3-yl)-2,5-dihydroxy-1,4-quinone;

(q) 3-(2-carboxy-5-chloroindol-3-yl)-2,5-dihydroxy-6-(2-methyl-5-methoxyindol-3-yl)-1,4-quinone;
(r) 2,5-dihydroxy-3,6-di-(2-naphthylindol-3-yl)-1,4-quinone;
(s) 3-[2-(N-butylcarboxamido)-indol-3-yl)]-6-(n-butylindol-3-yl)-2,5-dihydroxy-1,4-quinone;
(t) 2,5-dimethoxy-3,6-di-[2-(3-methyl-n-butyl)indol-3-yl]-1,4-quinone;
(u) 2,5-dihydroxy-3-(1,2-dimethylindol-3-yl)-6-(2-methylindol-3-yl)-1,4-quinone;
(v) 3-(1-benzyl-2-methylindol-3-yl)-2,5-dihydroxy-6-(2-methylindol-3-yl)-1,4-quinone; and
(w) 2-hydroxy-5-methoxy-3,6-di-[2-(3-methyl-n-butyl)-indol-3-yl]-1,4-quinone.

Stimulation of cells with insulin for 20 minutes results in the appearance of phosphorylated β subunit of the insulin receptor protein tyrosine kinase (95 kD) and IRS-1 (130 kD), a downstream protein in the insulin signaling cascade. Compounds (h), (i), (j), (k), (l), (m), (o), (p), (q), (r), (s), (t), (u), (v), and (w) stimulate the tyrosine phosphorylation of a protein that has the approximate molecular weight of the insulin receptor protein tyrosine kinase β subunit. In addition, compounds (a), (b), (c), (h), (k), (o), (q), (r) and (v) stimulate the tyrosine phosphorylation of a protein that has the approximate molecular weight of IRS-1. These results may indicate that the compounds mimic insulin action by stimulating the tyrosine phosphorylation of the insulin receptor PTK β subunit or of IRS-1.

5.7 Example

Quantitation of Insulin Receptor Stimulation Elisa Assay

5.7.1 Materials and Methods

NIH 3T3 cells overexpressing human insulin receptor (H25 cells) were seeded into 96-well plates and grown to confluence. They were then deprived of serum by overnight incubation in DMEM containing 0.1% BSA (starvation medium). Cells were then left unstimulated (negative control), stimulated with insulin (100 nM) (positive control) or were exposed to a particular test compound as indicated (100 μM) in starvation medium for 20 min. at 37° C. After this stimulation period, the medium was removed and the cells were lysed in 100 μl of HNTG (20 mM HEPES, pH 7.5, 150 mM NaCl, 10% glycerol, 0.5% Triton X100) and insulin receptor was captured in the wells of a 96-well plate coated with anti-insulin receptor beta subunit antibody. Wells were washed three times with 100 μl of TBST (50 mM TRIS, pH 7.5, 150 mM NaCl, 0.1% Triton X100). Anti-phosphotyrosine/HRP conjugate (PY99; Santa Cruz Biotecnology) in TBST containing 1% BSA was then added to the wells and incubated at room temperature for one hour. The wells were subsequently washed three times with 100 μl TBST and once with water and then incubated with the HRP substrate ABTS (5' to 3') in order to quantitate the amount of insulin receptor β subunit that was tyrosine phosphorylated.

5.7.2 Results

The amount of tyrosine phosphorylation of the insulin receptor tyrosine kinase β subunit is an indication of the degree to which cells are stimulated by a particular compound. The results of the ELISA assay are quantitated in FIG. 1. These results indicate that, upon stimulation of cells with insulin, there is an 8.7-fold increase of insulin receptor tyrosine kinase β subunit tyrosine phosphorylation compared with unstimulated cells. The results further indicate that several asterriquinone compounds stimulate insulin receptor tyrosine kinase β subunit tyrosine phosphorylation compared with unstimulated cells. In particular, stimulation of cells with compound (k) (see previous example for nomenclature) increases the phosphorylation of the insulin receptor PTK about 3.6-fold compared with unstimulated cells. Similarly, stimulation of cells with compound (l) increases insulin receptor PTK phosphorylation about 3.3-fold compared with unstimulated cells, stimulation of cells with compound (p) increases insulin receptor PTK phosphorylation about 2-fold compared with unstimulated cells, and stimulation of cells with compound (v) increases insulin receptor PTK phosphorylation about 6.3-fold. Thus, a number of these asterriquinone compounds, and particularly compound (v), stimulate insulin receptor activation almost to the level of insulin, indicating their potential utility as insulin mimetics.

5.8 Example

Lowering of Blood Glucose Levels in DB/DB Mice

5.8.1 Materials and Methods

Acute glucose lowering. Nine-week-old male db/db mice (Jackson Laboratories) are orally treated (by gavage) with vehicle (0.5% methylcellulose) or with single doses of test compounds at 5 mg/kg and at 25 mg/kg, followed by immediate removal of food. Mice continue to have free access to water. Blood glucose is monitored before and after dosing at 1-hour intervals with a One Touch Glucometer (Lifescan, Milpitas, Calif.). Lean mice that are not dosed serve as a control.

Long-term dosing for glucose lowering. Eight-week-old male db/db mice are treated daily with an oral dose of vehicle or of test compounds at doses of 5 mg/kg/day or 20 mg/kg/day. Mice are fed ad libitum. Blood glucose is monitored with a glucometer. Lean mice that are not dosed serve as a control.

5.8.2 Results

Blood glucose levels are monitored in mg/dl blood volume over time (hours for acute glucose lowering tests and days for long-term dosing experiments) for db/db mice treated with various test compounds and for control mice. Test compounds that transiently lower blood glucose levels by more than 50% or that significantly correct blood glucose levels over time independent of food intake are considered to be insulin mimetic compounds.

All publications and patent applications are herein incorporated by reference to the same extent as if each individual publication or patent application was specifically and individually indicated to be incorporated by reference.

Although only a few embodiments have been described in detail above, those having ordinary skill in the molecular biology art will clearly understand that many modifications are possible in the preferred embodiment without departing from the teachings thereof. All such modifications are intended to be encompassed within the following claims.

What is claimed is:

1. A compound of the formula:

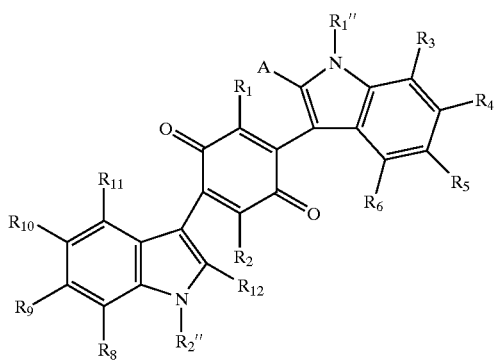

wherein $R_1$ and $R_2$ are —OH, $R''_1$ is arylalkyl, $R''_2$ is H or arylalkyl, $R_7$ and $R_{12}$ are branched or unbranched $C_1$–$C_7$ alkyl, and $R_3$–$R_6$, and $R_8$–$R_{11}$ are H, or a pharmaceutically acceptable salt thereof.

2. A compound of the formula:

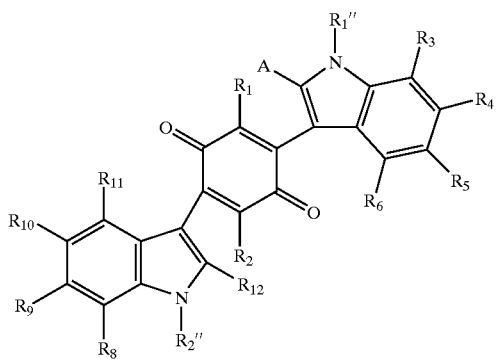

wherein:

$R_1$ and $R_2$ are each OH;

$R''_1$ and $R''_2$ are each independently H, unbranched $C_1$–$C_7$ alkyl, unbranched $C_2$–$C_7$ alkenyl, $C_2$–$C_7$ alkynyl, aryl or arylalkyl; and $R_3$ to $R_6$ and $R_8$ to $R_{12}$ are each independently hydrogen, branched or unbranched $C_1$–$C_n$ alkyl, alkylcarboxy, unbranched $C_2$–$C_m$ alkenyl, $C_2$–$C_m$ alkynyl, alkenylcarboxy, aryl, alkylaryl, hydroxy, unbranched hydroxyalkyl, $C_1$–$C_n$ alkoxy, nitro, halo, trihalomethyl, amido, carboxamido, carboxy, —S(O)$_2$R, wherein R is H, alkyl, alkenyl, alkynyl, aryl, alkylaryl, heteroaryl, bicyclic aryl or hydroxyalkyl; sulfonamido, amino, or mercapto, wherein n is an integer from 0–12, and m is an integer from 0 to 12, $R_7$ is alkylcarboxy, unbranched $C_5$–$C_m$ alkenyl, $C_{2-C_m}$ alkynyl, alkenylcarboxy, aryl, hydroxy, unbranched hydroxyalkyl, trihalomethyl, amido, carboxy, —S(O)$_2$R, wherein R is H, alkyl, alkenyl, alkynyl, aryl, alkylaryl, heteroaryl, bicyclic aryl or hydroxyalkyl; sulfonamido, amino, or mercapto, wherein n is an integer from 0–12, and m is an integer from 0 to 12, or a pharmaceutically acceptable salt thereof.

3. A compound of the formula:

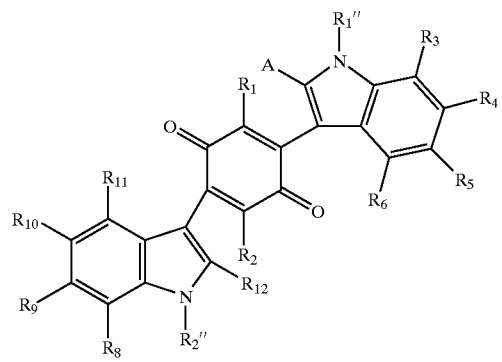

wherein:

$R_1$ and $R_2$ are each OH;

$R''_1$ and $R'_2$ are each independently H, unbranched $C_1$–$C_7$ alkyl, unbranched $C_2$–$C_7$ alkenyl, $C_2$–$C_7$ alkynyl, or aryl; and $R_3$ to $R_6$ and $R_8$ to $R_{12}$ are each independently hydrogen, branched or unbranched $C_1$–$C_n$ alkyl, alkylcarboxy, unbranched $C_2$–$C_m$ alkenyl, $C_2$–$C_m$ alkynyl, alkenylcarboxy, aryl, alkylaryl, hydroxy, unbranched hydroxyalkyl, $C_1$–$C_n$ alkoxy, nitro, halo, trihalomethyl, amido, carboxamido, carboxy, —S(O)$_2$R, wherein R is H, alkyl, alkenyl, alkynyl, aryl, alkylaryl, heteroaryl, bicyclic aryl or hydroxyalkyl; sulfonamido, amino, or mercapto, wherein n is an integer from 0–12, and m is an integer from 0 to 12, $R_7$ is alkylcarboxy, unbranched $C_5$–$C_m$ alkenyl, $C_2$–$C_m$ alkynyl, alkenylcarboxy, aryl, hydroxy, unbranched hydroxyalkyl, trihalomethyl, amido, carboxy, —S(O)$_2$R, wherein R is H, alkyl, alkenyl, alkynyl, aryl, alkylaryl, heteroaryl, bicyclic aryl or hydroxyalkyl; sulfonamido, amino, or mercapto, wherein n is an integer from 0–12, and m is an integer from 0 to 12, or a pharmaceutically acceptable salt thereof.

4. A pharmaceutical composition suitable for administration to humans which comprises the compound of claim 2 and a pharmaceutically acceptable carrier or excipient.

* * * * *